US012678612B2

(12) United States Patent
Calomeni et al.

(10) Patent No.: US 12,678,612 B2
(45) Date of Patent: Jul. 14, 2026

(54) INTRAVASCULAR BLOOD PUMPS AND PUMPS WITH EXPANDABLE SCAFFOLDS

(71) Applicant: SUPIRA MEDICAL, INC., Los Gatos, CA (US)

(72) Inventors: Michael Calomeni, San Jose, CA (US); Brian D. Brandt, Morgan Hill, CA (US); Ari Ryan, San Jose, CA (US); Reza Shirazi, San Jose, CA (US); Gregory Michael Hamel, Redwood City, CA (US); Daniel Hildebrand, Santa Cruz, CA (US); Spencer Noe, Santa Cruz, CA (US)

(73) Assignee: Supira Medical, Inc., Los Gatos, CA (US)

( * ) Notice: Subject to any disclaimer, the term of this patent is extended or adjusted under 35 U.S.C. 154(b) by 272 days.

(21) Appl. No.: 18/549,128

(22) PCT Filed: Mar. 7, 2022

(86) PCT No.: PCT/US2022/019187
§ 371 (c)(1),
(2) Date: Sep. 5, 2023

(87) PCT Pub. No.: WO2022/187747
PCT Pub. Date: Sep. 9, 2022

(65) Prior Publication Data
US 2024/0149046 A1 May 9, 2024

Related U.S. Application Data

(60) Provisional application No. 63/193,544, filed on May 26, 2021, provisional application No. 63/157,360, filed on Mar. 5, 2021.

(51) Int. Cl.
*A61M 1/10* (2006.01)
*A61M 1/12* (2006.01)
(Continued)

(52) U.S. Cl.
CPC .......... *A61M 60/13* (2021.01); *A61M 60/237* (2021.01); *A61M 60/408* (2021.01); *A61M 60/857* (2021.01)

(58) Field of Classification Search
CPC .. A61M 60/13; A61M 60/237; A61M 60/414; A61M 60/806; A61M 60/808;
(Continued)

(56) References Cited

U.S. PATENT DOCUMENTS 4,625,712 A 12/1986 Wampler
4,753,221 A 6/1988 Kensey et al.
(Continued)

FOREIGN PATENT DOCUMENTS

CA 3014105 A1 8/2017
EP 3131599 A1 2/2017
(Continued)

*Primary Examiner* — Jon Eric C Morales
(74) *Attorney, Agent, or Firm* — Shay Glenn LLP

(57) ABSTRACT

Catheter blood pumps that include an expandable pump portion. The pump portions include a collapsible blood conduit that defines a blood lumen. The collapsible blood conduits include a collapsible scaffold adapted to provide radial support to the blood conduit. The pump portion also includes one or more impellers. The collapsible scaffold may include portions of differing radial stiffness based on location of the one or more impellers therein.

22 Claims, 40 Drawing Sheets

(51) Int. Cl.

| | | |
|---|---|---|
| *A61M 25/00* | (2006.01) | |
| *A61M 60/13* | (2021.01) | |
| *A61M 60/237* | (2021.01) | |
| *A61M 60/408* | (2021.01) | |
| *A61M 60/857* | (2021.01) | |

(58) Field of Classification Search

CPC ........ A61M 2205/0266; A61M 60/135; A61M 60/148; A61M 60/174; A61M 60/804; A61M 60/81; A61M 60/824; A61M 60/829; A61M 60/857; A61M 60/865; B33Y 80/00; F04D 29/181; F04D 29/247; F04D 29/528; F04D 29/542; F04D 3/00; F04D 3/02; F05B 2240/311; F05B 2280/5001

See application file for complete search history.

(56) References Cited

U.S. PATENT DOCUMENTS

| | | | |
|---|---|---|---|
| 5,061,256 | A | 10/1991 | Wampler |
| 5,287,858 | A | 2/1994 | Hammerslag et al. |
| 5,507,629 | A | 4/1996 | Jarvik |
| 5,735,892 | A | 4/1998 | Myers et al. |
| 6,007,478 | A | 12/1999 | Siess et al. |
| 6,053,943 | A | 4/2000 | Edwin et al. |
| 6,685,696 | B2 | 2/2004 | Fleischhacker et al. |
| 6,712,844 | B2 | 3/2004 | Pacetti |
| 7,022,100 | B1 | 4/2006 | Hosn et al. |
| 7,027,875 | B2 | 4/2006 | Siess et al. |
| 7,220,275 | B2 | 5/2007 | Davidson et al. |
| 7,828,710 | B2 | 11/2010 | Shifflette |
| 8,388,565 | B2 | 3/2013 | Shifflette |
| 8,485,961 | B2 | 7/2013 | Campbell et al. |
| 8,535,211 | B2 | 9/2013 | Campbell et al. |
| 8,591,393 | B2 | 11/2013 | Walters et al. |
| 8,597,170 | B2 | 12/2013 | Walters et al. |
| 8,721,517 | B2 | 5/2014 | Zeng et al. |
| 8,734,508 | B2 | 5/2014 | Hastings et al. |
| 8,814,776 | B2 | 8/2014 | Hastie et al. |
| 8,814,933 | B2 | 8/2014 | Siess |
| 8,849,398 | B2 | 9/2014 | Evans |
| 8,932,141 | B2 | 1/2015 | Liebing |
| 8,934,956 | B2 | 1/2015 | Glenn et al. |
| 9,028,216 | B2 | 5/2015 | Schumacher et al. |
| 9,028,392 | B2 | 5/2015 | Shifflette |
| 9,072,825 | B2 | 7/2015 | Pfeffer et al. |
| 9,138,518 | B2 | 9/2015 | Campbell et al. |
| 9,180,235 | B2 | 11/2015 | Forsell |
| 9,358,329 | B2 | 6/2016 | Fitzgerald et al. |
| 9,446,179 | B2 | 9/2016 | Keenan et al. |
| 9,512,839 | B2 | 12/2016 | Liebing |
| 9,833,550 | B2 | 12/2017 | Siess |
| 9,872,948 | B2 | 1/2018 | Siess |
| 10,052,419 | B2 | 8/2018 | Er |
| 10,208,763 | B2 | 2/2019 | Schumacher et al. |
| 10,357,598 | B2 | 7/2019 | Aboul-Hosn et al. |
| 10,881,770 | B2 | 1/2021 | Tuval et al. |
| 10,894,115 | B2 | 1/2021 | Pfeffer et al. |
| 11,268,521 | B2 | 3/2022 | Toellner |
| 11,280,345 | B2 | 3/2022 | Bredenbreuker et al. |
| 11,850,413 | B2 | 12/2023 | Zeng et al. |
| 12,017,056 | B2 | 6/2024 | Guo et al. |
| 12,220,570 | B2 | 2/2025 | Hildebrand et al. |
| 2005/0277803 | A1 | 12/2005 | Pecor |
| 2007/0250148 | A1 | 10/2007 | Perry et al. |
| 2008/0114339 | A1* | 5/2008 | McBride ............... F04D 29/542 |
| | | | 416/142 |
| 2014/0148638 | A1 | 5/2014 | LaRose et al. |
| 2014/0255176 | A1 | 9/2014 | Bredenbreuker et al. |
| 2015/0238671 | A1 | 8/2015 | Mesallum |
| 2015/0328382 | A1 | 11/2015 | Corbett et al. |
| 2016/0022890 | A1 | 1/2016 | Schwammenthal et al. |
| 2016/0053763 | A1 | 2/2016 | Toellner |
| 2016/0279310 | A1 | 9/2016 | Scheckel et al. |
| 2017/0014562 | A1 | 1/2017 | Liebing |
| 2017/0037860 | A1 | 2/2017 | Toellner |
| 2017/0100527 | A1 | 4/2017 | Schwammenthal et al. |
| 2017/0173242 | A1 | 6/2017 | Anderson et al. |
| 2017/0232169 | A1 | 8/2017 | Muller |
| 2017/0340788 | A1 | 11/2017 | Korakianitis et al. |
| 2018/0149164 | A1 | 5/2018 | Siess |
| 2018/0303990 | A1 | 10/2018 | Siess et al. |
| 2020/0121835 | A1 | 4/2020 | Farago et al. |
| 2020/0237981 | A1 | 7/2020 | Tuval et al. |
| 2020/0316268 | A1 | 10/2020 | Antoni et al. |
| 2021/0038786 | A1* | 2/2021 | Calomeni ........... A61M 60/804 |
| 2022/0203084 | A1 | 6/2022 | Zarins et al. |

FOREIGN PATENT DOCUMENTS

| | | | |
|---|---|---|---|
| EP | 3153190 | A1 | 4/2017 |
| EP | 3000493 | B1 | 5/2017 |
| JP | 2014523274 | A | 9/2014 |
| WO | WO01/019444 | A1 | 3/2001 |
| WO | WO2014/164292 | A1 | 10/2014 |
| WO | WO2015/177793 | A2 | 11/2015 |
| WO | WO2018/061002 | A1 | 4/2018 |
| WO | WO2018/067410 | A1 | 4/2018 |
| WO | WO2018/078615 | A1 | 5/2018 |
| WO | WO2018/088939 | A1 | 5/2018 |
| WO | WO2018/096531 | A1 | 5/2018 |
| WO | WO2019/094963 | A1 | 5/2019 |
| WO | WO2019/191851 | A1 | 9/2019 |
| WO | WO2019/194956 | A1 | 10/2019 |

* cited by examiner different pitch than

AA

LV

AV        320

AA

LV 321        320

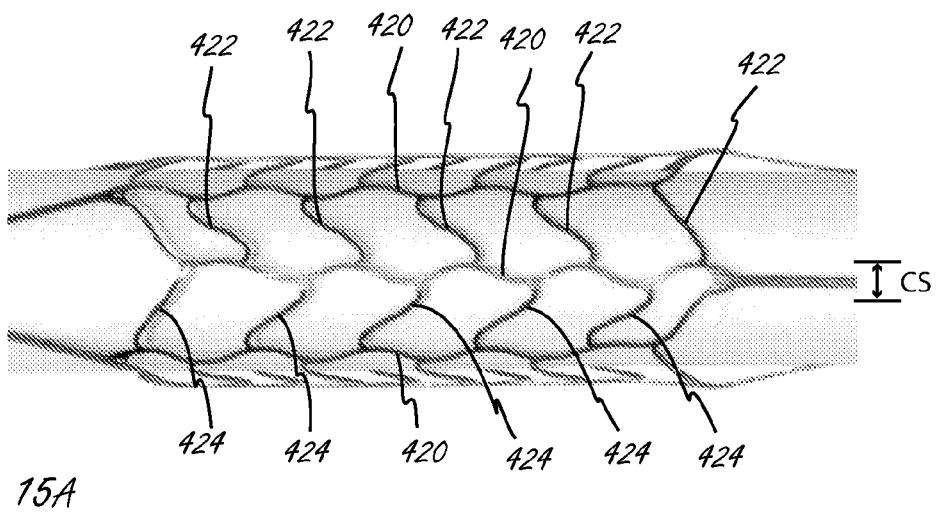
Fig. 15A
Fig. 15B
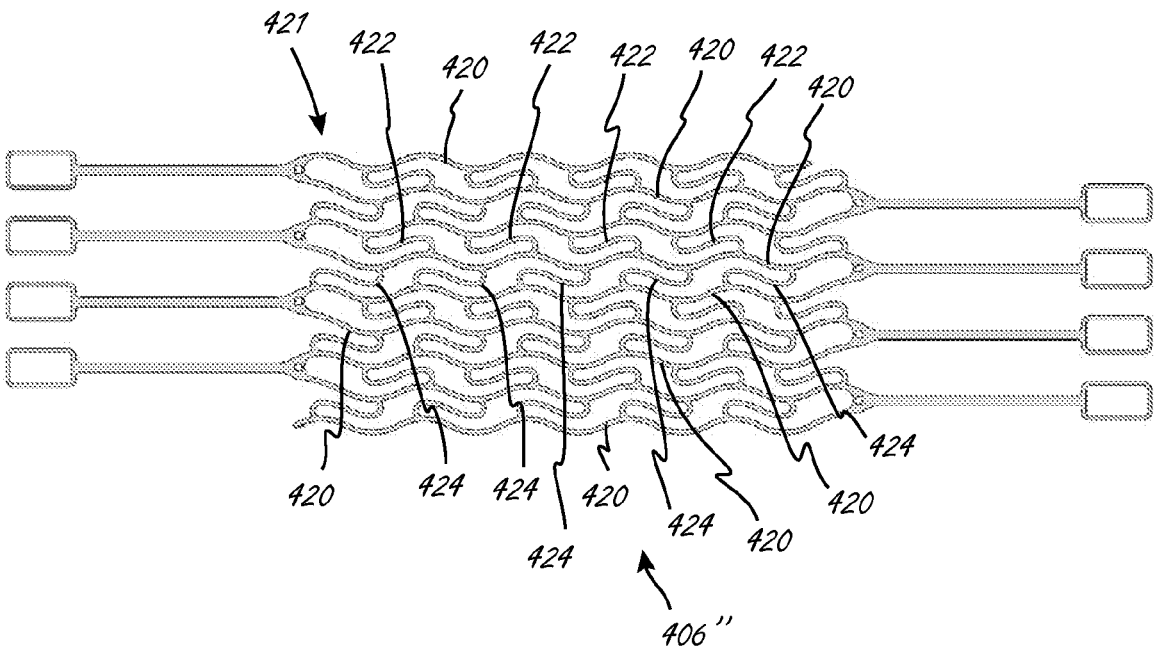

1

INTRAVASCULAR BLOOD PUMPS AND PUMPS WITH EXPANDABLE SCAFFOLDS

CROSS REFERENCE TO RELATED APPLICATIONS

This application claims the benefit of U.S. Provisional Application No. 63/157,360, filed on Mar. 5, 2021, and entitled "CATHETER BLOOD PUMPS AND COLLAPS-IBLE BLOOD CONDUITS", and U.S. Provisional Application No. 63/193,544, filed on May 26, 2021, and entitled "INTRAVASCULAR BLOOD PUMPS AND PUMPS WITH EXPANDABLE SCAFFOLDS", which are herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Patients with heart disease can have severely compromised ability to drive blood flow through the heart and vasculature, presenting for example substantial risks during corrective procedures such as balloon angioplasty and stent delivery. There is a need for ways to improve the volume or stability of cardiac outflow for these patients, especially during corrective procedures.

Intra-aortic balloon pumps (IABP) are commonly used to support circulatory function, such as treating heart failure patients. Use of IABPs is common for treatment of heart failure patients, such as supporting a patient during high-risk percutaneous coronary intervention (HRPCI), stabilizing patient blood flow after cardiogenic shock, treating a patient associated with acute myocardial infarction (AMI) or treating decompensated heart failure. Such circulatory support may be used alone or in with pharmacological treatment.

An IABP commonly works by being placed within the aorta and being inflated and deflated in counterpulsation fashion with the heart contractions, and one of the functions is to attempt to provide additive support to the circulatory system.

More recently, minimally-invasive rotary blood pumps have been developed that can be inserted into the body in connection with the cardiovascular system, such as pumping arterial blood from the left ventricle into the aorta to add to the native blood pumping ability of the left side of the patient's heart. Another known method is to pump venous blood from the right ventricle to the pulmonary artery to add to the native blood pumping ability of the right side of the patient's heart. An overall goal is to reduce the workload on the patient's heart muscle to stabilize the patient, such as during a medical procedure that may put additional stress on the heart, to stabilize the patient prior to heart transplant, or for continuing support of the patient.

The smallest rotary blood pumps currently available can be percutaneously inserted into the vasculature of a patient through an access sheath, thereby not requiring surgical intervention, or through a vascular access graft. A description of this type of device is a percutaneously-inserted ventricular support device.

There is a need to provide additional improvements to the field of ventricular support devices and similar blood pumps for treating compromised cardiac blood flow.

SUMMARY OF THE DISCLOSURE

The disclosure is related to intravascular blood pump and their methods of and manufacture.

One aspect of the disclosure is an intravascular blood pump, comprising a collapsible blood conduit defining an inner lumen for moving blood therethrough, the collapsible blood conduit including a proximal section defined by at least two annular rows of connector elements arranged around a central axis of the collapsible blood conduit, a distal section defined by at least one annular row of connector elements arranged around the central axis of the collapsible blood conduit, a central section disposed axially between the distal and proximal sections, the central section including a plurality of axially extending elongate elements arranged in a helical pattern, and a proximal impeller disposed within at least a portion of the proximal section.

In some embodiments, the proximal, central and distal scaffold sections are coupled together (optionally unitary).

In other embodiments, the central section has a relative flexibility compared to the distal and proximal sections such that, in response to a lateral force on the blood conduit in the distal impeller section, the blood conduit deforms and assumes a configuration in which the central section has a higher degree of bend than the proximal and distal sections.

In some examples, the central section includes at least one of material or structure such that when a rotational force is applied to a distal end of the blood conduit, the central section is less resistant to collapse than the proximal and distal sections.

In one embodiment, at least portions of the proximal and distal sections are free of helical scaffold patterns.

In some examples, the axially extending elongate elements extend between the least two annular rows of connector elements in the proximal section.

In some embodiments, the distal section is defined by at least two annular rows of connector elements arranged around the central axis of the collapsible blood conduit.

In some embodiments, the axially extending elongate elements extend between the least two annular rows of connector elements in the distal section.

In one example, the proximal section is defined by at least four annular rows of connector elements arranged around the central axis of the collapsible blood conduit.

In other examples, the connector elements in each annular row are in a zig-zag pattern.

In some embodiments, an angle between the connector elements and the axially extending elongate elements ranges from about 10 degrees and 50 degrees.

In some examples, an angle between the connector elements and the axially extending elongate elements ranges from about 10 degrees and 30 degrees.

In other examples, an angle between the connector elements and the axially extending elongate elements ranges from about 30 degrees and 50 degrees.

In some embodiments, an axial length of the scaffold ranges from about 50 mm to about 80 mm.

In other embodiments, the proximal section has a greater lateral bending stiffness than the distal section.

In some embodiments, the collapsible blood conduit comprises a scaffold configured to transition between a collapsed state and an expanded state, wherein the scaffold has a diameter ranging from 5.0 mm to 10 mm in the expanded state and a diameter ranging from 2.5 mm to 4.5 mm in the collapsed state.

In one embodiment, the pump further comprises a plurality of proximal struts extending proximally from the proximal section.

In some examples, the pump includes a plurality of distal struts extending distally from the distal section.

In other embodiments, the plurality of proximal struts numbers twice as many as the plurality of distal struts.

In one example, the intravascular blood pump includes ten proximal struts and five distal struts.

In another embodiment, a width of the distal struts is greater than a width of the proximal struts.

In some examples, the axially extending elongate elements increase in width near the distal section One aspect of the disclosure is an intravascular blood pump, comprising: a collapsible blood conduit having an inner lumen for passing blood therethrough, the collapsible blood conduit including a scaffold positioned and configured to provide radial support for the blood conduit, the scaffold including a proximal section having a greater radial stiffness than a distal section of the scaffold; a proximal impeller disposed within at least a portion of the proximal section of the scaffold; and a distal impeller disposed within at least a portion of the distal section of the scaffold.

In this aspect, the proximal section may have a greater axial length than the distal section.

In this aspect, the proximal section may include a first pattern of structural elements that define a first set of apertures, and the distal section may include a second pattern of structural elements that define a second set of apertures, wherein the first set of apertures are smaller than the second set of apertures.

In this aspect, the scaffold may include a central section between the proximal section and the distal section.

In this aspect, the proximal section may have a greater radial stiffness than the central section.

In this aspect, the distal section may have a greater radial stiffness than the central section.

In this aspect, the central section may be configured to laterally bend upon an applied lateral force to the distal section.

In this aspect, the scaffold may include elongate elements that extend axially within the proximal section, the central section, and the distal section.

In this aspect, portions of the elongate elements within the proximal section may be wider than portions of the elongate elements within the central section.

In this aspect, portions of the elongate elements within the distal section may be wider than portions of the elongate elements within the central section.

In this aspect, circumferentially adjacent elongate elements may be circumferentially connected by connector elements within the proximal section and the distal section.

In this aspect, the proximal section may include more connector elements than the distal section.

In this aspect, the connector elements may be configured to bend to move circumferentially adjacent elongate elements closer to each other when the scaffold transitions from an expanded state to a collapsed state.

In this aspect, the elongate elements are not connected to each other within the central section.

In this aspect, portions of the elongate elements within the central section may be arranged in a helical pattern around a central axis of the scaffold.

In this aspect, the scaffold may be configured to transition between a collapsed state and an expanded state.

In this aspect, the intravascular blood pump may further comprise a driveshaft operationally coupled to the proximal impeller and the distal impeller, wherein the scaffold surrounds at least a portion of the driveshaft.

In this aspect, the proximal impeller and the distal impeller may be configured to collapse with the collapsible blood conduit.

In this aspect, the scaffold may include elongate elements that extend axially along a length of the scaffold, wherein the axially extending elongate elements are connected by one or more annular rows of connector elements within the proximal section.

In this aspect, the elongate elements may be connected by three annular rows of connector elements within the proximal section.

In this aspect, the elongate elements may be connected by four annular rows of connector elements within the proximal section.

In this aspect, the elongate elements may be connected by five annular rows of connector elements within the proximal section.

In this aspect, the connector elements in each annular row may be in a zig-zag pattern.

In this aspect, the scaffold may include elongate elements that extend axially along a length of the scaffold, wherein the axially extending elongate elements are connected by a first set of annular rows of connector elements within the proximal section and a second set of annular rows of connector elements in the distal section, wherein the first set has a greater number of annular rows of connector elements than the second set.

In this aspect, the scaffold may include elongate elements that extend axially along a length of the scaffold and connector elements that connect the elongate elements, wherein an angle between the connector elements and the elongate elements ranges from about 10 degrees and 50 degrees.

In this aspect, the angle between the connector elements and the elongate elements may range from about 10 degrees and 30 degrees.

In this aspect, the angle between the connector elements and the elongate elements may range from about 30 degrees and 50 degrees.

In this aspect, an axial length of the scaffold may range from about 50 mm to about 80 mm.

In this aspect, the proximal section may have a greater lateral bending stiffness than a distal section.

In this aspect, the blood conduit may be configured to transition between a collapsed state and an expanded state, wherein the scaffold has a diameter ranging from 5.0 mm to 10 mm in the expanded state and a diameter ranging from 2.5 mm to 4.5 mm in the collapsed state.

One aspect of the disclosure is a method of using an intravascular blood pump, the method comprising: delivering the intravascular blood pump while in a collapsed state towards a heart; expanding a scaffold of the intravascular blood pump in at least a portion of the heart, the expanded scaffold providing radial support for a blood conduit defining an inner lumen, wherein a proximal section of the scaffold has a greater radial stiffness than a distal section of the scaffold; and causing a proximal impeller disposed within at least a portion of the proximal section of the scaffold and a distal impeller disposed within at least a portion of the distal section of the scaffold to rotate and to pump blood through the inner lumen of the blood conduit.

In this aspect, the method may further comprise expanding the proximal impeller and the distal impeller within the scaffold.

In this aspect, the proximal section may have a greater axial length than the distal section.

In this aspect, the method may further comprise positioning the intravascular blood pump within at least a portion of the heart such that when the scaffold is expanded, the proximal section of the scaffold provides more radial support to the blood conduit than the distal section of the scaffold (in some cases, the central section of the scaffold provides less radial support to the blood conduit than the distal section of the blood conduit).

In this aspect, the scaffold may include a central section between the proximal section and the distal section, the method further comprising positioning the intravascular blood pump within at least a portion of the heart such that a lateral force applied to the scaffold, optionally to a central portion (and optionally from native aortic valve leaflets), causes the central portion to laterally bend more than the proximal section and more than the distal section.

In this aspect, the scaffold may include elongate elements that extend axially within the proximal section and the distal section, wherein expanding the scaffold includes causing the elongate elements to move radially away from each other.

In this aspect, the method may further comprise collapsing the scaffold such that the elongate elements move radially inward toward each other.

In this aspect, the expanding may comprise positioning a central scaffold section at the location of aortic valve leaflets, positioning at least a portion of the distal section in a left ventricle, and positioning at least a portion of the proximal section in an ascending aorta, wherein the central scaffold has a flexibility such that when positioned at the location of the aortic valve leaflets, the central section assumes a configuration that has a higher degree of bend than the proximal and distal sections.

In this aspect, the proximal section may have a greater lateral bending stiffness than the distal section.

In this aspect, the scaffold may have a diameter ranging from 5.0 mm to 10 mm when expanded.

In this aspect, the method may further comprise collapsing the scaffold for positioning the scaffold within a sheath, wherein the scaffold has a diameter ranging from 2.5 mm to 4.5 mm when collapsed.

One aspect of the disclosure is an intravascular blood pump, comprising: a collapsible blood conduit defining an inner lumen for moving blood therethrough, the collapsible blood conduit including a distal impeller section, a proximal impeller section, and a central section axially between the distal and proximal impeller sections; a proximal impeller disposed within at least a portion of the proximal impeller section; and a distal impeller disposed within at least a portion of the distal impeller section.

In this aspect, the collapsible blood conduit may comprise a collapsible scaffold positioned and configured to provide radial support to the blood conduit, the proximal impeller section including a proximal scaffold section, the distal impeller section including a distal scaffold section, and the central section including a central scaffold section.

In this aspect, the proximal, central and distal scaffold sections may be coupled together (optionally unitary).

In this aspect, the central section may have a relative flexibility compared to the distal and proximal sections such that, in response to a lateral force on the blood conduit in the distal impeller section, the blood conduit deforms and assumes a configuration in which the central section has a higher degree of bend than the proximal and distal sections.

In this aspect, the central section may include at least one of material or structure such that when a rotational force is applied to a distal end of the blood conduit, the central section is less resistant to collapse than the proximal and distal sections.

In this aspect, the central section may include a helical scaffold pattern, wherein the helical scaffold pattern, wherein at least portions of the proximal and distal sections are free of helical scaffold patterns.

In this aspect, the scaffold may elongate elements that extend axially along a length of the scaffold, wherein the axially extending elongate elements are connected by one or more annular rows of connector elements within the proximal section.

In this aspect, the elongate elements may be connected by three annular rows of connector elements within the proximal section.

In this aspect, the elongate elements may be connected by four annular rows of connector elements within the proximal section.

In this aspect, the elongate elements may be connected by five annular rows of connector elements within the proximal section.

In this aspect, the connector elements in each annular row may be in a zig-zag pattern.

In this aspect, the scaffold may include elongate elements that extend axially along a length of the scaffold, wherein the axially extending elongate elements are connected by a first set of annular rows of connector elements within the proximal section and a second set of annular rows of connector elements in the distal section, wherein the first set has a greater number of annular rows of connector elements than the second set.

In this aspect, the scaffold may include elongate elements that extend axially along a length of the scaffold and connector elements that connect the elongate elements, wherein an angle between the connector elements and the elongate elements ranges from about 10 degrees and 50 degrees.

In this aspect, the angle between the connector elements and the elongate elements may range from about 10 degrees and 30 degrees.

In this aspect, the angle between the connector elements and the elongate elements may range from about 30 degrees and 50 degrees.

In this aspect, an axial length of the scaffold ranges from about 50 mm to about 80 mm.

In this aspect, the proximal impeller section may have a greater lateral bending stiffness than the distal impeller section.

In this aspect, the collapsible blood conduit may comprise a scaffold configured to transition between a collapsed state and an expanded state, wherein the scaffold has a diameter ranging from 5.0 mm to 10 mm in the expanded state and a diameter ranging from 2.5 mm to 4.5 mm in the collapsed state.

One aspect of the disclosure is an intravascular blood pump, comprising: a collapsible blood conduit defining an inner lumen for moving blood therethrough, the collapsible blood conduit including a collapsible scaffold; a plurality of struts (e.g., 2951, 2952) extending from the blood conduit, the plurality of struts disposed at either a pump inflow or a pump outflow; one or more impellers (optionally distal and proximal impellers) disposed at least partially within the blood conduit.

In this aspect, the plurality of struts may include a plurality of outflow struts, wherein a first of the plurality of outflow struts has a configuration that is different than at least one other outflow strut.

In this aspect, the first strut may have a proximal region that has a configuration that is that is different than a proximal region of at least one other outflow strut.

In this aspect, the proximal region may be a region of the strut that is not expandable and collapsible (optionally is coupled to a central hub), wherein a region of the first strut that is distal to the proximal region is coupled to the blood conduit (optionally unitary) and is expandable and collapsible.

In this aspect, the proximal region may have a width that is less than a width of at least one other outflow strut at the same axial location.

In this aspect, a second outflow strut may have a width at the axial location that is less than a width of at least one other outflow strut at the axial location (optionally the same width as the first strut).

In this aspect, the first and second circumferentially adjacent outflow struts may have, at an axial location, a width that is less than a width of at least one other outflow strut at the axial location.

In this aspect, the first and second circumferentially adjacent outflow struts may each have, at an axial location, a sensor housing recess formed therein, wherein the recesses circumferentially face each other.

In this aspect, the plurality of struts may include a plurality of inflow struts, wherein at least one inflow strut has a configuration that is different than at least one other inflow strut.

In this aspect, the different configuration may be any of the differences described or claimed herein (e.g., less width in a distal non-expandable region, circumferential recess, etc.).

In this aspect, a first outflow strut has a configuration that is different than at least one other outflow struts, and wherein a first inflow strut has a configuration that is different than at least one other inflow strut.

In this aspect, the first outflow flow and the first inflow strut may be circumferentially offset.

In this aspect, the first outflow flow and the first inflow strut may be circumferentially aligned (e.g., as shown by the "middle" struts in FIG. 29A).

In this aspect, first and second outflow struts may each have configurations that are different than at least other outflow struts (optionally to accommodate an outflow pressure sensor housing), and optionally at proximal non-expandable regions thereof.

In this aspect, first and second inflow struts may each have configuration that are different than at least other inflow strut (optionally to accommodate an inflow pressure sensor housing), and optionally at distal, non-expandable regions thereof.

In this aspect, at least one of the first and second inflow struts may be circumferentially offset from at least one of the outflow struts.

In this aspect, at least one of the plurality of struts may comprise a pressure sensor recess formed therein sized and positioned relative to a pressure sensor and/or pressure sensor housing to accommodate the presence of the pressure sensor and/or the pressure sensor housing.

In this aspect, the pressure sensor recess(es) may comprise a region with relatively less width.

In this aspect, the plurality of struts may have axially extending configurations.

In this aspect, the scaffold may include elongate elements that extend axially along a length of the scaffold, wherein the axially extending elongate elements are connected by one or more annular rows of connector elements within the proximal section.

In this aspect, the elongate elements may be connected by three annular rows of connector elements within the proximal section.

In this aspect, the elongate elements may be connected by four annular rows of connector elements within the proximal section.

In this aspect, the elongate elements may be connected by five annular rows of connector elements within the proximal section.

In this aspect, the connector elements in each annular row may be arranged in a zig-zag pattern.

In this aspect, the scaffold may include elongate elements that extend axially along a length of the scaffold, wherein the axially extending elongate elements are connected by a first set of annular rows of connector elements within the proximal section and a second set of annular rows of connector elements in the distal section, wherein the first set has a greater number of annular rows of connector elements than the second set.

In this aspect, the scaffold may include elongate elements that extend axially along a length of the scaffold and connector elements that connect the elongate elements, wherein an angle between the connector elements and the elongate elements ranges from about 10 degrees and 50 degrees.

In this aspect, the angle between the connector elements and the elongate elements may range from about 10 degrees and 30 degrees.

In this aspect, the angle between the connector elements and the elongate elements may range from about 30 degrees and 50 degrees.

In this aspect, an axial length of the scaffold may range from about 50 mm to about 80 mm.

In this aspect, the collapsible scaffold may include a proximal section having a greater lateral bending stiffness than a distal section of the collapsible scaffold.

In this aspect, the scaffold may be configured to transition between a collapsed state and an expanded state, wherein the scaffold has a diameter ranging from 5.0 mm to 10 mm in the expanded state and a diameter ranging from 2.5 mm to 4.5 mm in the collapsed state.

One aspect of the disclosure is an intravascular blood pump, comprising: a collapsible blood conduit having an inner lumen for passing blood therethrough, the collapsible blood conduit including a scaffold positioned and configured to provide radial support for the blood conduit, the scaffold including a proximal section, a central section and a distal section, the central section disposed between the proximal section and the distal section and more flexible than the distal section and the proximal section; a proximal impeller disposed within at least a portion of the proximal section of the scaffold; and a distal impeller disposed within at least a portion of the distal section of the scaffold, wherein a central section flexibility causes the central section to assume a bent configuration when the blood conduit is positioned across an aortic valve with the central section disposed at the location of aortic valve leaflets, the bent configuration causing a rotational axis of the proximal impeller to be dis-aligned with a rotational axis of the distal impeller.

In this aspect, the central section may comprise a plurality of helical portions, optionally circumferentially uncoupled to one another by the scaffold.

In this aspect, the proximal section, the central section, and the distal section may have different radial stiffnesses.

In this aspect, the proximal section may have a greater radial and lateral bending stiffness than the distal section.

In this aspect, the scaffold may be configured to transition between a collapsed state and an expanded state, wherein the scaffold has a diameter ranging from 5.0 mm to 10 mm in the expanded state and a diameter ranging from 2.5 mm to 4.5 mm in the collapsed state.

One aspect of the disclosure is a tubular scaffold for an intravascular blood pump, the tubular scaffold comprising: a first impeller section configured to house a first impeller; a second impeller section configured to house a second impeller; and a central section between the first and second impeller sections, the central section having a plurality of elongate elements that extend axially in a spiral arrangement and that are not connected to each other within the central section, wherein the spiral arrangement of elongate elements is configured to laterally bend the central section upon application of a lateral force applied to the tubular scaffold.

In this aspect, the first and second impeller sections may include connector elements that connect the elongate elements within the first and second impeller sections.

In this aspect, the elongate elements may be parallel to a central axis of the tubular scaffold within the first impeller section.

In this aspect, the elongate elements may be parallel to a central axis of the tubular scaffold within the second impeller section.

In this aspect, the central section may have a greater lateral flexibility than the first impeller section or the second impeller section.

In this aspect, the first and second impeller sections may each have a greater radial stiffness than the central section.

In this aspect, the first and second impeller sections may include connector elements that connect the elongate elements within the first and second impeller sections.

In this aspect, the tubular scaffold may include a plurality of struts that curve radially inward and are configured to connect to a central hub of the intravascular blood pump.

In this aspect, the tubular scaffold may be configured to transition between a radially expanded state and a radially collapsed state.

In this aspect, the central section may have a greater axial length that each of the first and second impeller sections.

In this aspect, the elongate elements may be connected by one or more annular rows of connector elements within the first impeller section.

In this aspect, the elongate elements may be connected by three annular rows of connector elements within the first impeller section.

In this aspect, the elongate elements may be connected by four annular rows of connector elements within the first impeller section.

In this aspect, the elongate elements may be connected by five annular rows of connector elements within the first impeller section.

In this aspect, the connector elements in each annular row may be arranged in a zig-zag pattern.

In this aspect, the tubular scaffold may further comprise a membrane that covers at least a portion of inner surfaces and/or outer surfaces of the tubular scaffold.

In this aspect, the elongate elements may extend axially through the first impeller section, the central section and the second impeller section.

In this aspect, the laterally bending the central section may cause the first impeller section to axially dis-align with respect to the second impeller section.

In this aspect, the first impeller section may have a greater radial and lateral bending stiffness than the second impeller section.

In this aspect, the tubular scaffold may be configured to transition between a collapsed state and an expanded state, wherein the tubular scaffold has a diameter ranging from 5.0 mm to 10 mm in the expanded state and a diameter ranging from 2.5 mm to 4.5 mm in the collapsed state.

One aspect of the disclosure is an intravascular blood pump, comprising: a tubular scaffold including: a proximal section at least partially enclosing a proximal impeller; a distal section at least partially enclosing a distal impeller; and a central section between the proximal and distal sections, the central section having a plurality of elongate elements that extend axially in a spiral arrangement and that are not connected to each other within the central section.

In this aspect, the spiral arrangement may provide a sufficient lateral flexibility to allow the central section to deflect upon a lateral force applied to the tubular scaffold.

In this aspect, deflecting the central section may cause the proximal section to axially dis-align with respect to the distal section.

In this aspect, deflecting the central section may cause the proximal section to axially dis-align with respect to the distal section.

In this aspect, the central section may be configured to return to an original shape after the lateral force is released from the tubular scaffold.

In this aspect, the proximal section may be axially aligned with respect to the distal section when the scaffold is returned to the original shape.

In this aspect, each of the proximal and distal sections may include a plurality of struts coupled to a central hub of the intravascular blood pump.

In this aspect, the tubular scaffold may surround at least a portion of a central driveshaft.

In this aspect, the driveshaft may be configured to laterally bend as the tubular scaffold laterally bends.

In this aspect, the proximal section may have a greater radial and lateral bending stiffness than the distal section.

In this aspect, the tubular scaffold may be configured to transition between a collapsed state and an expanded state, wherein the tubular scaffold has a diameter ranging from 5.0 mm to 10 mm in the expanded state and a diameter ranging from 2.5 mm to 4.5 mm in the collapsed state.

One aspect of the disclosure is a tubular scaffold for an intravascular blood pump, the tubular scaffold comprising: a first impeller section configured to at least partially house a first impeller, the first impeller section having a first scaffold pattern; and a second impeller section configured to at least partially house a second impeller, the second impeller section having a second scaffold pattern, wherein the first scaffold pattern is more tightly packed than the second scaffold pattern.

In this aspect, the first scaffold pattern may be associated with a first stiffness, and the second scaffold pattern is associated with a second stiffness, wherein the first stiffness is greater than the second stiffness.

In this aspect, the first and second stiffness may include one or more of a radial stiffness and a bending stiffness.

In this aspect, the tubular scaffold may further comprise a central section between the first and second impeller sections, the central section having looser packed scaffold pattern than each of the first impeller section and the second impeller section.

In this aspect, the central section may include a plurality of elongate elements that extend axially in a spiral arrangement and that are not connected to each other within the central section, wherein the spiral arrangement of elongate elements is configured to laterally bend the central section upon application of a lateral force applied to the tubular scaffold.

In this aspect, the first impeller section may be a proximal section, and the second impeller section is a distal section.

In this aspect, the tubular scaffold may be configured to transition between a collapsed state and an expanded state, wherein the tubular scaffold has a diameter ranging from 5.0 mm to 10 mm in the expanded state and a diameter ranging from 2.5 mm to 4.5 mm in the collapsed state.

These and other aspects are described herein.

12

Figures 13A, 13B, 13C:
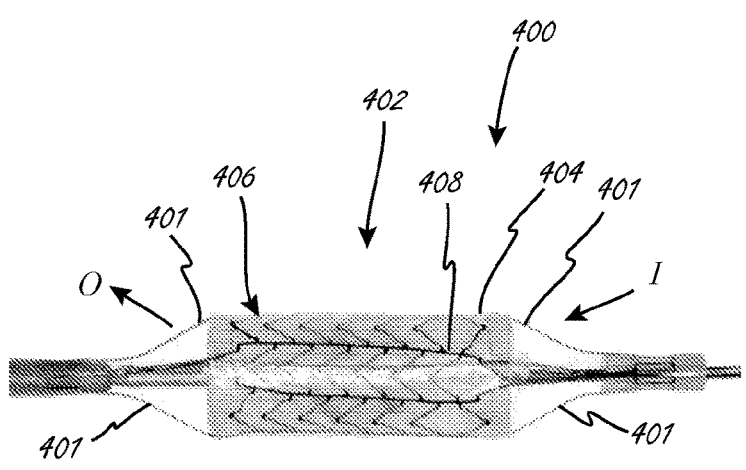
FIGS. 13A and 13B illustrate exemplary portions of an expandable pump portion.

FIG. 13C illustrates a scaffold from FIGS. 13A and 13B shown in a flattened and non-expanded configuration, as well as optional distal and proximal struts extending axially therefrom.

Figure 14A:
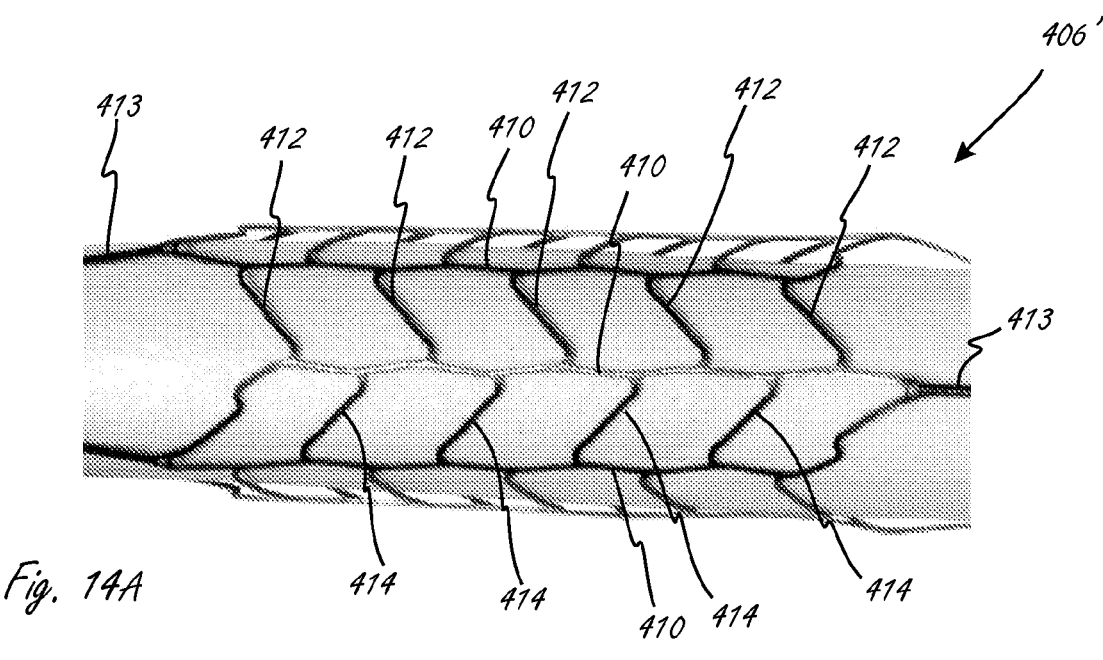

FIG. 14A illustrates an exemplary expanded scaffold that may be part of any of the expandable pump portions herein.

Figure 14B:
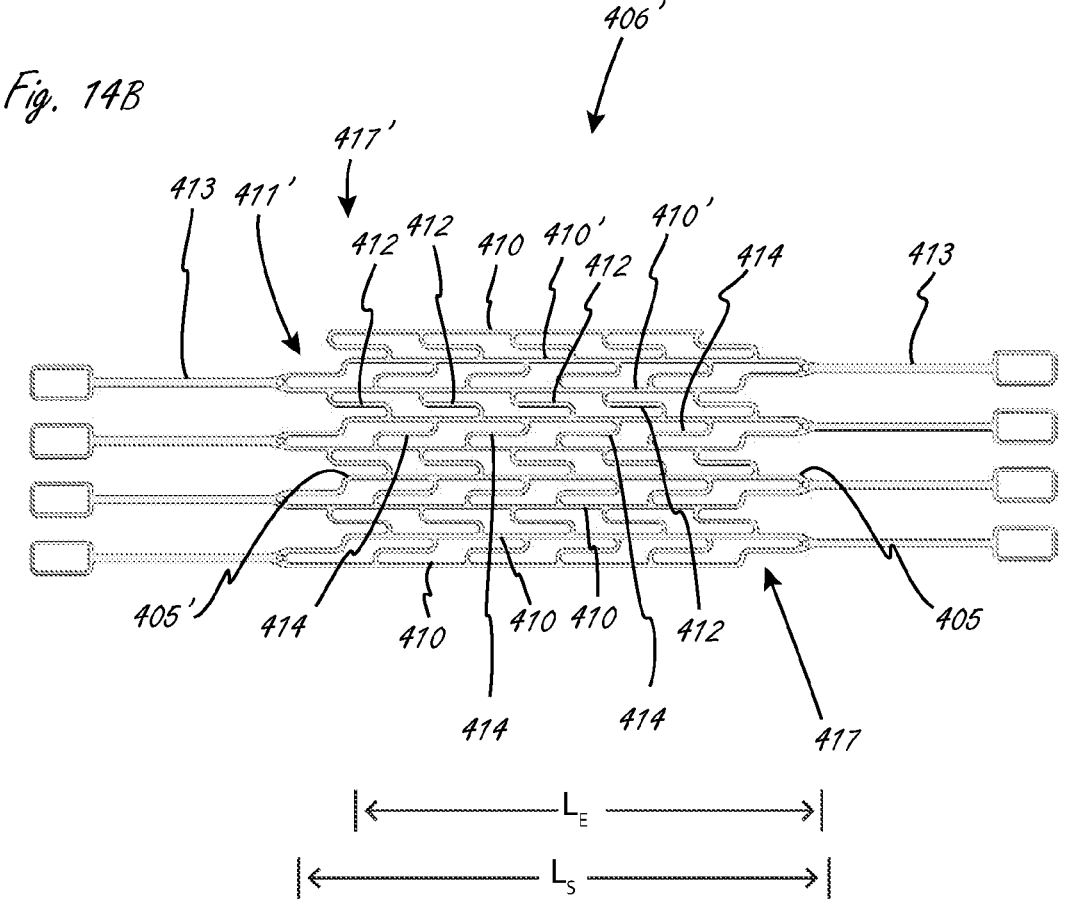

FIG. 14B illustrates the scaffold and struts from FIG. 14A in a flattened and non-expanded configuration.

FIG. 15A illustrates an exemplary expanded scaffold that may be part of any of the expandable pump portions herein.

FIG. 15B illustrates the scaffold and struts from FIG. 15A in a flattened and non-expanded configuration.

Figure 16:
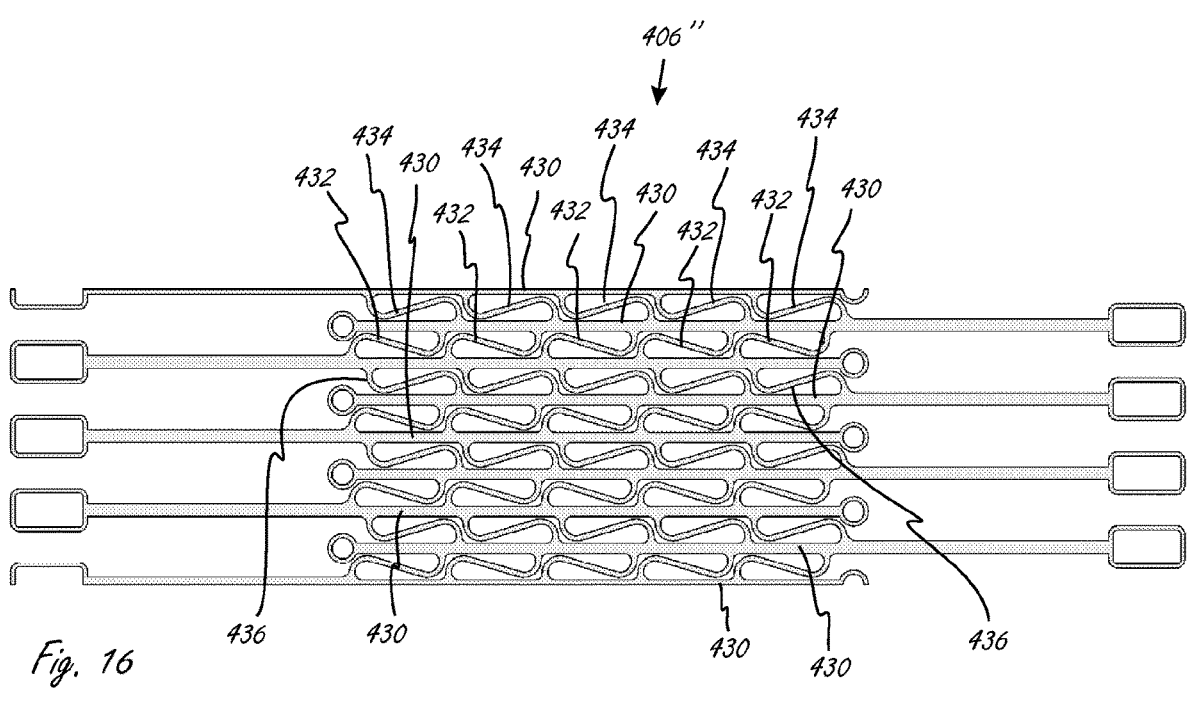

FIG. 16 illustrates an exemplary scaffold and optionally coupled struts in a flattened and non-expanded configuration.

Figure 17:
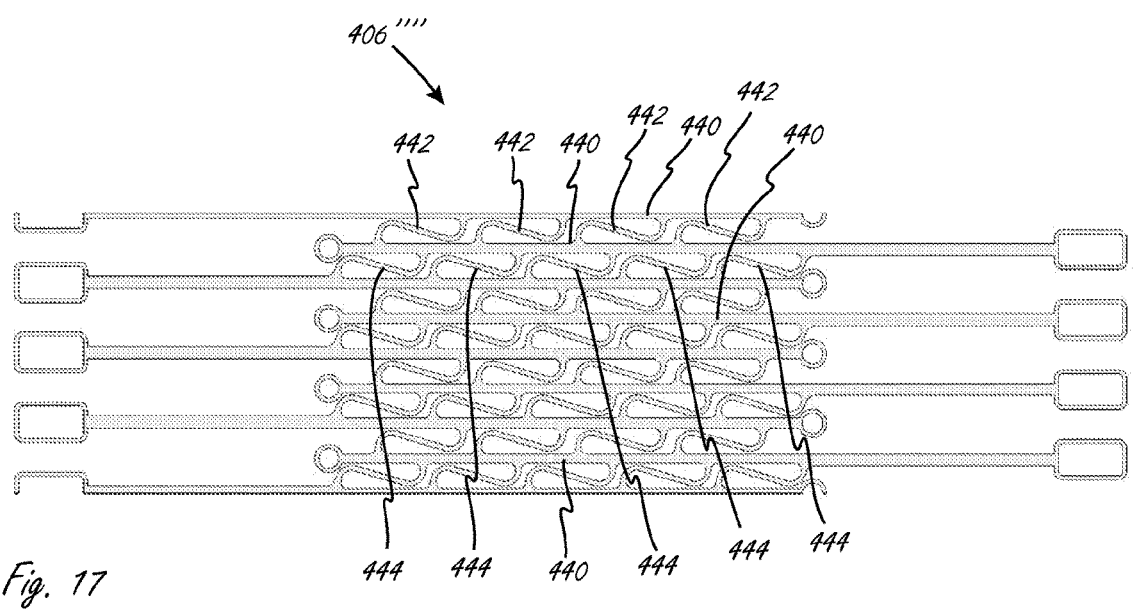

FIG. 17 illustrates an exemplary scaffold and optionally coupled struts in a flattened and non-expanded configuration.

Figures 18A, 18B:
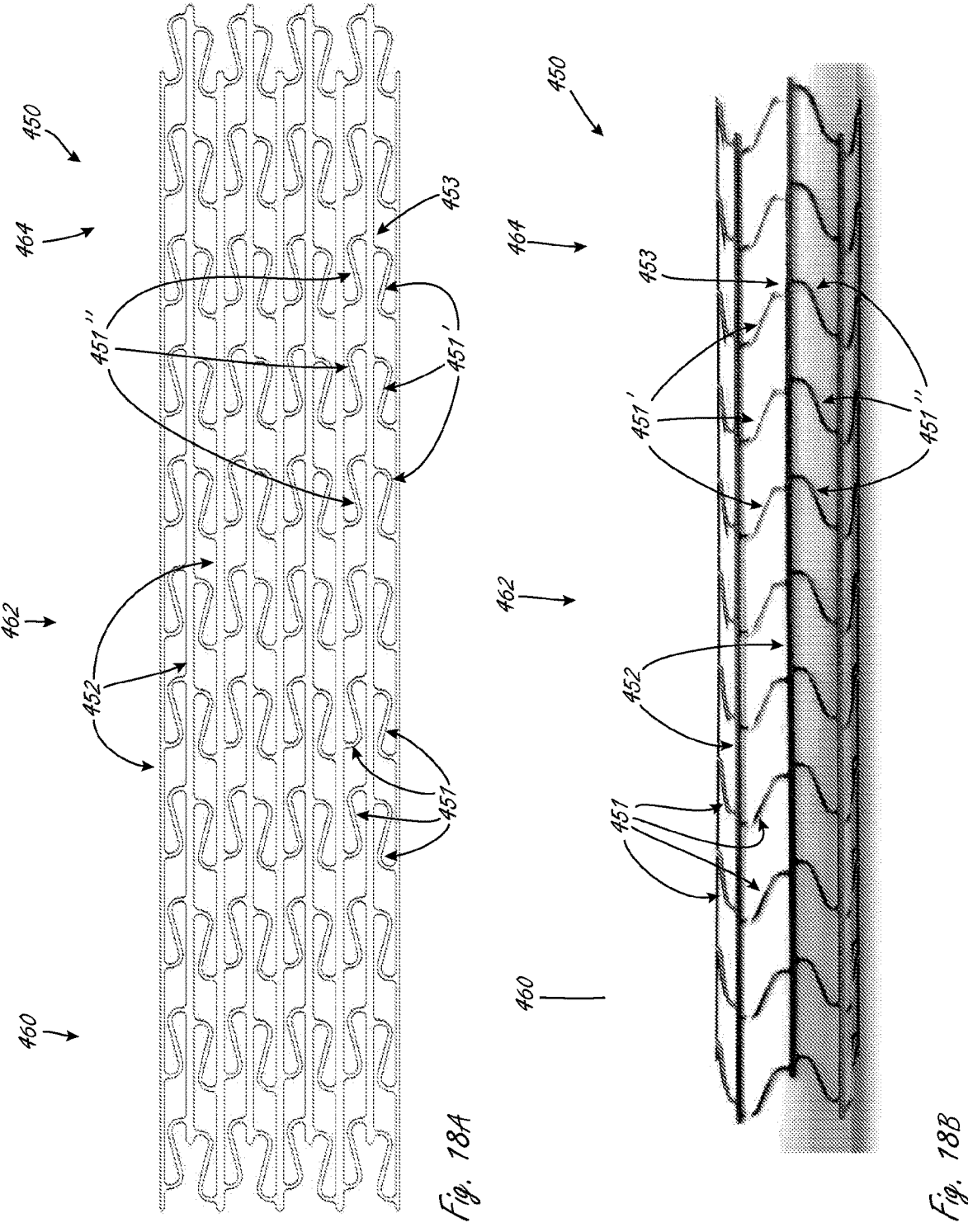

FIG. 18A illustrates an exemplary scaffold in a flattened and non-expanded configuration.

FIG. 18B illustrates the scaffold from FIG. 18A in an expanded configuration.

Figures 19A, 19B:
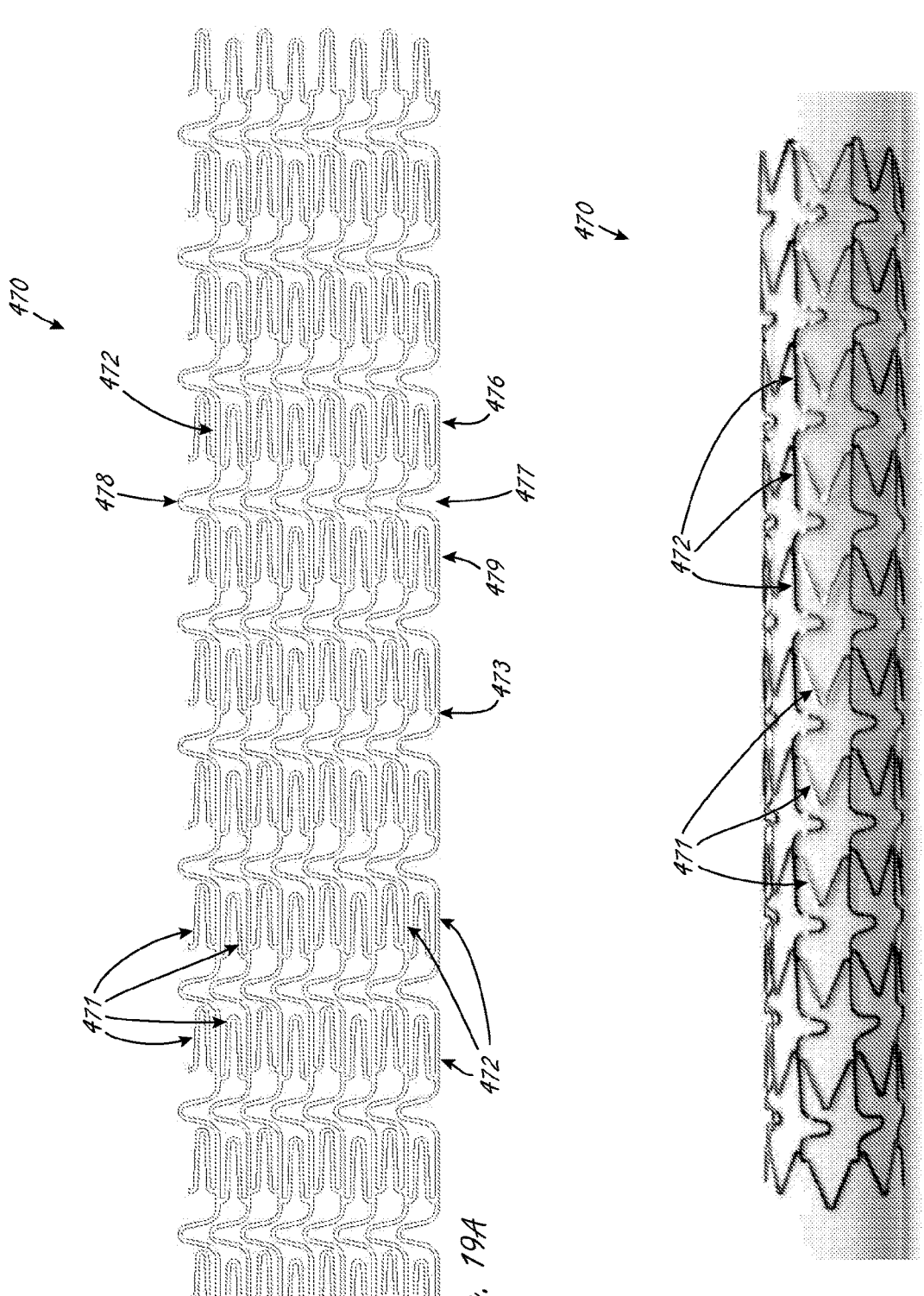

FIG. 19A illustrates an exemplary scaffold in a flattened and non-expanded configuration.

FIG. 19B illustrates the scaffold from FIG. 19A in an expanded configuration.

Figures 20A, 20B:
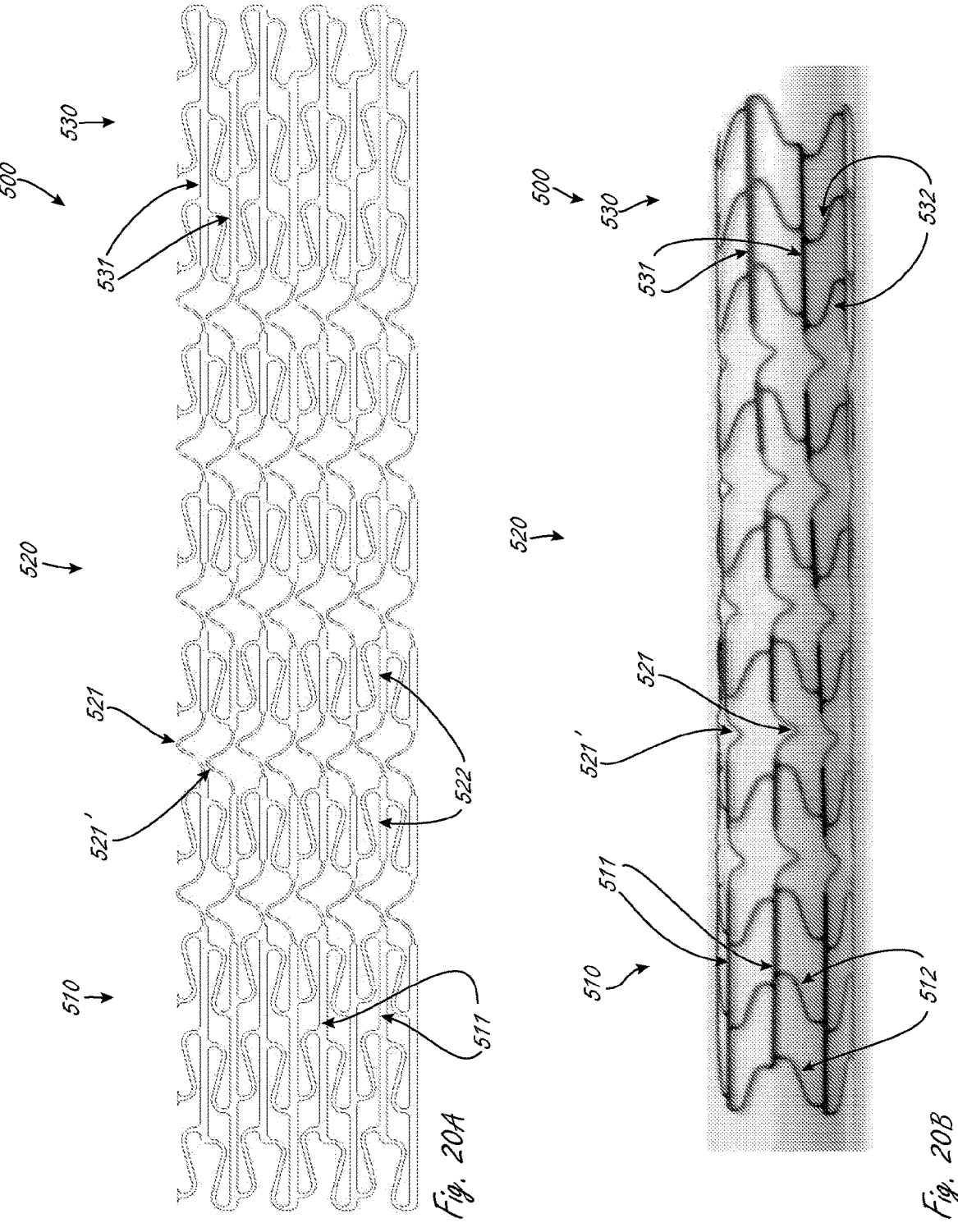

FIG. 20A illustrates an exemplary scaffold in a flattened and non-expanded configuration.

FIG. 20B illustrates the scaffold from FIG. 20A in an expanded configuration.

Figures 21A, 21B:
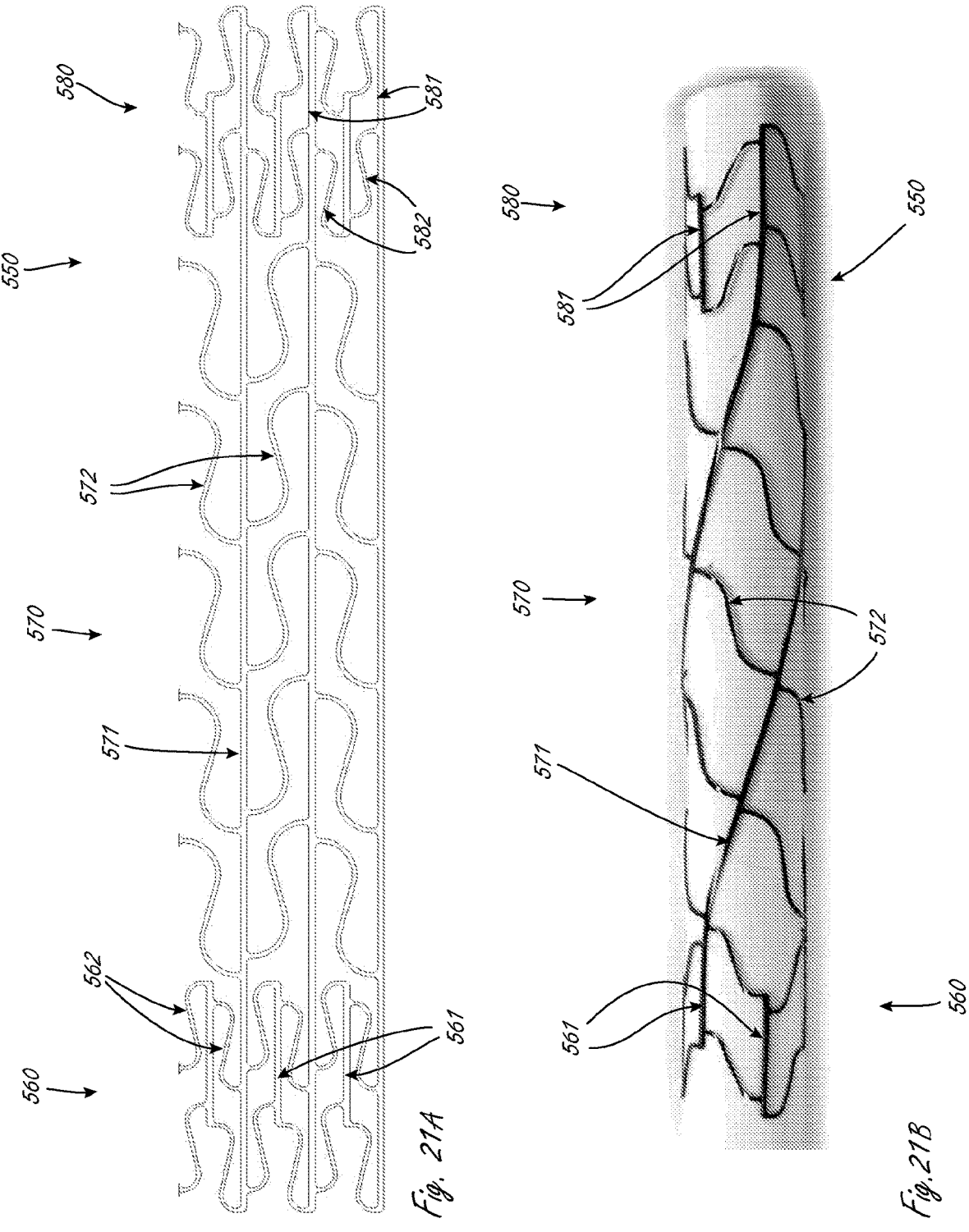

FIG. 21A illustrates an exemplary scaffold in a flattened and non-expanded configuration.

FIG. 21B illustrates the scaffold from FIG. 21A in an expanded configuration.

Figures 22A, 22B:
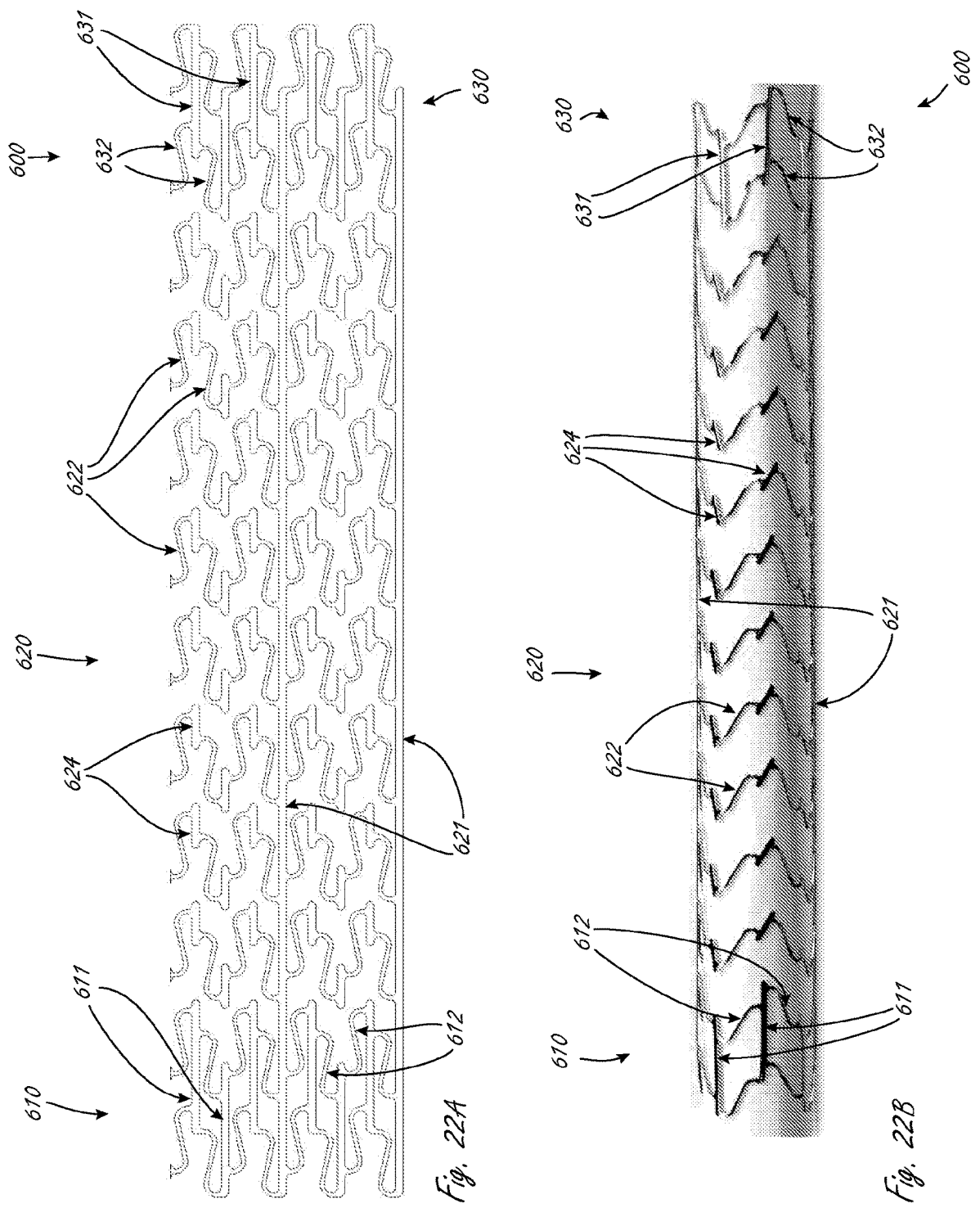

FIG. 22A illustrates an exemplary scaffold in a flattened and non-expanded configuration.

FIG. 22B illustrates the scaffold from FIG. 22A in an expanded configuration.

Figures 23A, 23B:
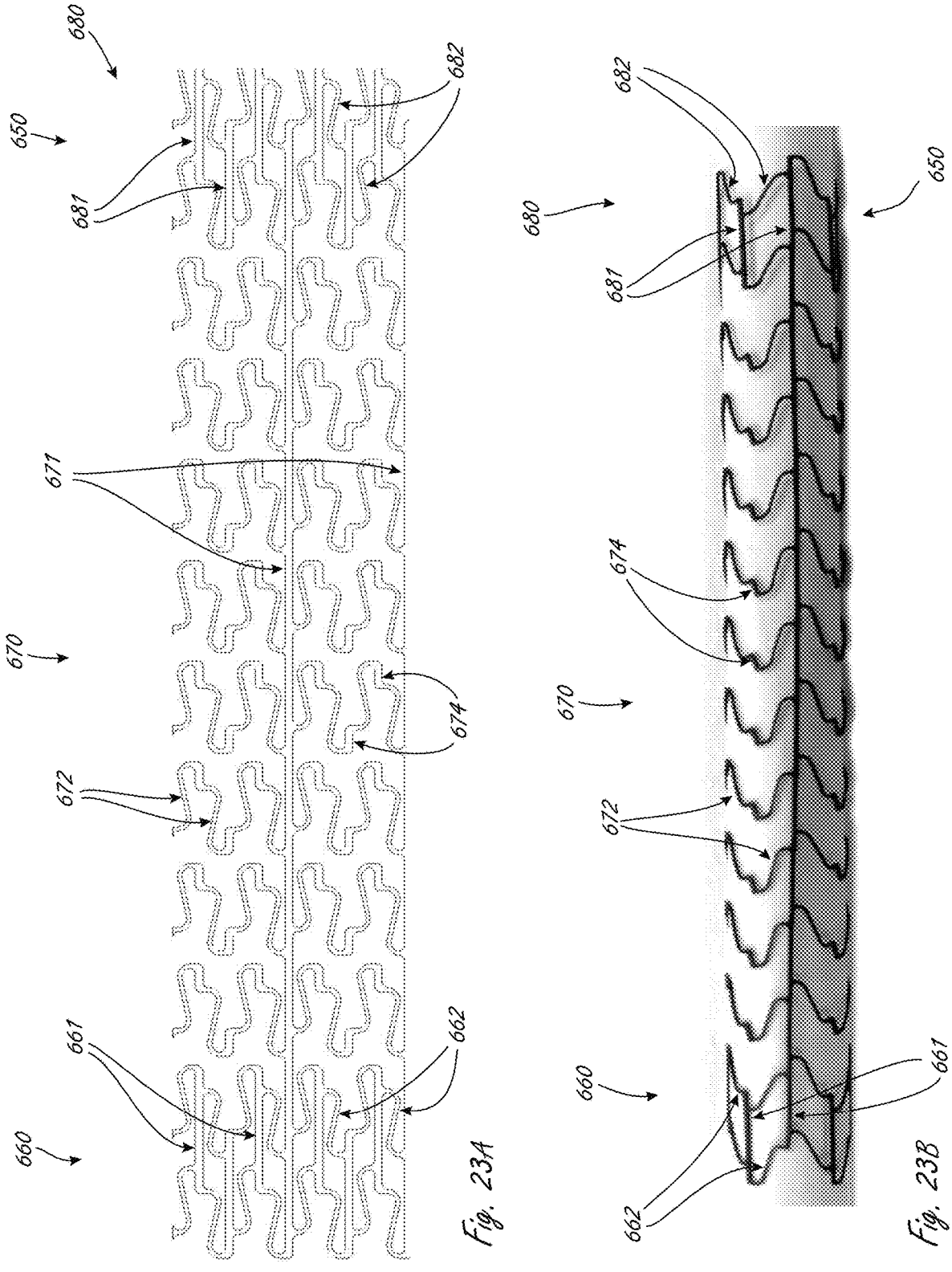

FIG. 23A illustrates an exemplary scaffold in a flattened and non-expanded configuration.

FIG. 23B illustrates the scaffold from FIG. 23A in an expanded configuration.

Figures 24A, 24B:
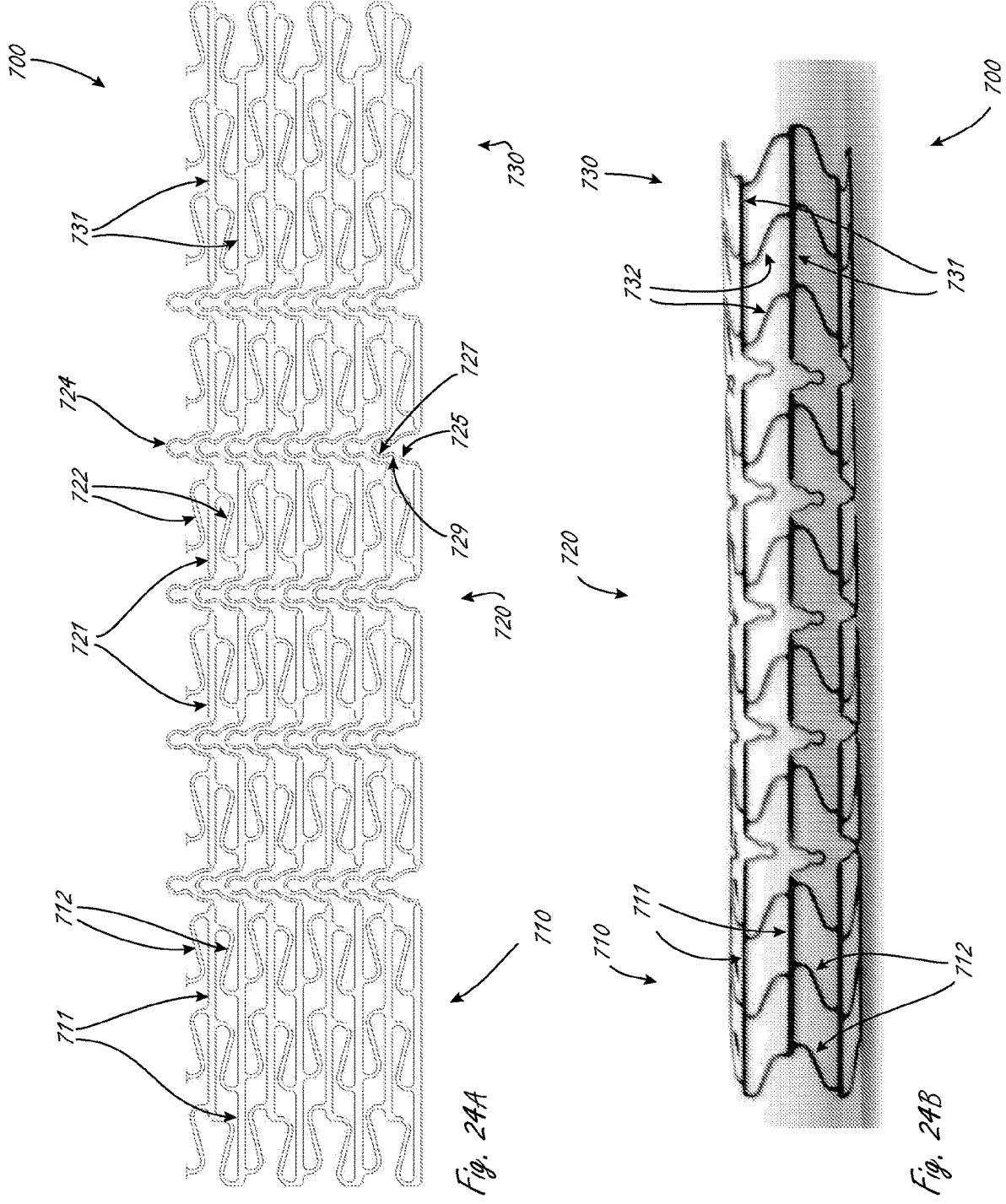

FIG. 24A illustrates an exemplary scaffold in a flattened and non-expanded configuration.

FIG. 24B illustrates the scaffold from FIG. 24A in an expanded configuration.

Figures 25A, 25B:
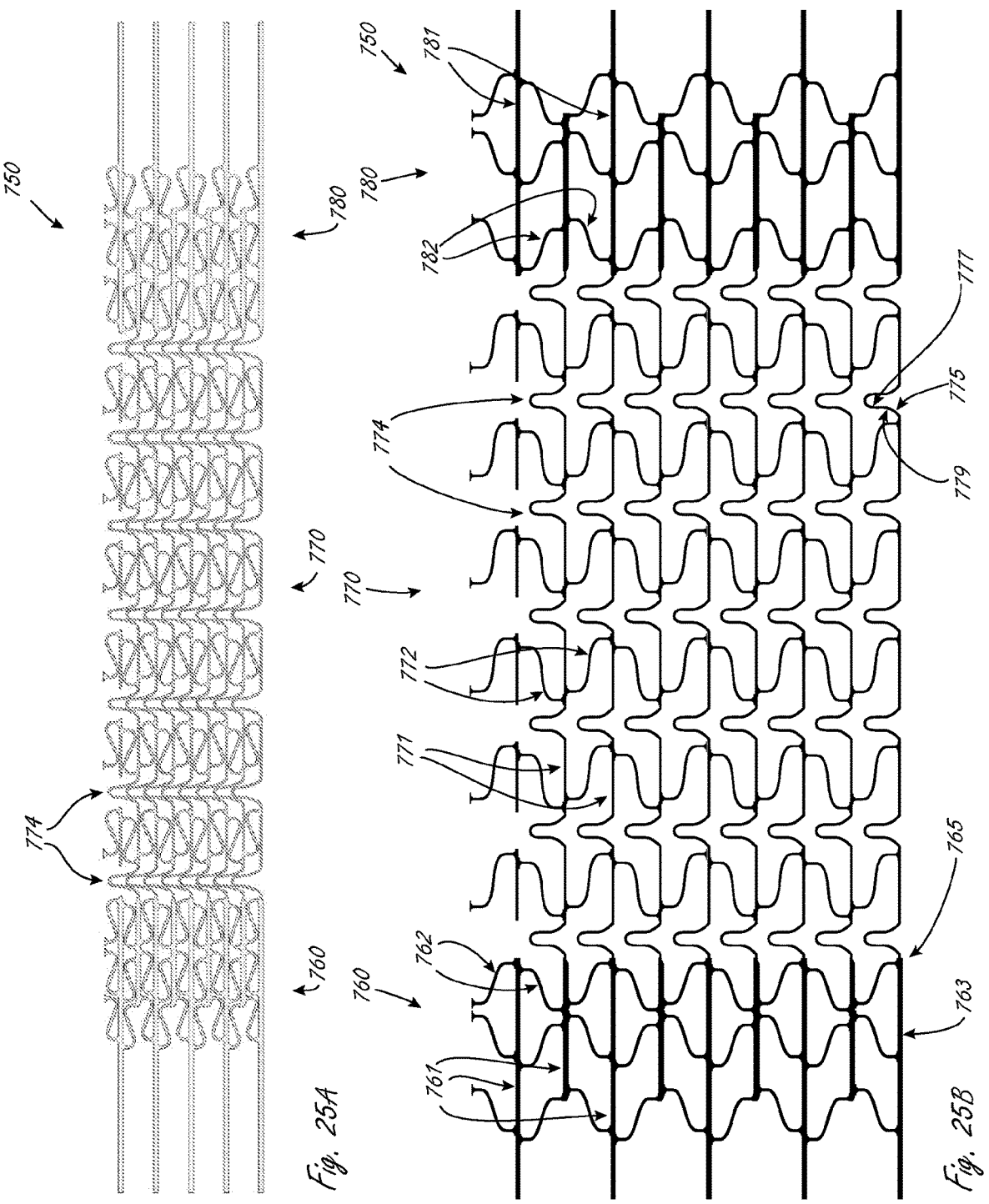

FIG. 25A illustrates an exemplary scaffold in a flattened and non-expanded configuration.

FIG. 25B illustrates the scaffold from FIG. 25A in a flattened expanded configuration.

Figures 26A, 26B:
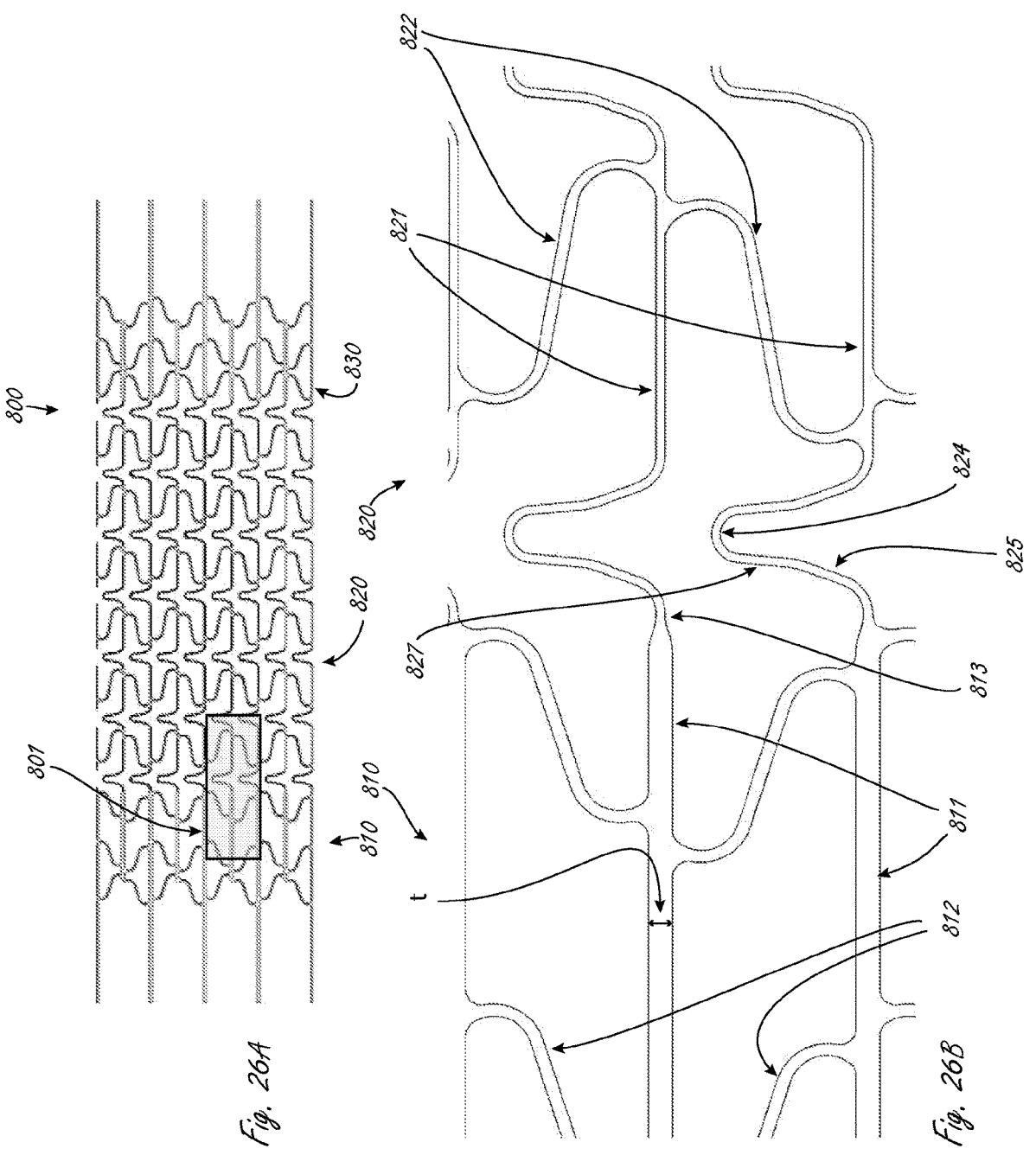

FIG. 26A illustrates an exemplary scaffold in a flattened and non-expanded configuration.

FIG. 26B highlights an exemplary section of the scaffold shown in FIG. 26A.

Figures 27A, 27B:
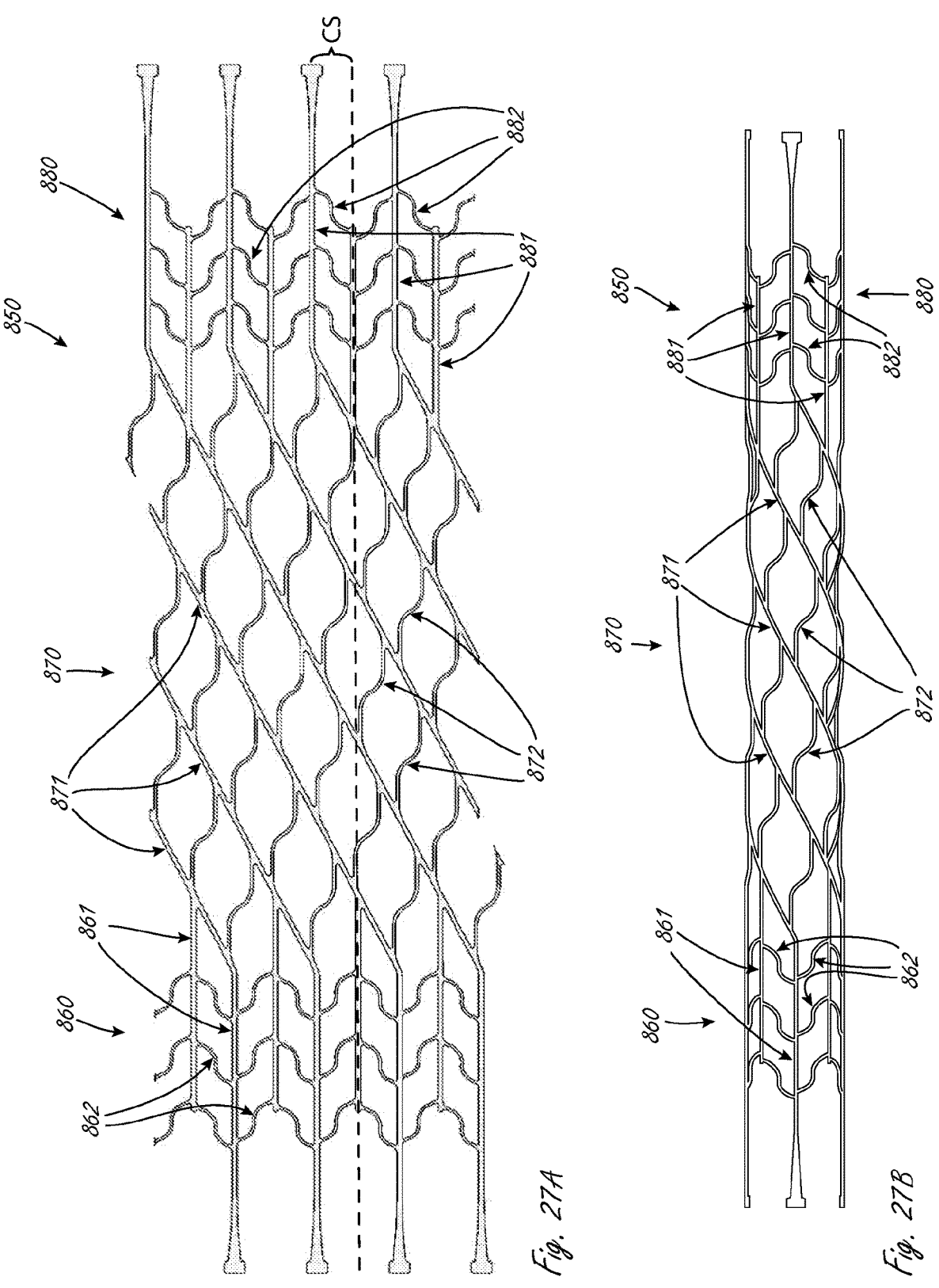

FIG. 27A illustrates an exemplary scaffold in a flattened and non-collapsed configuration.

FIG. 27B illustrates the scaffold from FIG. 27A in a non-collapsed configuration.

Figures 28A, 28B:
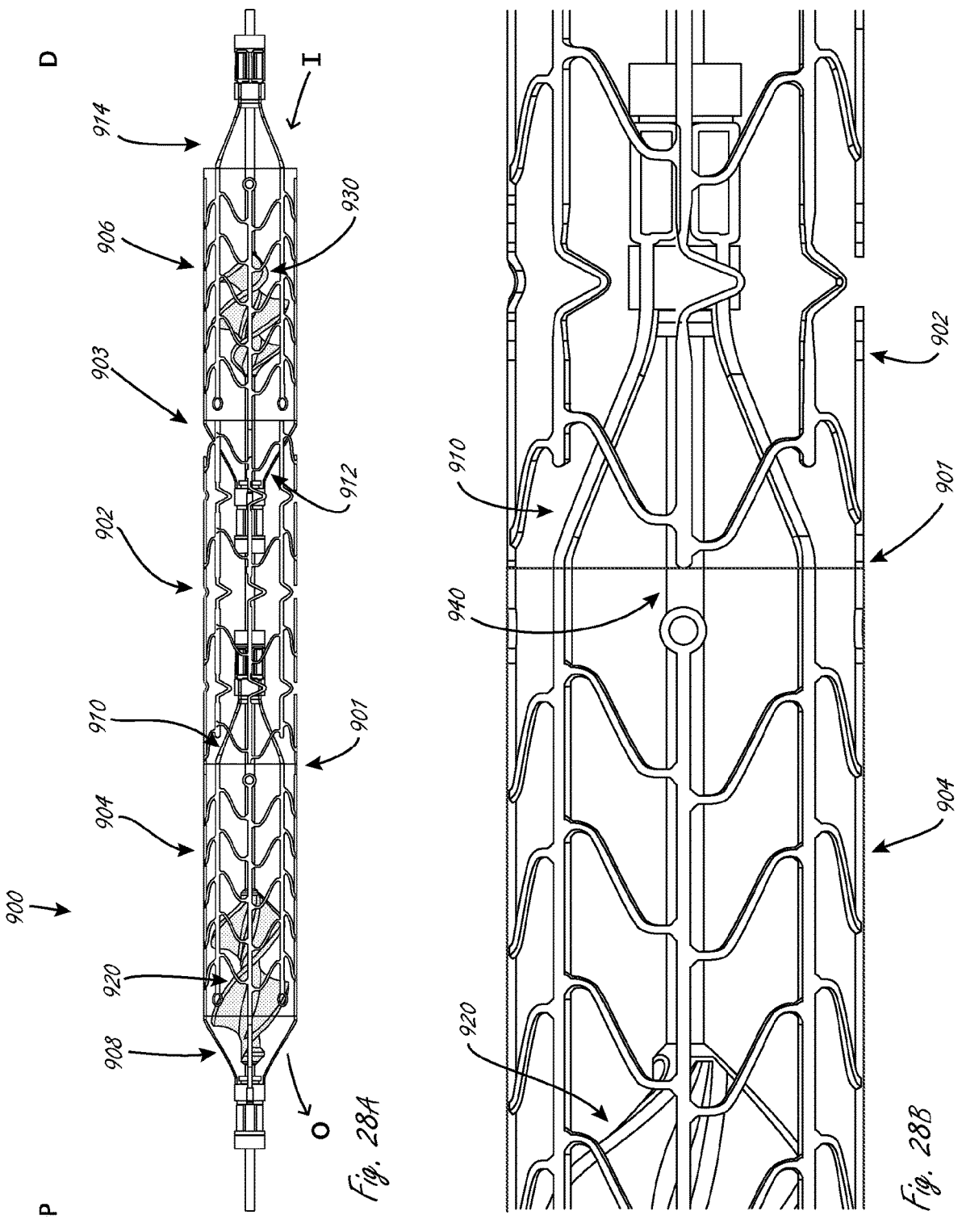

FIGS. 28A and 28B show an exemplary collapsible pump portion that includes a central scaffold section that is not unitary and not coupled to one or more axially adjacent scaffold sections.

Figure 29A:
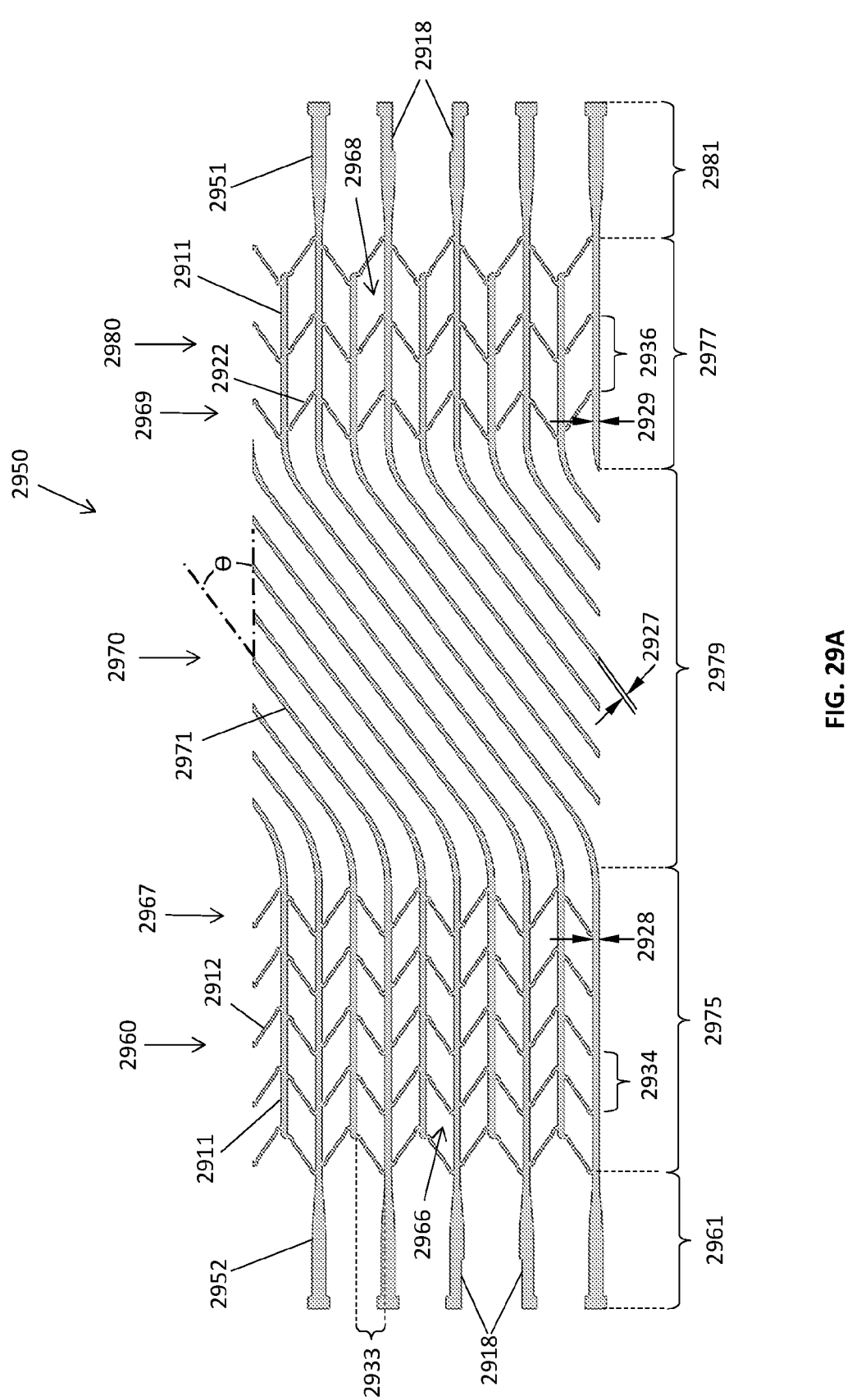
Figure 29B:
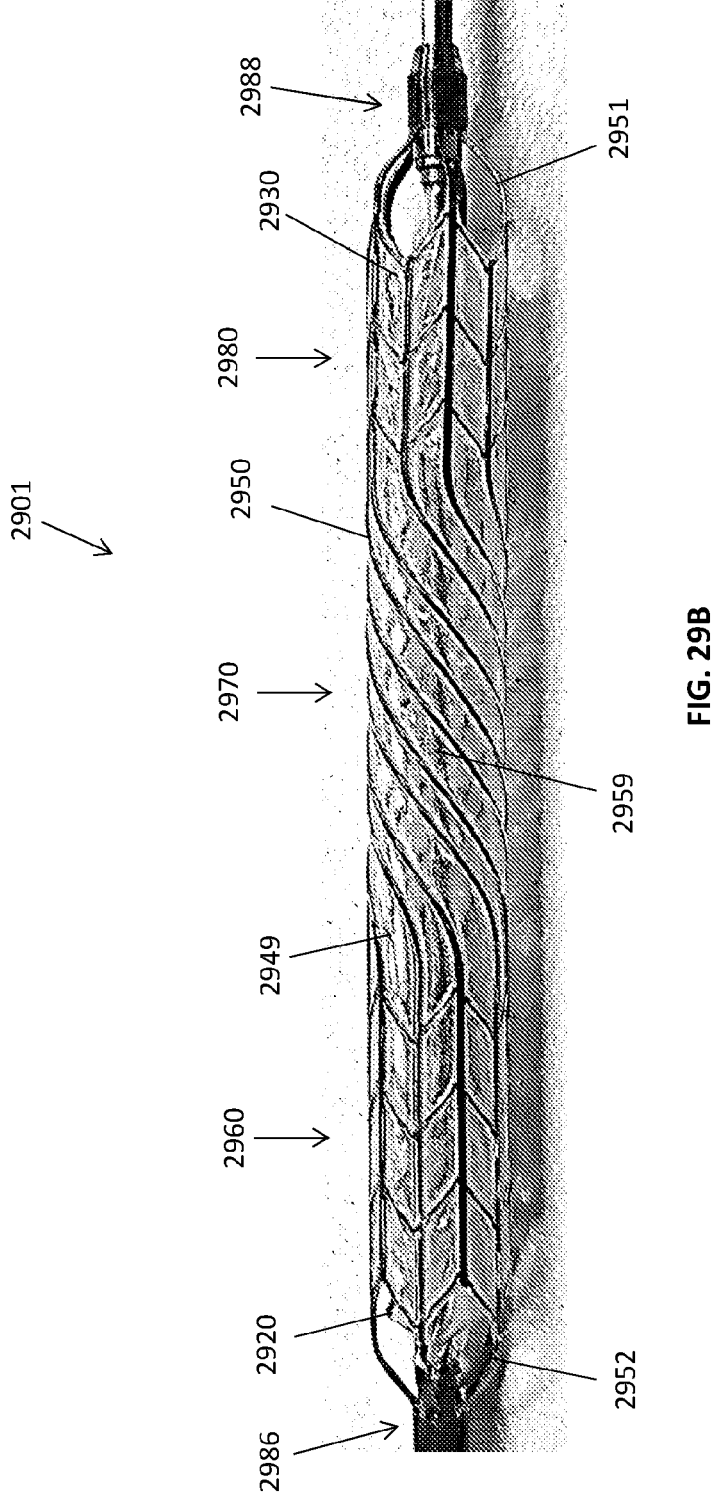
Figure 29C:
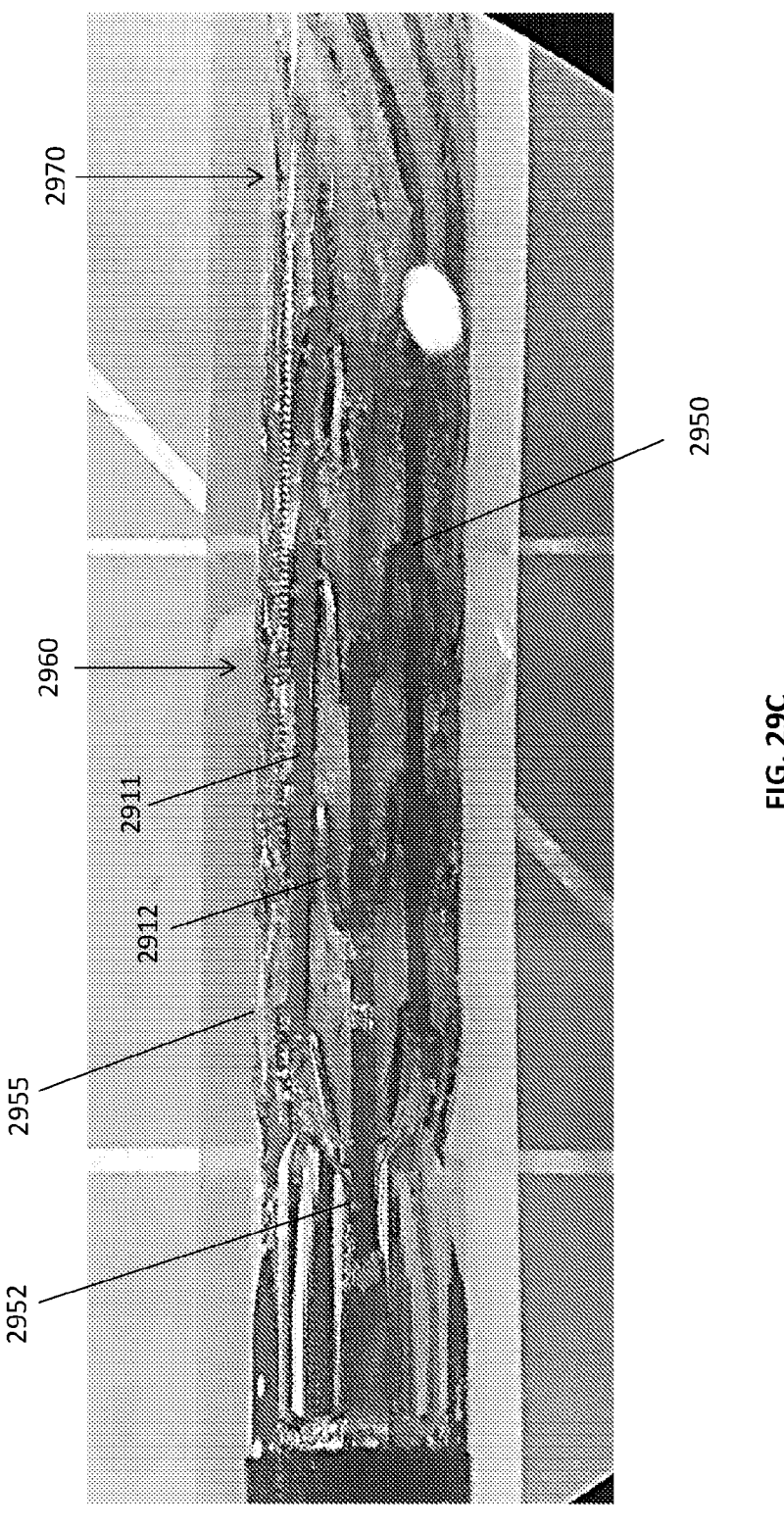

FIGS. 29A-29E show an exemplary scaffold having sections of differing stiffness: FIG. 29A illustrates a flattened view of the scaffold; FIG. 29B illustrates a blood conduit with the scaffold with a membrane in an expanded configuration; FIG. 29C illustrates a proximal impeller region of the

US 12,678,612 B2

Figure 29D:
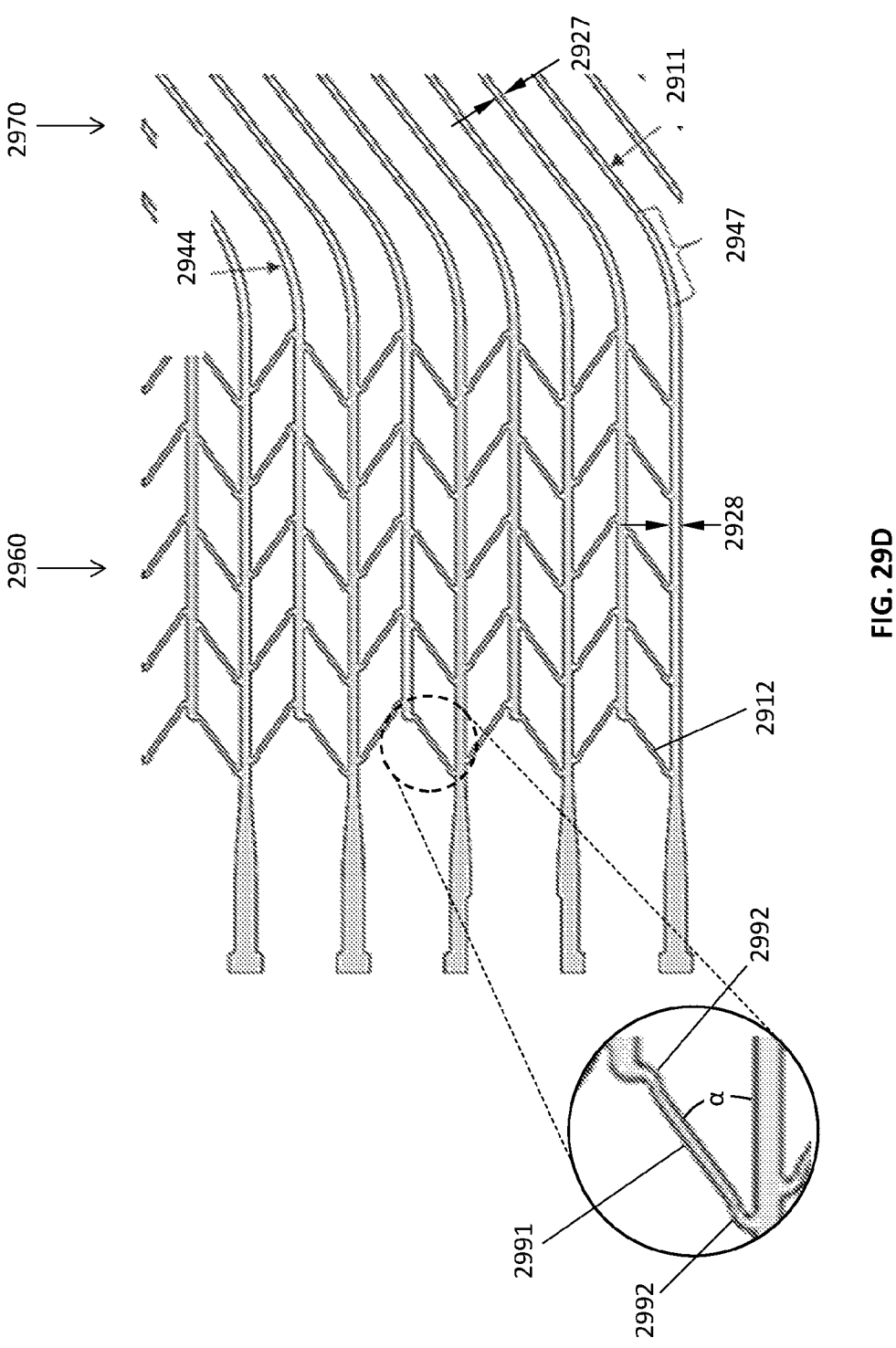
Figure 29E:
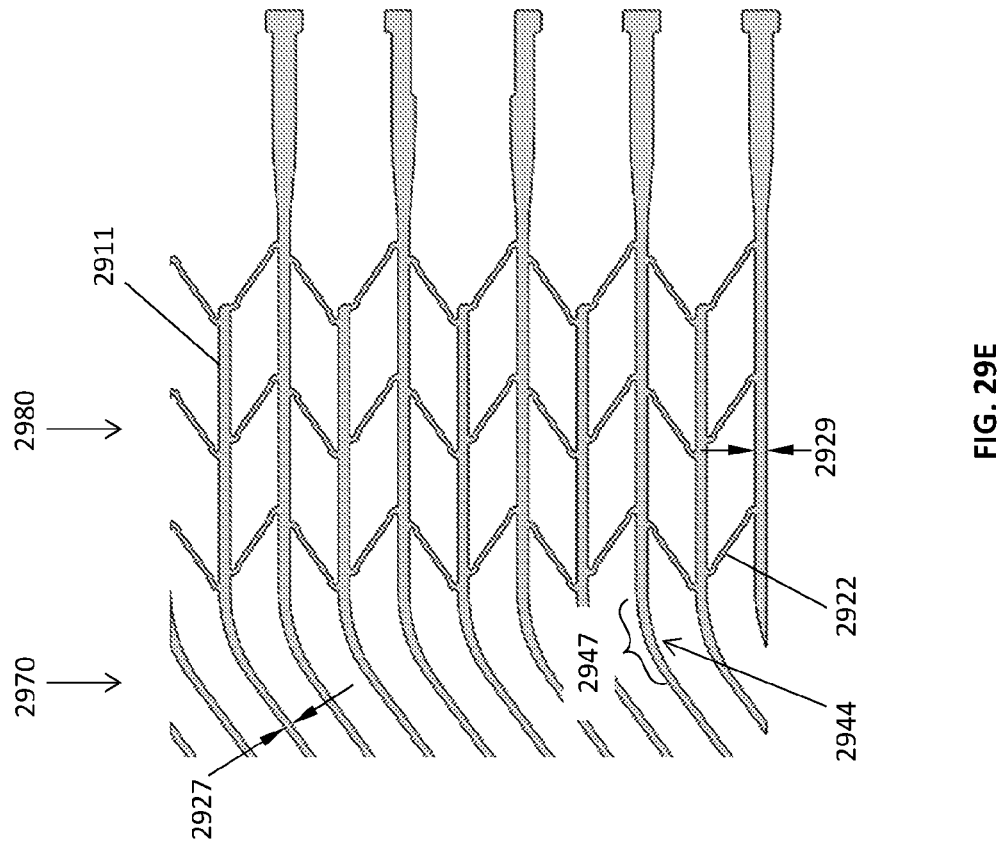

13 blood conduit (including the scaffold and membrane) in a collapsed configuration within a sheath; FIG. 29D illustrates a closeup view of a proximal portion of the scaffold; and FIG. 29E illustrates a closeup view of the distal portion of the scaffold.

Figure 30:
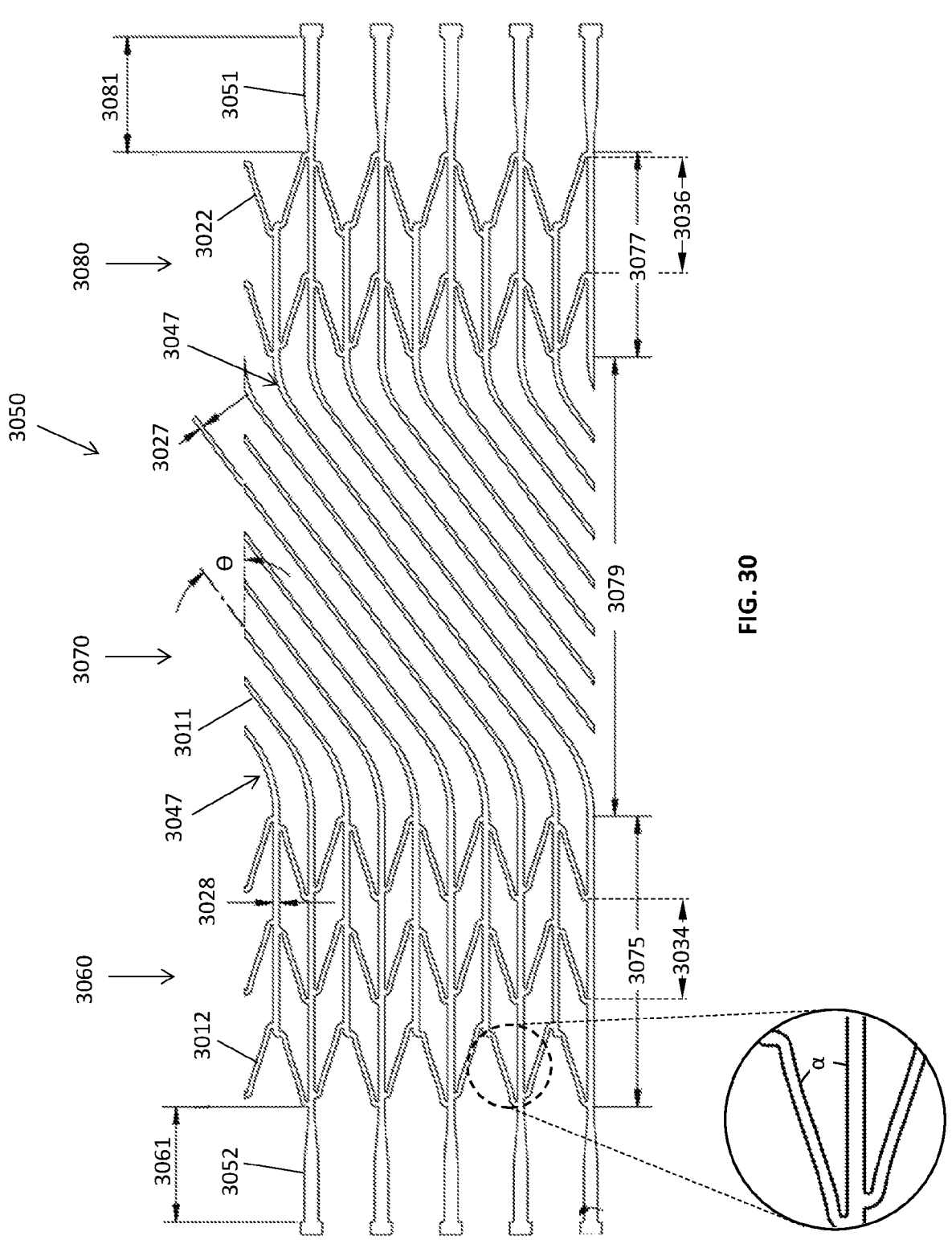

FIG. 30 illustrates a flattened view of another exemplary scaffold having a different scaffold pattern.

Figure 31:
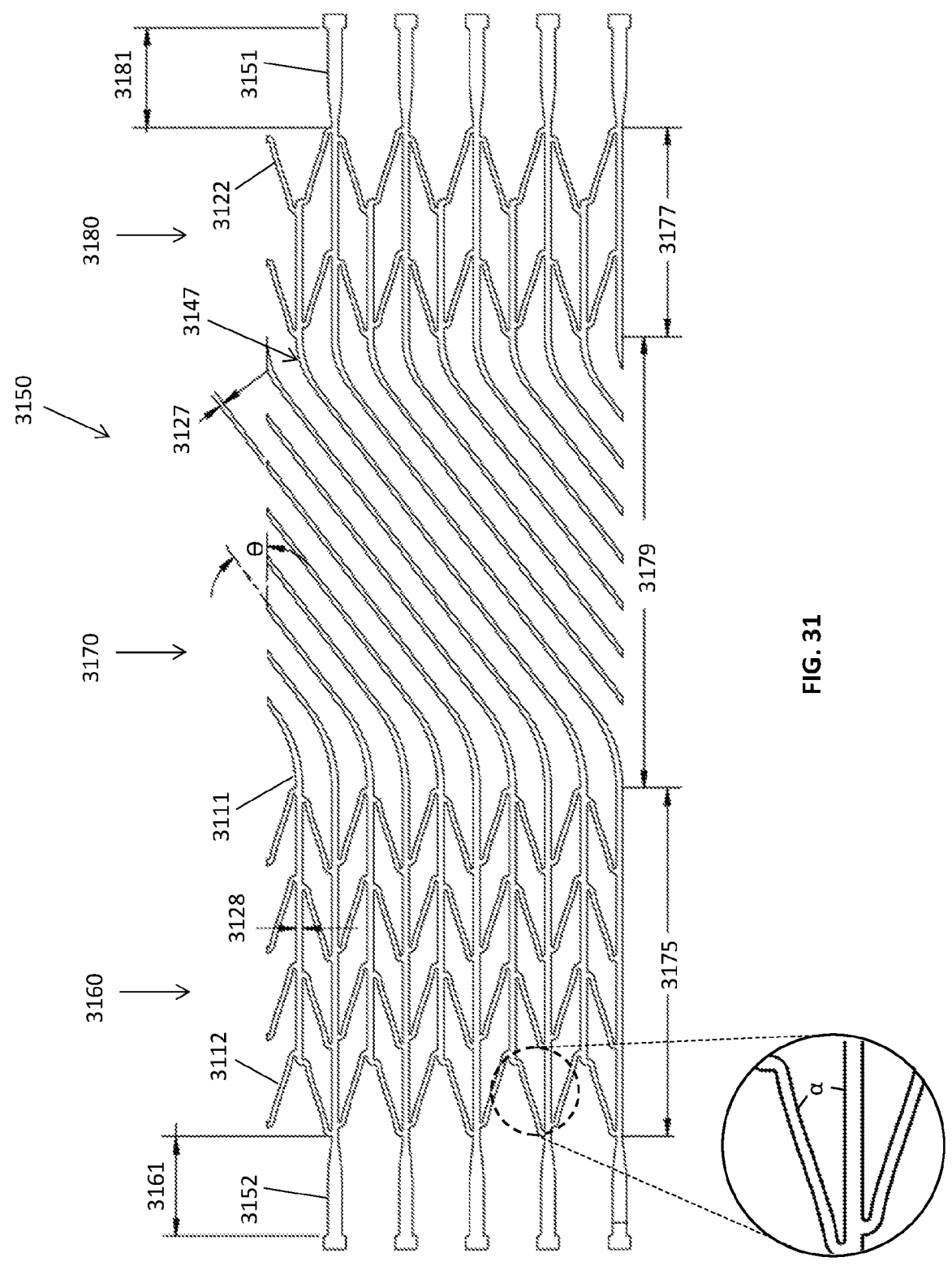

FIG. 31 illustrates a flattened view another exemplary scaffold having a different scaffold pattern.

Figure 32A:
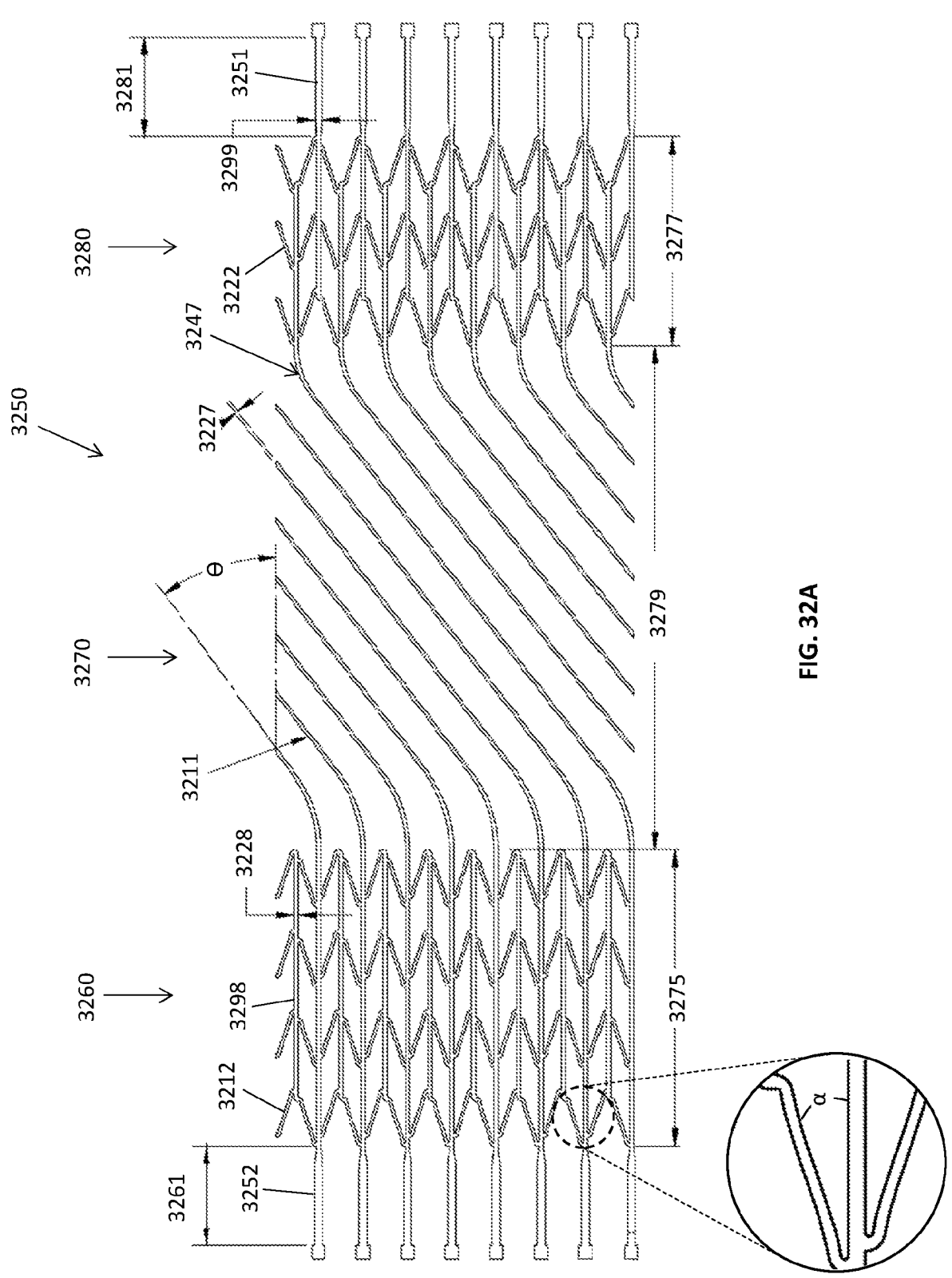
Figure 32B:
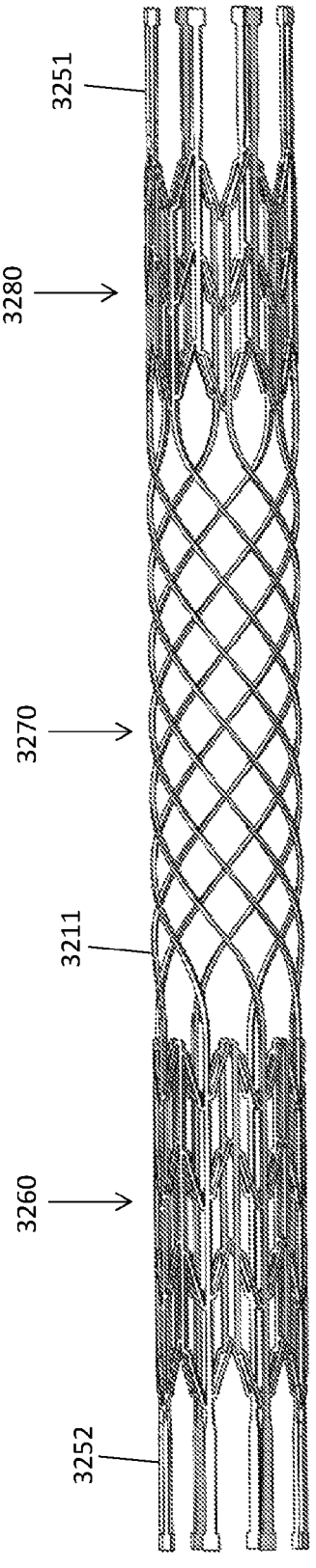

FIGS. 32A and 32B illustrates another exemplary scaffold having a different scaffold pattern: FIG. 32A shows a flattened view of the scaffold; and FIG. 32B shows the scaffold in an expanded state.

Figures 33A, 33B:
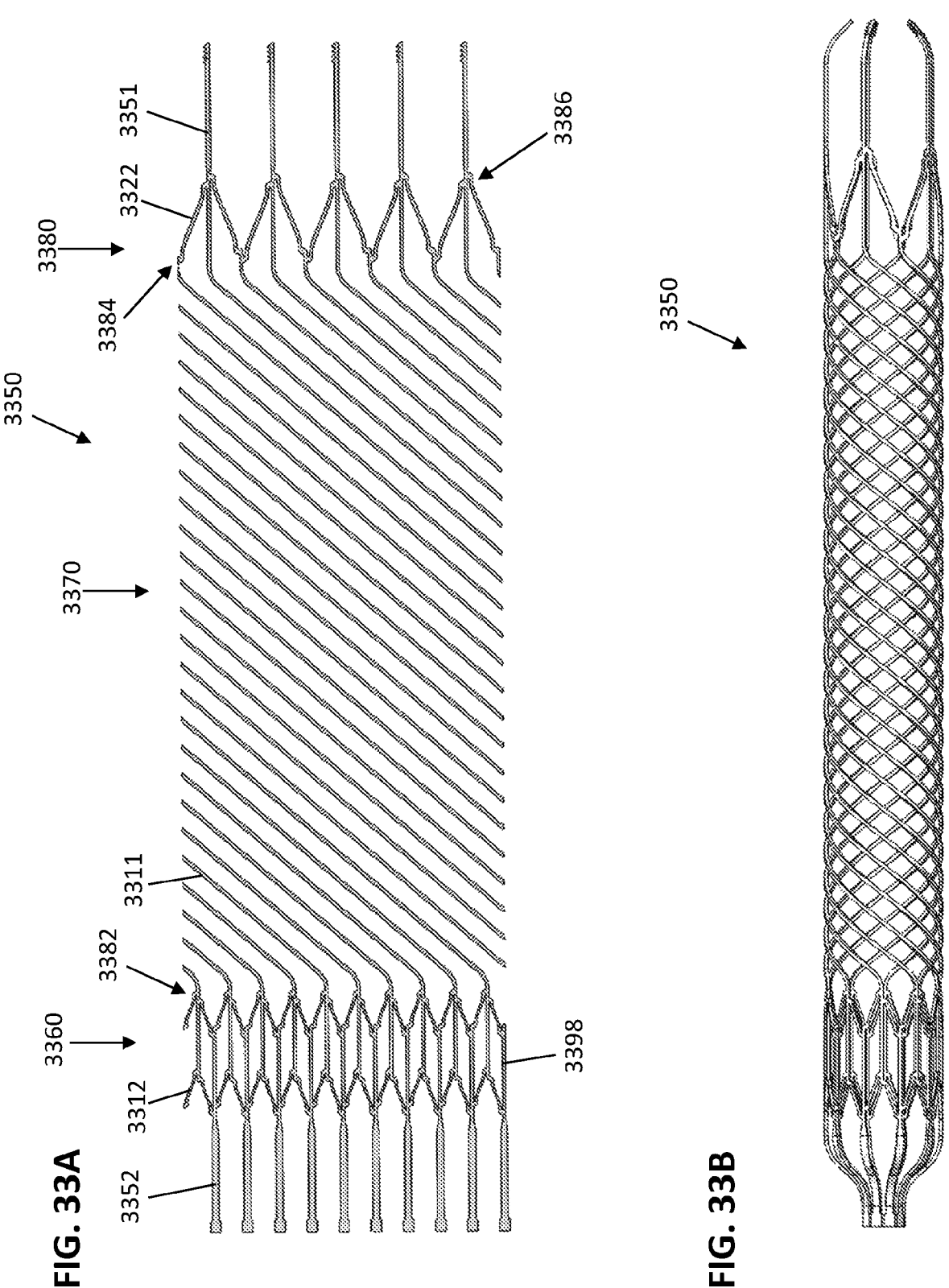

FIGS. 33A-33B show another exemplary scaffold in a flattened view and an expanded state, respectively.

Figure 34:
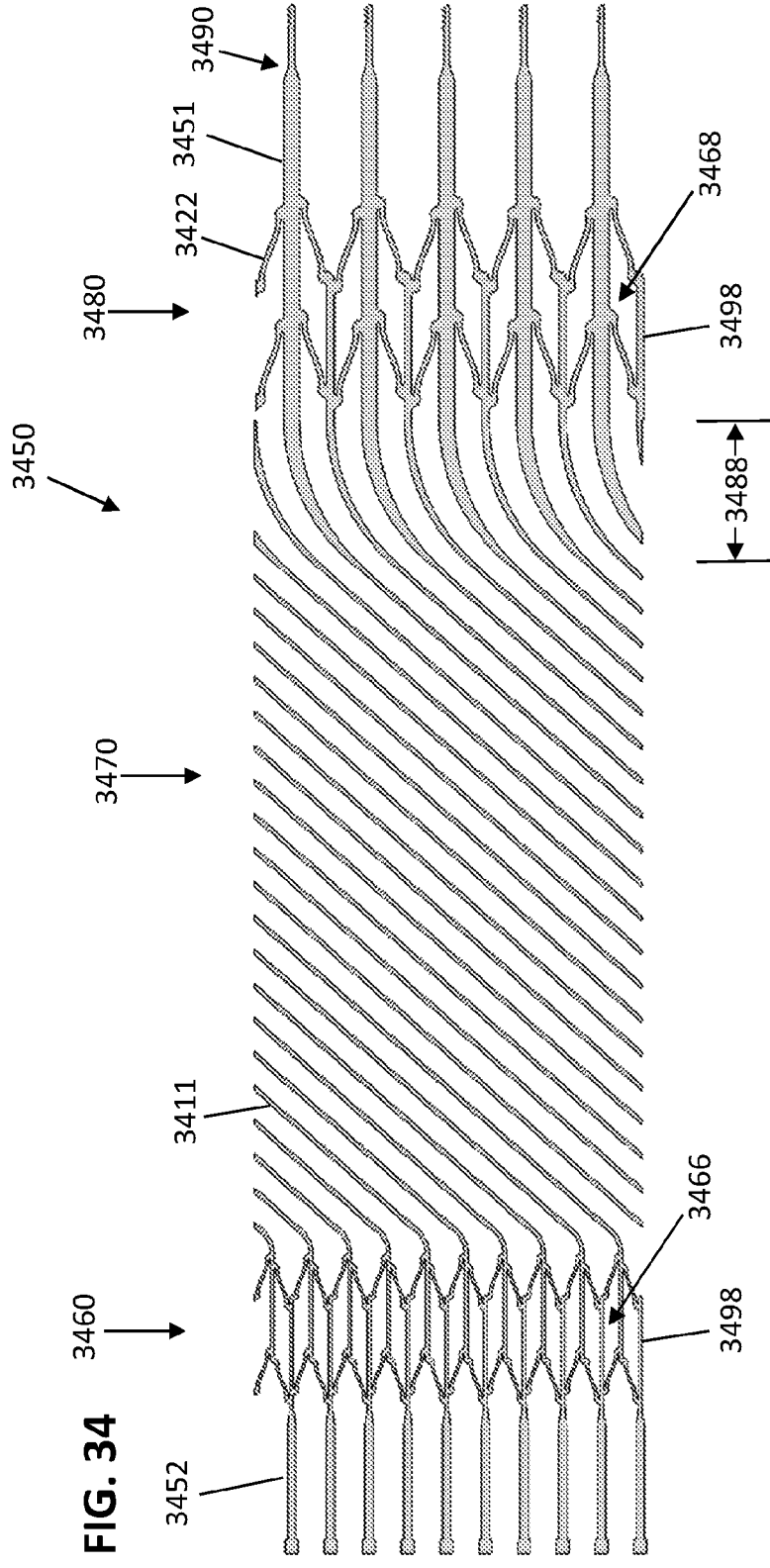

FIG. 34 shows another exemplary scaffold in a flattened view.

DETAILED DESCRIPTION

The present disclosure is related to medical devices, systems, and methods of use and manufacture. Medical devices herein may include a distal pump portion (which may also be referred to herein as a working portion) adapted to be disposed within a physiologic vessel, wherein the distal pump portion includes one or more components that act upon fluid. For example, pump portions herein may include one or more rotating members that when rotated, can facilitate the movement of a fluid such as blood.

Any of the disclosure herein relating to an aspect of a system, device, or method of use can be incorporated with any other suitable disclosure herein. For example, a figure describing only one aspect of a device or method can be included with other embodiments even if that is not specifically stated in a description of one or both parts of the disclosure. It is thus understood that combinations of different portions of this disclosure are included herein.

Figure 1:
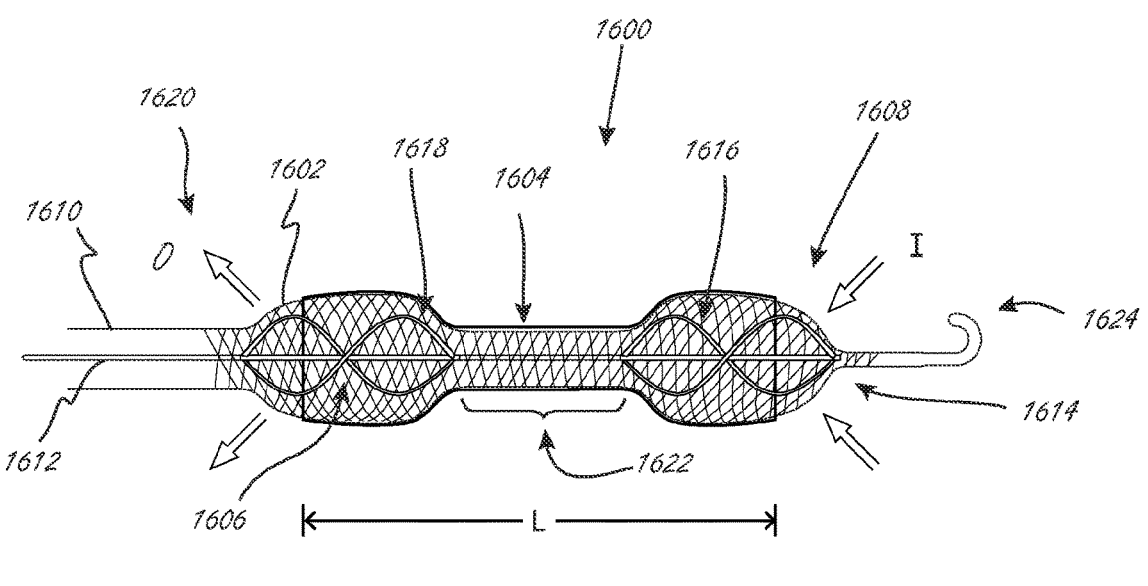
FIG. 1 is a side view of an exemplary expandable pump portion that includes an expandable impeller housing that includes a scaffold and blood conduit, and a plurality of impellers.

FIG. 1 is a side view illustrating a distal portion of an exemplary catheter blood pump, including pump portion 1600, wherein pump portion 1600 includes proximal impeller 1606 and distal impeller 1616, both of which are in operable communication with drive cable 1612 (also referred to as a driveshaft). Pump portion 1600 is in an expanded configuration in FIG. 1, but is adapted to be collapsed to a delivery configuration so that it can be delivered with a lower profile. The impellers can be attached to drive mechanism 1612 (e.g., a drive cable). Drive mechanism 1612 is in operable communication with an external motor, not shown, and extends through elongate shaft 1610. The phrases "pump portion" and "working portion" (or derivatives thereof) may be used herein interchangeably unless indicated to the contrary. For example, without limitation, "pump portion" 1600 can also be referred to herein as a "working portion." Although the embodiment of FIG. 1 shows two impellers (i.e., a distal impeller and a proximal impeller), it should be understood that the embodiment of FIG. 1, or any other embodiment in this disclosure, can include only a single impeller, such as only a proximal impeller or only a distal impeller.

Pump portion 1600 also includes expandable member or expandable scaffold 1602, which in this embodiment has a proximal end 1620 that extends further proximally than a proximal end of proximal impeller 1606, and a distal end 1608 that extends further distally than a distal end 1614 of distal impeller 1616. Expandable members may also be referred to herein as expandable scaffolds or scaffold sections. Expandable scaffold 1602 is disposed radially outside of the impellers along the axial length of the impellers. Expandable scaffold 1602 can be constructed in a manner and made from materials similar to many types of expandable structures that are known in the medical arts to be able to be collapsed and expanded, examples of which are provided herein. Examples of suitable materials include, but are not limited to, polyurethane, polyurethane elastomers, metallic alloys, etc.

Pump portion 1600 also includes blood conduit 1604, which is coupled to and supported by expandable member 1602, has a length L, and extends axially between the impellers. Conduit 1604 creates and provides a fluid lumen between the two impellers. When in use, fluid moves through the lumen defined by conduit 1604. The conduits herein may be non-permeable, or they may be semipermeable, or even porous as long as they still define a lumen. The conduits herein are also flexible, unless otherwise indicated. The conduits herein extend completely around (i.e., 360 degrees) at least a portion of the pump portion. In pump portion 1600, the conduit extends completely around expandable member 1602, but does not extend all the way to the proximal end 1602 or distal end 1608 of expandable member 1602. The structure of the expandable member creates at least one inlet aperture to allow for inflow "I," and at least one outflow aperture to allow for outflow "0." Conduit 1604 improves impeller pumping dynamics, compared to pump portions without a conduit. As described herein, expandable members or scaffolds may also be considered to be a part of the blood conduit generally, which together define a blood lumen. In these instances, the scaffold and material supported by the scaffold may be referred to herein as an expandable impeller housing or housing.

Expandable member 1602 may have a variety of constructions, and made from a variety of materials. For example, expandable member 1602 may be formed similar to expandable stents or stent-like devices, or any other example provided herein. For example, without limitation, expandable member 1602 could have an open-braided construction, such as a 24-end braid, although more or fewer braid wires could be used. Exemplary materials for the expandable member as well as the struts herein include nitinol, cobalt alloys, and polymers, although other materials could be used. Expandable member 1602 has an expanded configuration, as shown, in which the outer dimension (measured orthogonally relative a longitudinal axis of the working portion) of the expandable member is greater in at least a region where it is disposed radially outside of the impellers than in a central region 1622 of the expandable member that extends axially between the impellers. Drive mechanism 1612 is co-axial with the longitudinal axis in this embodiment. In use, the central region can be placed across a valve, such as an aortic valve. In some embodiments, expandable member 1602 is adapted and constructed to expand to an outermost dimension of 12-24F (4.0-8.0 mm) where the impellers are axially within the expandable member, and to an outermost dimension of 10-20F (3.3-6.7 mm) in central region 1622 between the impellers. The smaller central region outer dimension can reduce forces acting on the valve, which can reduce or minimize damage to the valve. The larger dimensions of the expandable member in the regions of the impellers can help stabilize the working portion axially when in use. Expandable member 1602 has a general dumbbell configuration. Expandable member 1602 has an outer configuration that tapers as it transitions from the impeller regions to central region 1622, and again tapers at the distal and proximal ends of expandable member 1602.

Expandable member 1602 has a proximal end 1620 that is coupled to shaft 1610, and a distal end 1608 that is coupled to distal tip 1624. The impellers and drive mechanism 1612 rotate within the expandable member and conduit assembly. Drive mechanism 1612 is axially stabilized with respect to distal tip 1624, but is free to rotate with respect to tip 1624.

In some embodiments, expandable member 1602 can be collapsed by pulling tension from end-to-end on the expandable member. This may include linear motion (such as, for example without limitation, 5-20 mm of travel) to axially extend expandable member 1602 to a collapsed configuration with collapsed outer dimension(s). Expandable member 1602 can also be collapsed by pushing an outer shaft such as a sheath over the expandable member/conduit assembly, causing the expandable member and conduit to collapse towards their collapsed delivery configuration.

Impellers 1606 and 1616 are also adapted and constructed such that one or more blades will stretch or radially compress to a reduced outermost dimension (measured orthogonally to the longitudinal axis of the working portion). For example, without limitation, any of the impellers herein can include one or more blades made from a plastic formulation with spring characteristics, such as any of the impellers described in U.S. Pat. No. 7,393,181, the disclosure of which is incorporated by reference herein for all purposes and can be incorporated into embodiments herein unless this disclosure indicates to the contrary. Alternatively, for example, one or more collapsible impellers can comprise a superelastic wire frame, with polymer or other material that acts as a webbing across the wire frame, such as those described in U.S. Pat. No. 6,533,716, the disclosure of which is incorporated by reference herein for all purposes.

The inflow and/or outflow configurations of working portion 1600 can be mostly axial in nature.

Exemplary sheathing and unsheathing techniques and concepts to collapse and expand medical devices are known, such as, for example, those described and shown in U.S. Pat. No. 7,841,976 or U.S. Pat. No. 8,052,749, the disclosures of which are incorporated by reference herein.

Figure 2:
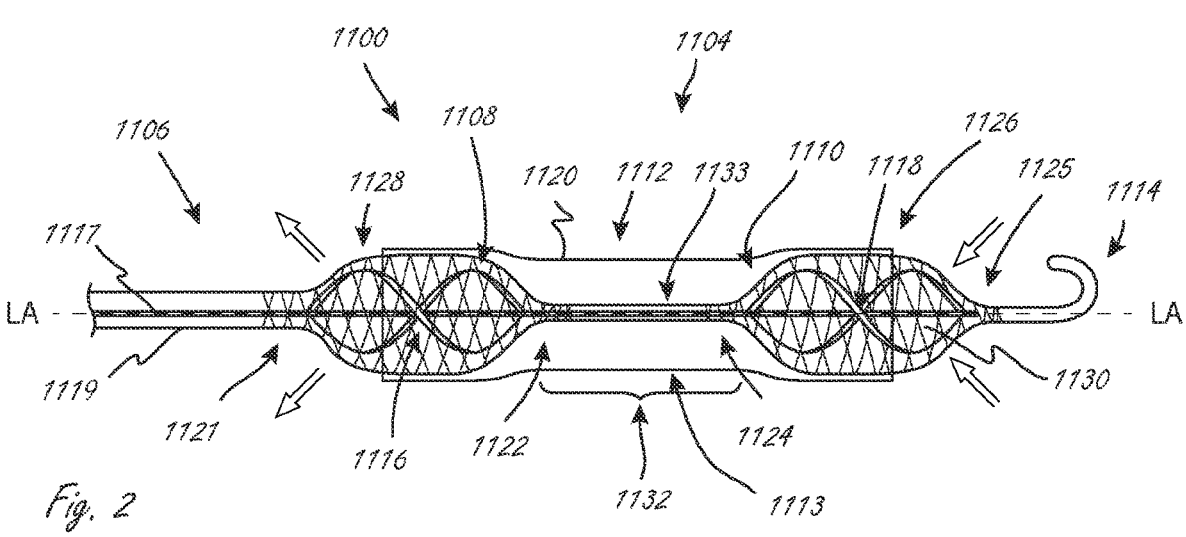
FIG. 2 is a side view of an exemplary expandable pump portion that includes an expandable impeller housing, a blood conduit, a plurality of impellers, and a plurality of expandable scaffolds sections or support members.

FIG. 2 is a side view illustrating a deployed configuration (shown extracorporeally) of a distal portion of an exemplary embodiment of a catheter blood pump. Exemplary blood pump 1100 includes working portion 1104 (which as set forth herein may also be referred to herein as a pump portion) and an elongate portion 1106 extending from working portion 1104. Elongate portion 1106 can extend to a more proximal region of the system, not shown for clarity, and that can include, for example, a motor. Working portion 1104 includes first expandable scaffold or member 1108 and second expandable scaffold or member 1110, axially spaced apart along a longitudinal axis LA of working portion 1104. First scaffold 1108 and second scaffold 1110 (and any other separate scaffolds herein) may also be referenced as part of a common scaffold and referred to herein as scaffold sections. Spaced axially in this context refers to the entire first expandable member being axially spaced from the entire second expandable member along a longitudinal axis LA of working portion 1104. A first end 1122 of first expandable member 1108 is axially spaced from a first end 1124 of second expandable member 1110.

First and second expandable members 1108 and 1110 generally each include a plurality of elongate segments disposed relative to one another to define a plurality of apertures 1130, only one of which is labeled in the second expandable member 1110. The expandable members can have a wide variety of configurations and can be constructed in a wide variety of ways, such as any of the configurations or constructions in, for example without limitation, U.S. Pat. No. 7,841,976, or the tube in U.S. Pat. No. 6,533,716, which is described as a self-expanding metal endoprosthetic material. For example, without limitation, one or both of the expandable members can have a braided construction or can be at least partially formed by laser cutting a tubular element.

Working portion 1104 also includes blood conduit 1112 that is coupled to first expandable member 1108 and to second expandable member 1110, and extends axially in between first expandable member 1108 and second expandable member 1110 in the deployed configuration. A central region 1113 of conduit 1112 spans an axial distance 1132 where the working portion is void of first and second expandable members 1108 and 1110. Central region 1113 can be considered to be axially in between the expandable members. Distal end 1126 of conduit 1112 does not extend as far distally as a distal end 1125 of second expandable member 1110, and proximal end of conduit 1128 does not extend as far proximally as proximal end 1121 of first expandable member 1108.

When the disclosure herein refers to a blood conduit being coupled to an expandable scaffold or member, the term coupled in this context does not require that the conduit be directly attached to the expandable member so that conduit physically contacts the expandable member. Even if not directly attached, however, the term coupled in this context refers to the conduit and the expandable member being joined together such that as the expandable member expands or collapses, the conduit also begins to transition to a different configuration and/or size. Coupled in this context therefore refers to conduits that will move when the expandable member to which it is coupled transitions between expanded and collapsed configurations.

Any of the blood conduits herein can be deformable to some extent. For example, conduit 1112 includes elongate member 1120 that can be made of one or more materials that allow the central region 1113 of conduit to deform to some extent radially inward (towards LA) in response to, for example and when in use, forces from valve tissue (e.g., leaflets) or a replacement valve as working portion 1104 is deployed towards the configuration shown in FIG. 2. The conduit may be stretched tightly between the expandable members in some embodiments. The conduit may alternatively be designed with a looseness that causes a greater degree of compliance. This can be desirable when the working portion is disposed across fragile structures such as an aortic valve, which may allow the valve to compress the conduit in a way that minimizes point stresses in the valve. In some embodiments, the conduit may include a membrane attached to the proximal and distal expandable members. Exemplary materials that can be used for any conduits herein include, without limitations, polyurethane rubber, silicone rubber, acrylic rubber, expanded polytetrafluoroethylene, polyethylene, polyethylene terephthalate, including any combination thereof.

Any of the conduits herein can have a thickness of, for example, 0.5-20 thousandths of an inch (thou), such as 1-15 thou, or 1.5 to 15 thou, 1.5 to 10 thou, or 2 to 10 thou.

Any of the blood conduits herein, or at least a portion of the conduit, can be impermeable to blood. In FIG. 2, working portion 1104 includes a lumen that extends from distal end 1126 of conduit 1112 and extends to proximal end 1128 of conduit 1112. The lumen is defined by conduit 1112 in central region 1113, but can be thought of being defined by both the conduit and portions of the expandable members in regions axially adjacent to central region 1113. In this embodiment, however, it is the conduit material that causes the lumen to exist and prevents blood from passing through the conduit.

Any of the conduits herein that are secured to one or more expandable members can be, unless indicated to the contrary, secured so that the conduit is disposed radially outside of one or more expandable members, radially inside of one or more expandable members, or both, and the expandable member can be impregnated with the conduit material.

The proximal and distal expandable scaffolds or members help maintain the blood conduit in an open configuration to create the lumen, while each also creates a working environment for an impeller, described below. Each of the expandable scaffolds, when in the deployed configuration, is maintained in a spaced relationship relative to a respective impeller, which allows the impeller to rotate within the expandable member without contacting the expandable member. Working portion 1104 includes first impeller 1116 and second impeller 1118, with first impeller 1116 disposed radially within first expandable member 1108 and second impeller 1118 disposed radially within second expandable member 1110. In this embodiment, the two impellers even though they are distinct and separate impellers, are in operable communication with a common drive mechanism (e.g., drive cable 1117), such that when the drive mechanism is activated the two impellers rotate together. In this deployed configuration, impellers 1116 and 1118 are axially spaced apart along longitudinal axis LA, just as are the expandable members 1108 and 1110 are axially spaced apart. Although the embodiment of FIG. 2 shows two impellers (i.e., a distal impeller and a proximal impeller), it should be understood that the embodiment of FIG. 2, or any other embodiment in this disclosure, can include only a single impeller, such as only a proximal impeller or only a distal impeller.

Impellers 1116 and 1118 are also axially within the ends of expandable members 1108 and 1110, respectively (in addition to being radially within expandable members 1108 and 1110). The impellers herein can be considered to be axially within an expandable member even if the expandable member includes struts extending from a central region of the expandable member towards a longitudinal axis of the working portion (e.g., tapering struts in a side view). In FIG. 2, second expandable member 1110 extends from first end 1124 (proximal end) to second end 1125 (distal end).

In FIG. 2, a distal portion of impeller 1118 extends distally beyond distal end 1126 of conduit 1112, and a proximal portion of impeller 1116 extends proximally beyond proximal end 1128 of conduit 1112. In this figure, portions of each impeller are axially within the conduit in this deployed configuration.

In the exemplary embodiment shown in FIG. 2, impellers 1116 and 1118 are in operable communication with a common drive mechanism 1117, and in this embodiment, the impellers are each coupled to drive mechanism 1117, which extends through shaft 1119 and working portion 1104. Drive mechanism 1117 can be, for example, an elongate drive cable, which when rotated causes the impellers to rotate. In this example, as shown, drive mechanism 1117 extends to and is axially fixed relative to distal tip 1114, although it is adapted to rotate relative to distal tip 1114 when actuated. Thus, in this embodiment, the impellers and drive mechanism 1117 rotate together when the drive mechanism is rotated. Any number of known mechanisms can be used to rotate drive mechanism, such as with a motor (e.g., an external motor).

The expandable members and the conduit are not in rotational operable communication with the impellers and the drive mechanism. In this embodiment, proximal end 1121 of proximal expandable member 1108 is coupled to shaft 1119, which may be a shaft of elongate portion 1106 (e.g., an outer catheter shaft). Distal end 1122 of proximal expandable member 1108 is coupled to central tubular member 1133, through which drive mechanism 1117 extends. Central tubular member 1133 extends distally from proximal expandable member 1108 within conduit 1112 and is also coupled to proximal end 1124 of distal expandable member 1110. Drive mechanism 1117 thus rotates within and relative to central tubular member 1133. Central tubular member 1133 extends axially from proximal expandable member 1108 to distal expandable member 1110. Distal end 1125 of distal expandable member 1110 is coupled to distal tip 1114, as shown. Drive mechanism 1117 is adapted to rotate relative to tip 1114, but is axially fixed relative to tip 1114.

Working portion 1104 is adapted and configured to be collapsed to a smaller profile than its deployed configuration (which is shown in FIG. 2). This allows it to be delivered using a lower profile delivery device (smaller French size) than would be required if none of working portion 1104 was collapsible. Even if not specifically stated herein, any of the expandable members and impellers may be adapted and configured to be collapsible to some extent to a smaller delivery configuration.

The working portions herein can be collapsed to a collapsed delivery configuration using conventional techniques, such as with an outer sheath that is movable relative to the working portion (e.g., by axially moving one or both of the sheath and working portion). For example, without limitation, any of the systems, devices, or methods shown in the following references may be used to facilitate the collapse of a working portions herein: U.S. Pat. No. 7,841, 976 or U.S. Pat. No. 8,052,749, the disclosures of which are incorporated by reference herein for all purposes.

Figures 3A, 3B:
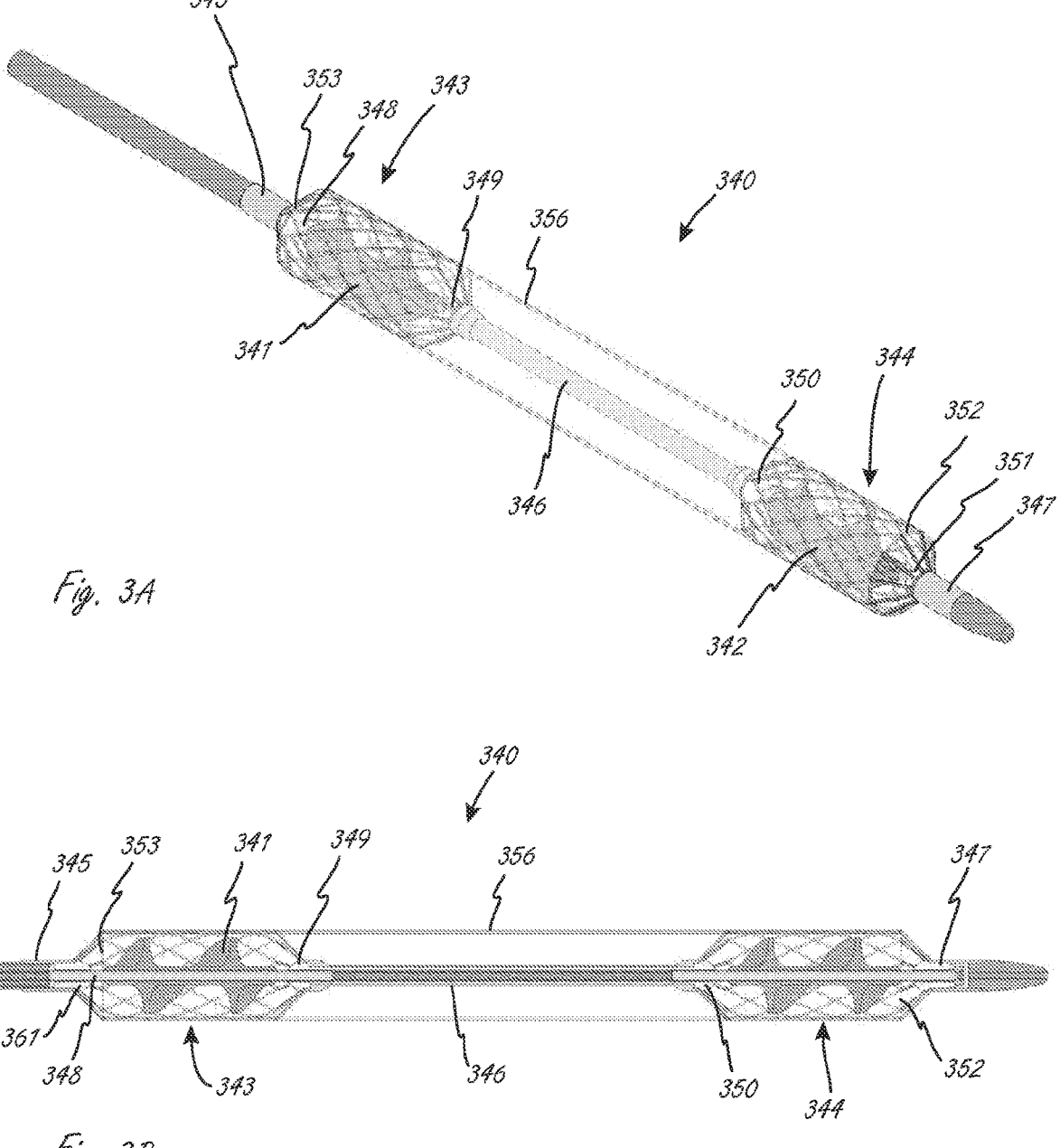
FIGS. 3A, 3B, 3C and 3D illustrate an exemplary expandable pump portion that includes a blood conduit, a plurality of impellers, and a plurality of expandable scaffold sections or support members.
Figure 3C:
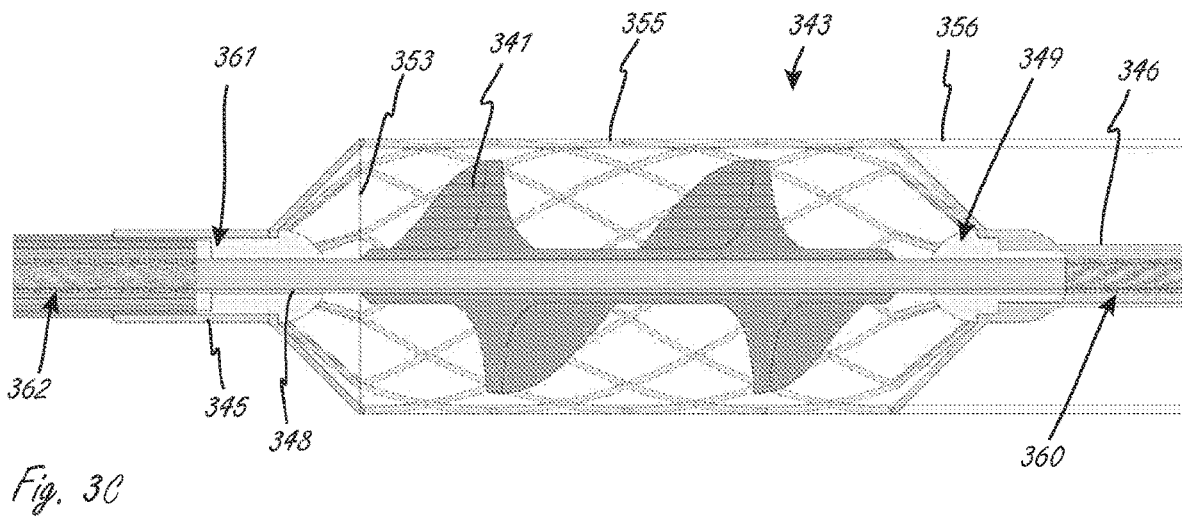
Figure 3D:
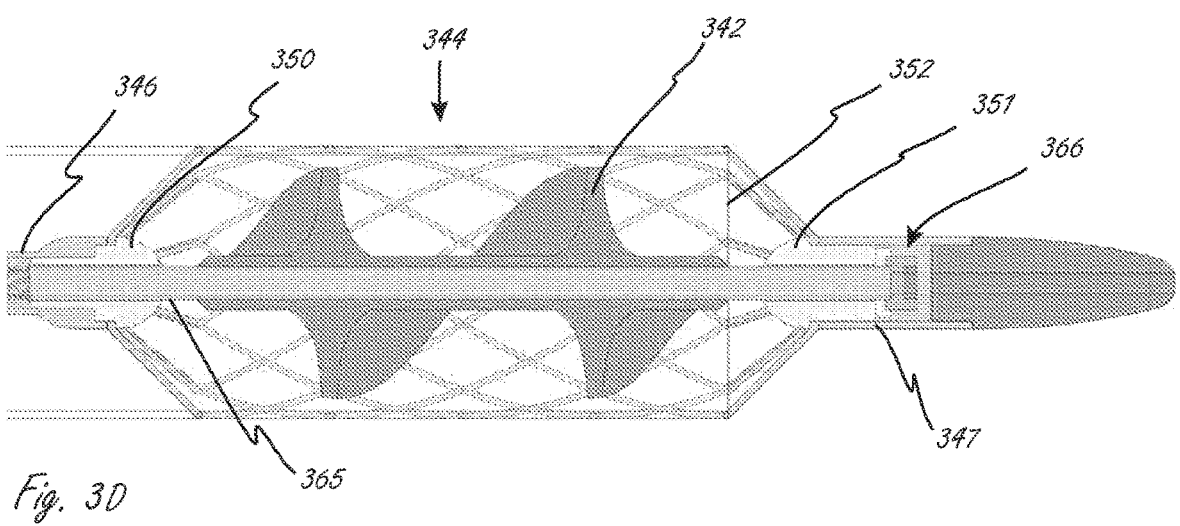

FIGS. 3A-3D show an exemplary pump portion that is similar in some ways to the pump portion shown in FIG. 2. Pump portion 340 is similar to pump portion 1104 in that in includes two expandable members axially spaced from one another when the pump portion is expanded, and a conduit extending between the two expandable members. FIG. 3A is a perspective view, FIG. 3B is a side sectional view, and FIGS. 3C and 3D are close-up side sectional views of sections of the view in FIG. 3B.

Pump portion 340 includes proximal impeller 341 and distal impeller 342, which are coupled to and in operational communication with a drive cable, which defines therein a lumen. The lumen can be sized to accommodate a guidewire, which can be used for delivery of the working portion to the desired location. The drive cable, in this embodiment, includes first section 362 (e.g., wound material), second section 348 (e.g., tubular member) to which proximal impeller 341 is coupled, third section 360 (e.g., wound material), and fourth section 365 (e.g., tubular material) to which distal impeller 342 is coupled. The drive cable sections all have the same inner diameter, so that lumen has a constant inner diameter. The drive cable sections can be secured to each other using known attachment techniques. A distal end of fourth section 365 extends to a distal region of the working portion, allowing the working portion to be, for example, advanced over a guidewire for positioning the working portion. In this embodiment the second and fourth sections can be stiffer than first and third sections. For example, second and fourth can be tubular and first and third sections can be wound material to impart less stiffness.

Pump portion 340 includes proximal expandable scaffold 343 and distal expandable scaffold 344, each of which extends radially outside of one of the impellers. The expandable scaffolds have distal and proximal ends that also extend axially beyond distal and proximal ends of the impellers, which can be seen in FIGS. 3B-3D. Coupled to the two expandable scaffolds is blood conduit 356, which has a proximal end 353 and a distal end 352. The two expandable scaffolds each include a plurality of proximal struts and a plurality of distal struts. The proximal struts in proximal expandable scaffold 343 extend to and are secured to shaft section 345, which is coupled to bearing 361, through which the drive cable extends and is configured and sized to rotate. The distal struts of proximal expandable scaffold 343 extend to and are secured to a proximal region (to a proximal end in this case) of central tubular member 346, which is disposed axially in between the expandable members. The proximal end of central tubular member 346 is coupled to bearing 349, as shown in FIG. 3C, through which the drive cable extends and rotates. The proximal struts extend axially from distal expandable scaffold 344 to and are secured to a distal region (to a distal end in this case) of central tubular member 346. Bearing 350 is also coupled to the distal region of central tubular member 346, as is shown in FIG. 3D. The drive cable extends through and rotates relative to bearing 350. Distal struts extend from the distal expandable scaffold extend to and are secured to shaft section 347 (see FIG. 3A), which can be considered part of the distal tip. Shaft section 347 is coupled to bearing 351 (see FIG. 3D), through which the drive cable extends and rotates relative to. The distal tip also includes bearing 366 (see FIG. 3D), which can be a thrust bearing. Working portion 340 can be similar to or the same in some aspects to working portion 1104, even if not explicitly included in the description. In this embodiment, conduit 356 extends at least as far as ends of the impeller, unlike in working portion 1104. Either embodiment can be modified so that the conduit extends to a position as set forth in the other embodiment. In some embodiments, section 360 can be a tubular section instead of wound.

In alternative embodiments, at least a portion of any of the impellers herein may extend outside of the fluid lumen. For example, only a portion of an impeller may extend beyond an end of the fluid lumen in either the proximal or distal direction. In some embodiments, a portion of an impeller that extends outside of the fluid lumen is a proximal portion of the impeller, and includes a proximal end (e.g., see the proximal impeller in FIG. 2). In some embodiments, the portion of the impeller that extends outside of the fluid lumen is a distal portion of the impeller, and includes a distal end (e.g., see the distal impeller in FIG. 2). When the disclosure herein refers to impellers that extend outside of the fluid lumen (or beyond an end), it is meant to refer to relative axial positions of the components, which can be most easily seen in side views or top views, such as in FIG. 2.

A second impeller at another end of the fluid lumen may not, however, extend beyond the fluid lumen. For example, an illustrative alternative design can include a proximal impeller that extends proximally beyond a proximal end of the fluid lumen (like the proximal impeller in FIG. 2), and the fluid lumen does not extend distally beyond a distal end of a distal impeller (like in FIG. 3B). Alternatively, a distal end of a distal impeller can extend distally beyond a distal end of the fluid lumen, but a proximal end of a proximal impeller does not extend proximally beyond a proximal end of the fluid lumen. In any of the pump portions herein, none of the impellers may extend beyond ends of the fluid lumen. Although the embodiment of FIGS. 3A-3D shows two impellers (i.e., a distal impeller and a proximal impeller), it should be understood that this or any other embodiment in this disclosure can include only a single impeller, such as only a proximal impeller or only a distal impeller.

While specific exemplary locations may be shown herein, the fluid pumps may be able to be used in a variety of locations within a body. Some exemplary locations for placement include placement in the vicinity of an aortic valve or pulmonary valve, such as spanning the valve and positioned on one or both sides of the valve, and in the case of an aortic valve, optionally including a portion positioned in the ascending aorta. In some other embodiments, for example, the pumps may be, in use, positioned further downstream, such as being disposed in a descending aorta.

Figure 4:
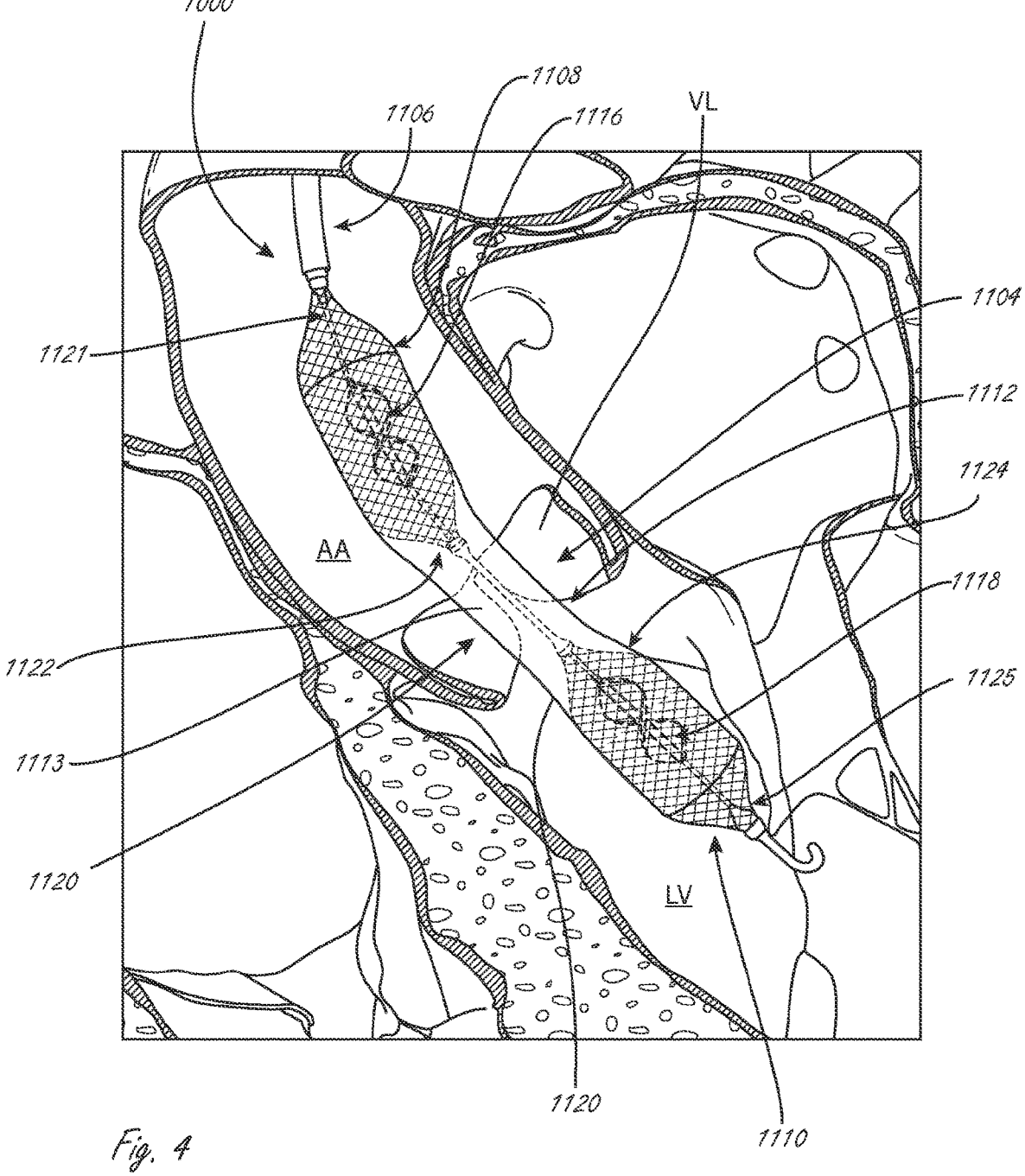
FIG. 4 illustrates an exemplary target location of an expandable pump portion, the pump portion including a blood conduit, a plurality of expandable scaffold sections or support members, and a plurality of impellers.

FIG. 4 illustrates an exemplary placement of pump portion 1104 from catheter blood pump 1000 from FIG. 2. One difference shown in FIG. 4 is that the conduit extends at least as far as the ends of the impellers, like in FIGS. 3A-3D. FIG. 4 shows pump portion 1104 in a deployed configuration, positioned in place across an aortic valve. Pump portion 1104 can be delivered as shown via, for example without limitation, femoral artery access (a known access procedure). While not shown for clarity, system 1000 can also include an outer sheath or shaft in which working portion 1104 is disposed during delivery to a location near an aortic valve. The sheath or shaft can be moved proximally (towards the ascending aorta "AA" and away from left ventricle "LV") to allow for deployment and expansion of working portion 1104. For example, the sheath can be withdrawn to allow for expansion of second expandable scaffold 1110, with continued proximal movement allowing first expandable scaffold 1108 to expand.

In this embodiment, second expandable scaffold 1110 has been expanded and positioned in a deployed configuration such that distal end 1125 is in the left ventricle "LV," and distal to aortic valve leaflets "VL," as well as distal to the annulus. Proximal end 1124 has also been positioned distal to leaflets VL, but in some methods proximal end 1124 may extend slightly axially within the leaflets VL. This embodiment is an example of a method in which at least half of the second expandable member 1110 is within the left ventricle, as measured along its length (measured along the longitudinal axis). And as shown, this is also an example of a method in which the entire second expandable member 1110 is within the left ventricle. This is also an example of a method in which at least half of second impeller 1118 is positioned within the left ventricle, and also an embodiment in which the entire second impeller 1118 is positioned within the left ventricle.

Continued retraction of an outer shaft or sheath (and/or distal movement of working end 1104 relative to an outer sheath or shaft) continues to release conduit 1112, until central region 1113 is released and deployed. The expansion of expandable scaffolds 1108 and 1110 causes blood conduit 1112 to assume a more open configuration, as shown in FIG. 4. Thus, while in this embodiment conduit 1112 does not have the same self-expanding properties as the expandable scaffolds, the conduit will assume a deployed, more open configuration when the working end is deployed. At least a portion of central region 1113 of conduit 1112 is positioned at an aortic valve coaptation region and engages leaflets. In FIGS. 3A-3D, there is a short length of central region 1113 that extends distally beyond the leaflets VL, but at least some portion of central region 1113 is axially within the leaflets.

Continued retraction of an outer shaft or sheath (and/or distal movement of working end 1104 relative to an outer sheath or shaft) deploys first expandable member 1108. In this embodiment, first expandable scaffold 1108 has been expanded and positioned (as shown) in a deployed configuration such that proximal end 1121 is in the ascending aorta AA, and proximal to leaflets "VL." Distal end 1122 has also been positioned proximal to leaflets VL, but in some methods distal end 1122 may extend slightly axially within the leaflets VL. This embodiment is an example of a method in which at least half of first expandable member 1110 is within the ascending aorta, as measured along its length (measured along the longitudinal axis). And as shown, this is also an example of a method in which the entire first expandable member 1110 is within the AA. This is also an example of a method in which at least half of first impeller 1116 is positioned within the AA, and also an embodiment in which the entire first impeller 1116 is positioned within the AA.

At any time during or after deployment of pump portion 1104, the position of the pump portion can be assessed in any way, such as under fluoroscopy. The position of the pump portion can be adjusted at any time during or after deployment. For example, after second expandable scaffold 1110 is released but before first expandable member 1108 is released, pump portion 1104 can be moved axially (distally or proximally) to reposition the pump portion. Additionally, for example, the pump portion can be repositioned after the entire working portion has been released from a sheath to a desired final position.

It is understood that the positions of the components (relative to the anatomy) shown in FIG. 4 are considered exemplary final positions for the different components of working portion 1104, even if there was repositioning that occurred after initial deployment.

The one or more expandable members herein can be configured to be, and can be expanded in a variety of ways, such as via self-expansion, mechanical actuation (e.g., one or more axially directed forces on the expandable member, expanded with a separate balloon positioned radially within the expandable member and inflated to push radially outward on the expandable member), or a combination thereof.

Expansion as used herein refers generally to reconfiguration to a larger profile with a larger radially outermost dimension (relative to the longitudinal axis), regardless of the specific manner in which the one or more components are expanded. For example, a stent that self-expands and/or is subject to a radially outward force can "expand" as that term is used herein. A device that unfurls or unrolls can also assume a larger profile, and can be considered to expand as that term is used herein.

The impellers can similarly be adapted and configured to be, and can be expanded in a variety of ways depending on their construction. For examples, one or more impellers can, upon release from a sheath, automatically revert to or towards a different larger profile configuration due to the material(s) and/or construction of the impeller design (see, for example, U.S. Pat. No. 6,533,716, or U.S. Pat. No. 7,393,181, both of which are incorporated by reference herein for all purposes). Retraction of an outer restraint can thus, in some embodiments, allow both the expandable member and the impeller to revert naturally to a larger profile, deployed configuration without any further actuation.

As shown in the example in FIG. 4, the working portion includes first and second impellers that are spaced on either side of an aortic valve, each disposed within a separate expandable member. This is in contrast to some designs in which a working portion includes a single elongate expandable member. Rather than a single generally tubular expandable member extending all the way across the valve, working end 1104 includes a conduit 1112 extending between expandable members 1108 and 1110. The conduit is more flexible and deformable than the expandable baskets, which can allow for more deformation of the working portion at the location of the leaflets than would occur if an expandable member spanned the aortic valve leaflets. This can cause less damage to the leaflets after the working portion has been deployed in the subject.

Additionally, forces on a central region of a single expandable member from the leaflets might translate axially to other regions of the expandable member, perhaps causing undesired deformation of the expandable member at the locations of the one or more impellers. This may cause the outer expandable member to contact the impeller, undesirably interfering with the rotation of the impeller. Designs that include separate expandable members around each impeller, particularly where each expandable member and each impeller are supported at both ends (i.e., distal and proximal), result in a high level of precision in locating the impeller relative to the expandable member. Two separate expandable members may be able to more reliably retain their deployed configurations compared with a single expandable member.

As described herein above, it may be desirable to be able to reconfigure the working portion so that it can be delivered within a 9F sheath and still obtain high enough flow rates when in use, which is not possible with some products currently in development and/or testing. For example, some products are too large to be able to be reconfigured to a small enough delivery profile, while some smaller designs may not be able to achieve the desired high flow rates. An exemplary advantage of the examples in FIGS. 1, 2, 3A-3D and 4 is that, for example, the first and second impellers can work together to achieve the desired flow rates, and by having two axially spaced impellers, the overall working portion can be reconfigured to a smaller delivery profile than designs in which a single impeller is used to achieve the desired flow rates. These embodiments thus use a plurality of smaller, reconfigurable impellers that are axially spaced to achieve both the desired smaller delivery profile as well as to achieve the desired high flow rates. However, it should be understood that these or any other embodiment in this disclosure can include only a single impeller, such as only a proximal impeller or only a distal impeller.

Figure 5:
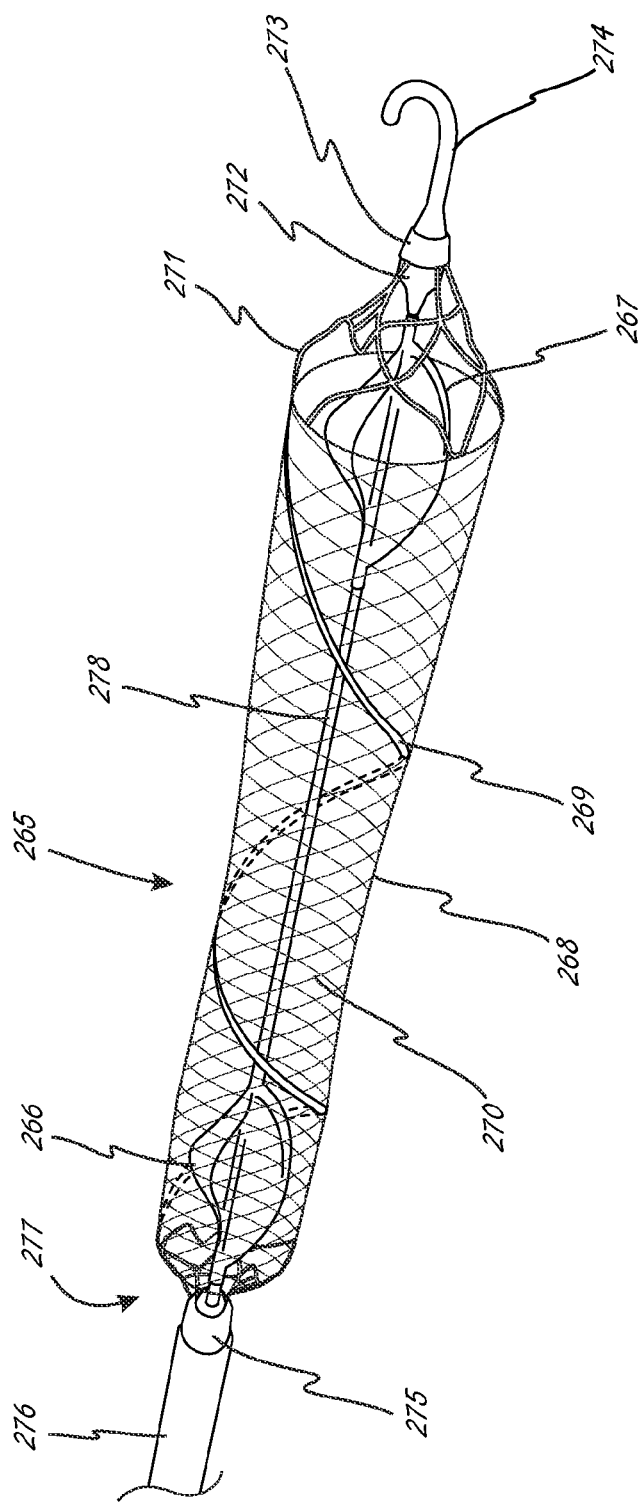
FIG. 5 illustrates an exemplary pump portion including an expandable impeller housing, a blood conduit, and a plurality of impellers.

FIG. 5 illustrates a working portion that is similar to the working portion shown in FIG. 1. Working portion 265 includes proximal impeller 266, distal impeller 267, both of which are coupled to drive shaft 278, which extends into distal bearing housing 272. There is a similar proximal bearing housing at the proximal end of the working portion. Working portion also includes expandable scaffold or member, referred to 270 generally, and blood conduit 268 that is secured to the expandable member and extends almost the entire length of expandable member. Expandable member 270 includes distal struts 271 that extend to and are secured to strut support 273, which is secured to distal tip 273. Expandable member 270 also includes proximal struts there are secured to a proximal strut support. All features similar to that shown in FIG. 1 are incorporated by reference for all purposes into this embodiment even if not explicitly stated. Expandable member 265 also includes helical tension member 269 that is disposed along the periphery of the expandable member, and has a helical configuration when the expandable member is in the expanded configuration as shown. The helical tension member 269 is disposed and adapted to induce rotation wrap upon collapse. Working portion 265 can be collapsed from the shown expanded configuration while simultaneously rotating one or both impellers at a relatively slow speed to facilitate curled collapse of the impellers due to interaction with the expandable member. Helical tension member 269 (or a helical arrangement of expandable member cells) will act as a collective tension member and is configured so that when the expandable basket is pulled in tension along its length to collapse (such as by stretching to a much greater length, such as approximately doubling in length) tension member 269 is pulled into a straighter alignment, which causes rotation/twisting of the desired segment(s) of the expandable member during collapse, which causes the impeller blades to wrap radially inward as the expandable member and blades collapse. An exemplary configuration of such a tension member would have a curvilinear configuration when in helical form that is approximately equal to the maximum length of the expandable member when collapsed. In alternative embodiments, only the portion(s) of the expandable member that encloses a collapsible impeller is caused to rotate upon collapse.

There are alternative ways to construct the working portion to cause rotation of the expandable member upon collapse by elongation (and thus cause wrapping and collapse of the impeller blades). Any expandable member can be constructed with this feature, even in dual-impeller designs. For example, with an expandable member that includes a plurality of "cells," as that term is commonly known (e.g., a laser cut elongate member), the expandable member may have a plurality of particular cells that together define a particular configuration such as a helical configuration, wherein the cells that define the configuration have different physical characteristics than other cells in the expandable member. In some embodiments the expandable member can have a braided construction, and the twist region may constitute the entire group of wires, or a significant portion (e.g., more than half), of the braided wires. Such a twisted braid construction may be accomplished, for example, during the braiding process, such as by twisting the mandrel that the wires are braided onto as the mandrel is pulled along, especially along the length of the largest-diameter portion of the braided structure. The construction could also be accomplished during a second operation of the construction process, such as mechanically twisting a braided structure prior to heat-setting the wound profile over a shaped mandrel.

Any of the blood conduits herein act to, are configured to, and are made of material(s) that create a fluid lumen therein between a first end (e.g., distal end) and a second end (e.g., proximal end). Fluid flows into the inflow region, through the fluid lumen, and then out of an outflow region. Flow into the inflow region may be labeled herein as "I," and flow out at the outflow region may be labeled "O." Any of the conduits herein can be impermeable. Any of the conduits herein can alternatively be semipermeable. Any of the conduits herein may also be porous, but will still define a fluid lumen therethrough. In some embodiments the conduit is a membrane, or other relatively thin layered member. Any of the conduits herein, unless indicated to the contrary, can be secured to an expandable member such that the conduit, where is it secured, can be radially inside and/or outside of the expandable member. For example, a conduit may extend radially within the expandable member so that inner surface of the conduit is radially within the expandable member where it is secured to the expandable member.

Any of the expandable scaffolds or member(s) herein may be constructed of a variety of materials and in a variety of ways. For example, the expandable member may have a braided construction, or it can be formed by laser machining. The material can be deformable, such as nitinol. The expandable member can be self-expanding or can be adapted to be at least partially actively expanded.

In some embodiments, the expandable scaffold or member is adapted to self-expand when released from within a containing tubular member such as a delivery catheter, a guide catheter or an access sheath. In some alternative embodiments, the expandable member is adapted to expand by active expansion, such as action of a pull-rod that moves at least one of the distal end and the proximal end of the expandable member toward each other. In alternative embodiments, the deployed configuration can be influenced by the configuration of one or more expandable structures. In some embodiments, the one or more expandable members can deployed, at least in part, through the influence of blood flowing through the conduit. Any combination of the above mechanisms of expansion may be used.

The blood pumps and fluid movement devices, system and methods herein can be used and positioned in a variety of locations within a body. While specific examples may be provided herein, it is understood that that the working portions can be positioned in different regions of a body than those specifically described herein.

Figures 6A, 6B, 6C, 7:
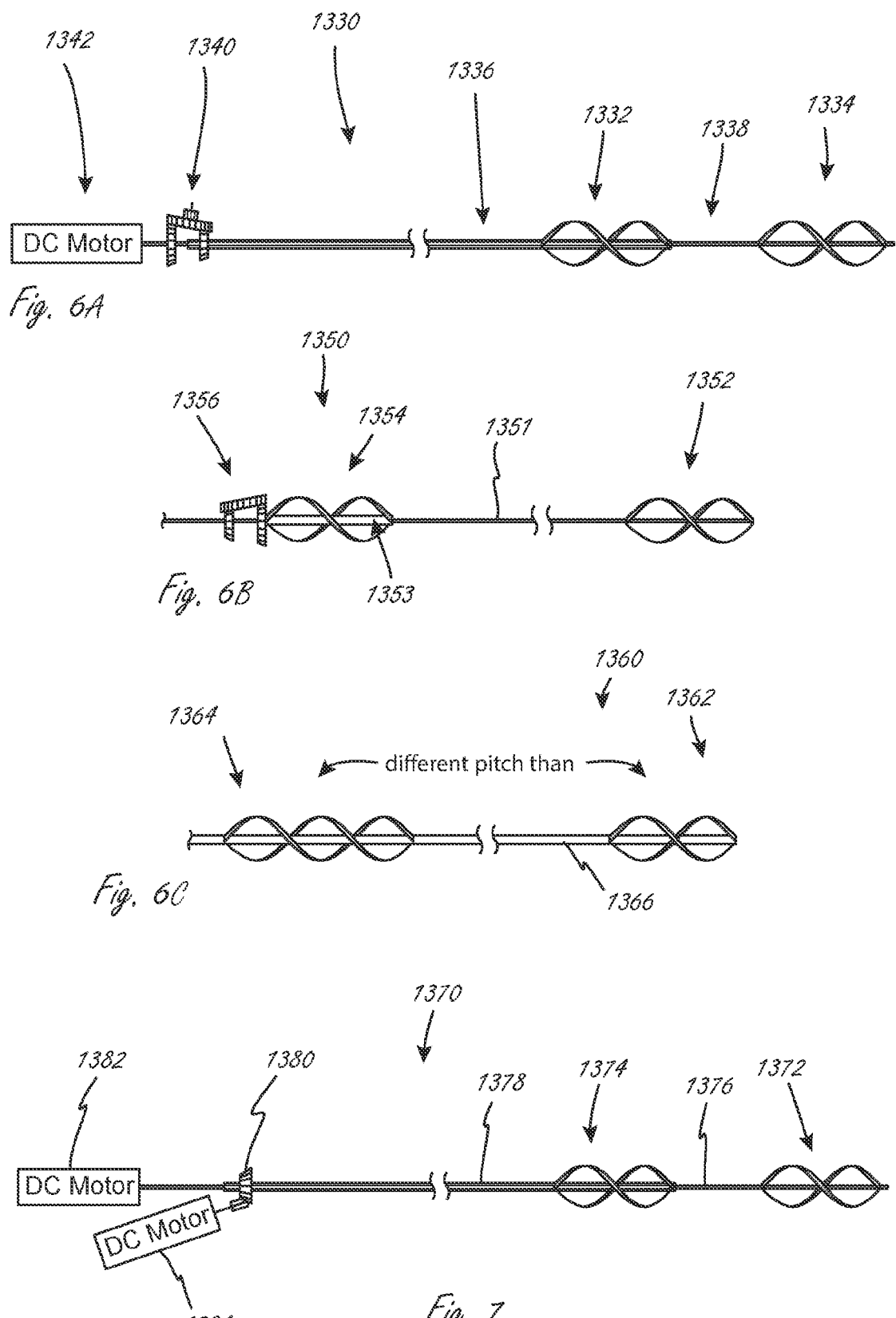
FIG. 6A illustrates at least a portion of an exemplary catheter blood pump that includes a pump portion, wherein at least two different impellers can be rotated at different speeds.
FIG. 6B illustrates at least a portion of an exemplary catheter blood pump that includes a pump portion, where at least two different impellers can be rotated at different speeds.
FIG. 6C illustrates at least a portion of an exemplary catheter blood pump that includes a pump portion with at least two impellers having different pitches.
FIG. 7 illustrates a portion of an exemplary catheter blood pump that includes a pump portion.

In any of the embodiments herein in which the catheter blood pump includes a plurality of impellers, the device can be adapted such that the impellers rotate at different speeds. FIG. 6A illustrates a medical device that includes gearset 1340 coupled to both inner drive member 1338 and outer drive member 1336, which are in operable communication with distal impeller 1334 and proximal impeller 1332, respectively. The device also includes motor 1342, which drives the rotation of inner drive member 1338. Inner drive member 1338 extends through outer drive member 1336. Activation of the motor 1332 causes the two impellers to rotate at different speeds due to an underdrive or overdrive ratio. Gearset 1340 can be adapted to drive either the proximal or distal impeller faster than the other. Any of the devices herein can include any of the gearsets herein to drive the impellers at different speeds.

FIG. 6B illustrates a portion of an alternative embodiment of a dual impeller device (1350) that is also adapted such that the different impellers rotate at different speeds. Gearset 1356 is coupled to both inner drive member 1351 and outer drive member 1353, which are coupled to distal impeller 1352 and proximal impeller 1354, respectively. The device also includes a motor like in FIG. 6A. FIGS. 6A and 6B illustrate how a gearset can be adapted to drive the proximal impeller slower or faster than the distal impeller.

FIG. 7 illustrates an exemplary alternative embodiment of fluid pump 1370 that can rotate first and second impellers at different speeds. First motor 1382 drives cable 1376, which is coupled to distal impeller 1372, while second motor 1384 drives outer drive member 1378 (via gearset 1380), which is coupled to proximal impeller 1374. Drive cable 1376 extends through outer drive member 1378. The motors can be individually controlled and operated, and thus the speeds of the two impellers can be controlled separately. This system setup can be used with any system herein that includes a plurality of impellers.

In some embodiments, a common drive mechanism (e.g., cable and/or shaft) can drive the rotation of two (or more) impellers, but the blade pitch of the two impellers (angle of rotational curvature) can be different, with the distal or proximal impeller having a steeper or more gradual angle than the other impeller. This can produce a similar effect to having a gearset. FIG. 6C shows a portion of a medical device (1360) that includes common drive cable 1366 coupled to proximal impeller 1364 and distal impeller 1362, and to a motor not shown. The proximal impellers herein can have a greater or less pitch than the distal impellers herein. Any of the working portions (or distal portions) herein with a plurality of impellers can be modified to include first and second impellers with different pitches.

In any of the embodiments herein, the pump portion may have a compliant or semi-compliant (referred to generally together as "compliant") exterior structure. In various embodiments, the compliant portion is pliable. In various embodiments, the compliant portion deforms only partially under pressure. For example, the central portion of the pump may be formed of a compliant exterior structure such that it deforms in response to forces of the valve. In this manner the exterior forces of the pump on the valve leaflets are reduced. This can help prevent damage to the valve at the location where it spans the valve.

Figures 8, 9:
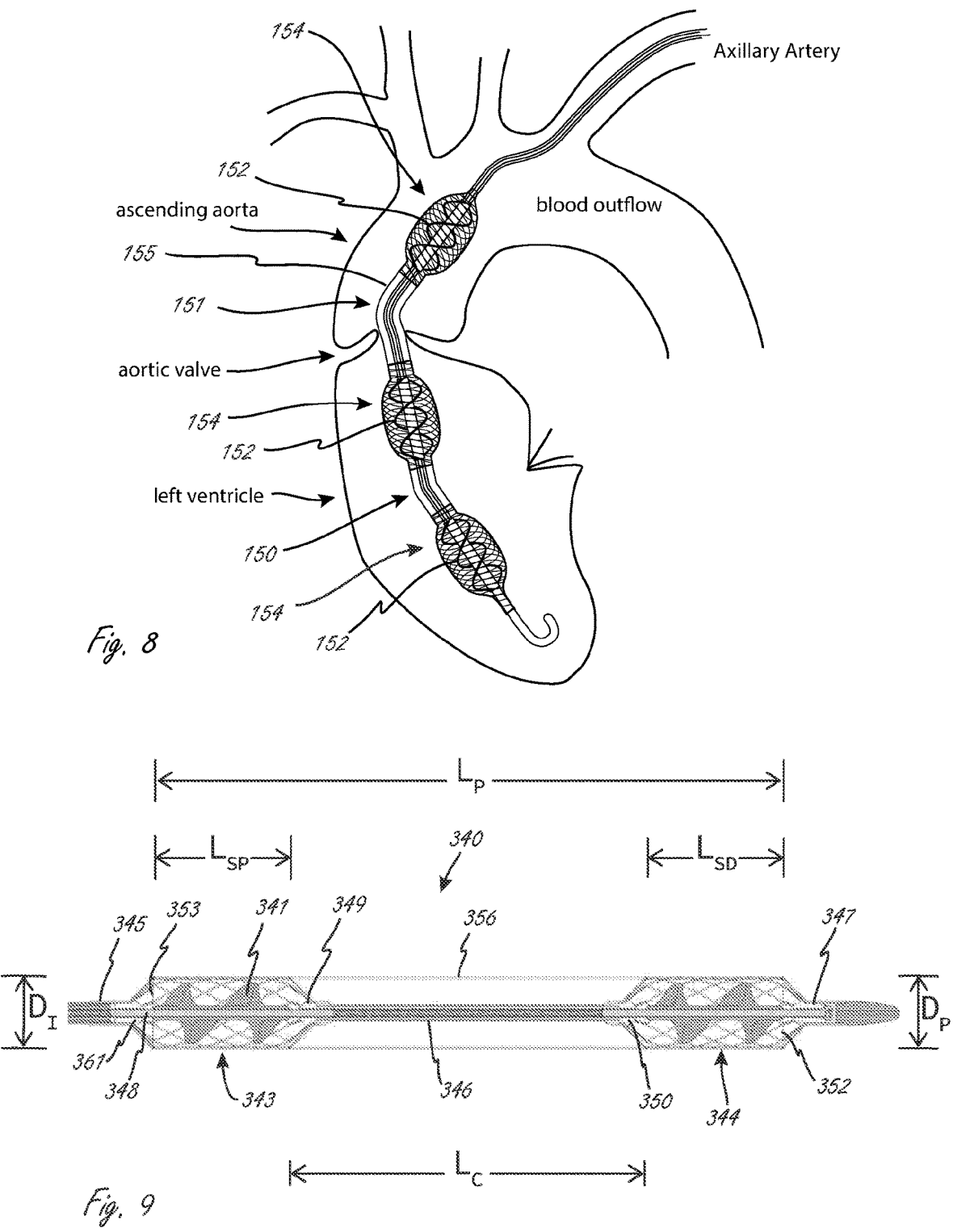
FIG. 8 illustrates an exemplary expandable pump portion including a plurality of expandable impellers, including one or more bends formed therein between adjacent impellers.
FIG. 9 illustrates an exemplary expandable pump portion comprising a plurality of impellers and a blood conduit.

FIG. 8 illustrates an exemplary embodiment of a pump portion that includes first, second and third axially spaced impellers 152, each of which is disposed within an expandable member 154. Conduit 155 can extend along the length of the pump portion, as in described in various embodiments herein, which can help create and define the fluid lumen. In alternative embodiments, however, the first, second, and third impellers may be disposed within a single expandable member, similar to that shown in FIG. 1.

In FIG. 8, a fluid lumen extends from a distal end to a proximal end, features of which are described elsewhere herein. The embodiment in FIG. 8 can include any other suitable feature, including methods of use, described herein.

The embodiment in FIG. 8 is also an example of an outer housing having at least one bend formed therein between a proximal impeller distal end and a distal impeller proximal end, such that a distal region of the housing distal to the bend is not axially aligned with a proximal region of the housing proximal to the bend along an axis. In this embodiment there are two bends 150 and 151 formed in the housing, each one between two adjacent impellers.

In a method of use, a bend formed in a housing can be positioned to span a valve, such as the aortic valve shown in FIG. 8. In this method of placement, a central impeller and distal-most impeller are positioned in the left ventricle, and a proximal-most impeller is positioned in the ascending aorta. Bend 151 is positioned just downstream to the aortic valve.

A bend such as bend 150 or 151 can be incorporated into any of the embodiments or designs herein. The bend may be a preformed angle or may be adjustable in situ.

In any of the embodiments herein, unless indicated to the contrary, the outer housing can have a substantially uniform diameter along its length.

In FIG. 8, the pump is positioned via the axillary artery, which is an exemplary method of accessing the aortic valve, and which allows the patient to walk and be active with less interruption. Any of the devices herein can be positioned via the axillary artery. It will be appreciated from the description herein, however, that the pump may be introduced and tracked into position in various manners including a femoral approach over the aortic arch.

One aspect of the disclosure is a catheter blood pump that includes a distal impeller axially spaced from a proximal impeller. Distal and proximal impellers may be axially spaced from each other. For example, the distal and proximal impellers may be connected solely by their individual attachment to a common drive mechanism. This is different from a single impeller having multiple blade rows or sections. A distal impeller as that phrase is used herein does not necessarily mean a distal-most impeller of the pump, but can refer generally to an impeller that is positioned further distally than a proximal impeller, even if there is an additional impeller than is disposed further distally than the distal impeller. Similarly, a proximal impeller as that phrase is used herein does not necessarily mean a proximal-most impeller of the pump, but can refer generally to an impeller that is positioned further proximally than a proximal impeller, even if there is an additional impeller than is disposed further proximally than the proximal impeller. Axial spacing (or some derivative thereof) refers to spacing along the length of a pump portion, such as along a longitudinal axis of the pump portion, even if there is a bend in the pump portion. In various embodiments, each of the proximal and distal impellers are positioned within respective housings and configured to maintain a precise, consistent tip gap, and the span between the impellers has a relatively more flexible (or completely flexible) fluid lumen. For example, each of the impellers may be positioned within a respective housing having relatively rigid outer wall to resist radial collapse. The sections between the impellers may be relatively rigid, in some embodiments the section is held open primarily by the fluid pressure within.

Although not required for the embodiments therein, there may be advantages to having a minimum axial spacing between a proximal impeller and a distal impeller. For example, a pump portion may be delivered to a target location through parts of the anatomy that have relatively tight bends, such as, for example, an aorta, and down into the aortic valve. For example, a pump portion may be delivered through a femoral artery access and to an aortic valve. It can be advantageous to have a system that is easier to bend so that it is easier to deliver the system through the bend(s) in the anatomy. Some designs where multiple impellers are quite close to each other may make the system, along the length that spans the multiple impellers, relatively stiff along that entire length that spans the multiple impellers. Spacing the impellers apart axially, and optionally providing a relatively flexible region in between the impellers, can create a part of the system that is more flexible, is easier to bend, and can be advanced through the bends more easily and more safely. An additional exemplary advantage is that the axial spacing can allow for a relatively more compliant region between the impellers, which can be positioned at, for example, the location of a valve (e.g., an aortic valve). Furthermore, there are other potential advantages and functional differences between the various embodiments herein and typical multistage pumps. A typical multistage pump includes rows of blades (sometimes referred to as impellers) in close functional spacing such that the rows of blades act together as a synchronized stage. One will appreciate that the flow may separate as it passes through the distal impeller. In various embodiments as described herein, distal and proximal impellers can be spaced sufficiently apart such that the flow separation from the distal impeller is substantially reduced (i.e., increased flow reattachment) and the localized turbulent flow is dissipated before the flow enters the proximal impeller.

In any of the embodiments or in any part of the description herein that include a distal impeller and a proximal impeller, the axial spacing between a distal end of the proximal impeller and a proximal end of the distal impeller can be from 1.5 cm to 25 cm (inclusive) along a longitudinal axis of the pump portion, or along a longitudinal axis of a housing portion that includes a fluid lumen. The distance may be measured when the pump portion, including any impellers, is in an expanded configuration. This exemplary range can provide the exemplary flexibility benefits described herein as the pump portion is delivered through curved portions of the anatomy, such as, for example, an aortic valve via an aorta. FIG. 9 (shown outside a patient in an expanded configuration) illustrates length Lc, which illustrates an axial spacing between impellers, and in some embodiments may be from 1.5 cm to 25 cm as set forth herein. In embodiments in which there may be more than two impellers, any two adjacent impellers (i.e., impellers that do not have any other rotating impeller in between them) may be spaced axially by any of the axial spacing distances described herein.

While some embodiments include a proximal impeller distal end that is axially spaced 1.5 cm to 25 cm from a distal impeller proximal end along an axis, the disclosure herein also includes any axial spacings that are subranges within that general range of 1.5 cm to 25 cm. That is, the disclosure includes all ranges that have any lower limit from 1.5 and above in that range, and all subranges that have any upper limit from 25 cm and below. The examples below provide exemplary subranges. In some embodiments, a proximal impeller distal end is axially spaced 1.5 cm to 20 cm from a distal impeller proximal end along an axis, 1.5 cm to 15 cm, 1.5 cm to 10 cm, 1.5 cm to 7.5 cm, 1.5 cm to 6 cm, 1.5 cm to 4.5 cm, 1.5 cm to 3 cm. In some embodiments the axial spacing is 2 cm to 20 cm, 2 cm to 15 cm, 2 cm to 12 cm, 2 cm to 10 cm, 2 cm to 7.5 cm, 2 cm to 6 cm, 2 cm to 4.5 cm, 2 cm to 3 cm. In some embodiments the axial spacing is 2.5 cm to 15 cm, 2.5 cm to 12.5 cm, 2.5 cm to 10 cm, 2.5 cm to 7.5 cm, or 2.5 cm to 5 cm (e.g., 3 cm). In some embodiments the axial spacing is 3 cm to 20 cm, 3 cm to 15 cm, 3 cm to 10 cm, 3 cm to 7.5 cm, 3 cm to 6 cm, or 3 cm to 4.5 cm. In some embodiments the axial spacing is 4 cm to 20 cm, 4 cm to 15 cm, 4 cm to 10 cm, 4 cm to 7.5 cm, 4 cm to 6 cm, or 4 cm to 4.5 cm. In some embodiments the axial spacing is 5 cm to 20 cm, 5 cm to 15 cm, 5 cm to 10 cm, 5 cm to 7.5 cm, or 5 cm to 6 cm. In some embodiments the axial spacing is 6 cm to 20 cm, 6 cm to 15 cm, 6 cm to 10 cm, or 6 cm to 7.5 cm. In some embodiments the axial spacing is 7 cm to 20 cm, 7 cm to 15 cm, or 7 cm to 10 cm. In some embodiments the axial spacing is 8 cm to 20 cm, 8 cm to 15 cm, or 8 cm to 10 cm. In some embodiments the axial spacing is 9 cm to 20 cm, 9 cm to 15 cm, or 9 cm to 10 cm. In various embodiments, the fluid lumen between the impellers is relatively unsupported.

In any of the embodiments herein the one or more impellers may have a length, as measured axially between an impeller distal end and an impeller proximal end (shown as "$L_{SD}$" and "$L_{SP}$", respectively, in FIG. 9), from 0.5 cm to 10 cm, or any subrange thereof. The examples below provide exemplary subranges. In some embodiments the impeller axial length is from 0.5 cm to 7.5 cm, from 0.5 cm to 5 cm, from 0.5 cm to 4 cm, from 0.5 cm to 3 cm, from 0.5 cm to 2, or from 0.5 cm to 1.5 cm. In some embodiments the impeller axial length is from 0.8 cm to 7.5 cm, from 0.8 cm to 5 cm, from 0.8 cm to 4 cm, from 0.8 cm to 3 cm, from 0.8 cm to 2 cm, or from 0.8 cm to 1.5 cm. In some embodiments the impeller axial length is from 1 cm to 7.5 cm, from 1 cm to 5 cm, from 1 cm to 4 cm, from 1 cm to 3 cm, from 1 cm to 2 cm, or from 1 cm to 1.5 cm. In some embodiments the impeller axial length is from 1.2 cm to 7.5 cm, from 1.2 cm to 5 cm, from 1.2 cm to 4 cm, from 1.2 cm to 3 cm, from 1.2 to 2 cm, or from 1.2 cm to 1.5 cm. In some embodiments the impeller axial length is from 1.5 cm to 7.5 cm, from 1.5 cm to 5 cm, from 1.5 cm to 4 cm, from 1.5 cm to 3 cm, or from 1.5 cm to 2 cm. In some embodiments the impeller axial length is from 2 cm to 7.5 cm, from 2 cm to 5 cm, from 2 cm to 4 cm, or from 2 cm to 3 cm. In some embodiments the impeller axial length is from 3 cm to 7.5 cm, from 3 cm to 5 cm, or from 3 cm to 4 cm. In some embodiments the impeller axial length is from 4 cm to 7.5 cm, or from 4 cm to 5 cm.

In any of the embodiments herein the fluid lumen can have a length from a distal end to a proximal end, shown as length Lp in FIG. 9. In some embodiments the fluid lumen length Lp is from 4 cm to 40 cm, or any subrange therein. For example, in some embodiments the length Lp can be from 4 cm to 30 cm, from 4 cm to 20 cm, from 4 cm to 18 cm, from 4 cm to 16 cm, from 4 cm to 14 cm, from 4 cm to 12 cm, from 4 cm to 10 cm, from 4 cm to 8 cm, from 4 cm to 6 cm.

In any of the embodiments herein the scaffold (also referred to as the housing) can have a deployed (expanded) diameter (e.g., outer diameter), at least the location of an impeller (and optionally at a location between impellers), shown as dimension Dp in FIG. 9. In some embodiments Dp can be from 0.3 cm to 1.5 cm (3.0 mm to 15.0 mm), or any subrange therein. For example, Dp may be from 0.4 cm to 1.4 cm, from 0.4 cm to 1.2 cm, from 0.4 cm to 1.0 cm, from 0.4 cm to 0.8 cm, or from 0.4 cm to 0.6 cm. In some embodiments, Dp may be from 0.5 cm to 1.4 cm, from 0.5 cm to 1.2 cm, from 0.5 cm to 1.0 cm, from 0.5 cm to 0.8 cm, or from 0.5 cm to 0.6 cm, from 0.5 cm to 0.8 cm, or from 0.5 cm to 1.0 cm. In some embodiments Dp may be from 0.6 cm to 1.4 cm, from 0.6 cm to 1.2 cm, from 0.6 cm to 1.0 cm, or from 0.6 cm to 0.8 cm. In some embodiments Dp may be from 0.7 cm to 1.4 cm, from 0.7 cm to 1.2 cm, from 0.7 cm to 1.0 cm, or from 0.7 cm to 0.8 cm.

In any of the embodiments herein an impeller can have a deployed diameter, shown as dimension $D_1$ in FIG. 9. In some embodiments $D_1$ can be from 1 mm-30 mm, or any subrange therein. For example, in some embodiments $D_1$ may be from 1 mm-15 mm, from 2 mm-12 mm, from 2.5 mm-10 mm, or 3 mm-8 mm.

In any of the embodiments herein, a tip gap exists between an impeller outer diameter and a fluid lumen inner diameter. In some embodiments the tip gap can be from 0.01 mm-1 mm, such as 0.05 mm to 0.8 mm, or such as 0.1 mm-0.5 mm.

In any of the embodiments herein that includes multiple impellers, the axial spacing between impellers (along the length of the pump portion, even if there is a bend in the pump portion) can be from 2 mm to 100 mm, or any combination of upper and lower limits inclusive of 5 and 100 mm (e.g., from 10 mm-80 mm, from 15 mm-70 mm, from 20 mm-50 mm, 2 mm-45 mm, etc.).

Any of the pump portions herein that include a plurality of impellers may also include more than two impellers, such as three, four, or five impellers (for example).

In any of the embodiments herein a diameter (e.g., inner diameter) of the scaffold (also referred to as the housing) in a collapsed state (e.g., for sheathing) can be from 2.0 mm to 7.0 mm, or any subrange therein. For example, the diameter (e.g., inner diameter) of the scaffold in a collapsed state may be from 2.0 mm to 2.5 mm, from 2.0 mm to 3.0 mm, from 2.0 mm to 4.0 mm, from 2.0 mm to 5.0 mm, from 2.0 mm to 6.0 mm, from 2.5 mm to 4.5 mm, from 2.5 mm to 6.0 mm, from 3.0 mm to 6.0 mm, or from 3.0 mm to 4.5 mm.

Figure 10:
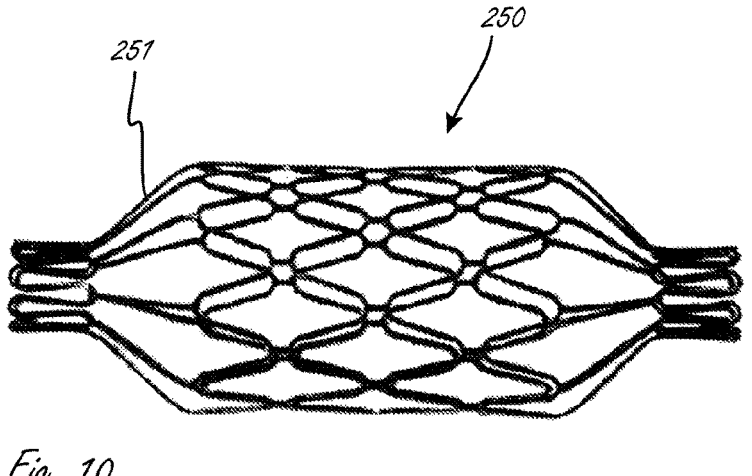
FIG. 10 illustrates an exemplary scaffold design and exemplary struts.

FIG. 10 illustrates an expandable scaffold 250 that may be one of at least two expandable scaffolds of a pump portion, such as the expandable scaffolds in FIGS. 3A-3D, wherein each expandable scaffold at least partially surrounds an impeller. The scaffold design in FIG. 10 has proximal struts 251 (only one labeled) extending axially therefrom. Having a separate expandable scaffold 250 for each impeller provides for the ability to have different geometries for any of the individual impellers. Additionally, this design reduces the amount of scaffold material (e.g., Nitinol) over the length of the expandable blood conduit, which may offer increased tracking when sheathed. A potential challenge with these designs may include creating a continuous membrane between the expandable scaffolds in the absence of an axially extending scaffolding material (see FIG. 3A). Any other aspect of the expandable scaffolds or members herein, such as those described in FIGS. 3A-3D, may be incorporated by reference into this exemplary design. Struts 251 may be disposed at a pump inflow or outflow. Struts 251 may be proximal struts or they may be distal struts.

Figure 11:
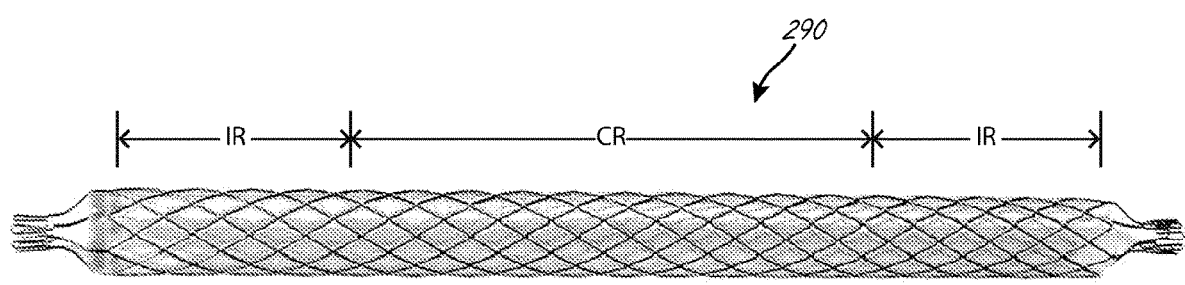
FIG. 11 illustrate an exemplary scaffold design and exemplary struts.

FIG. 11 show an exemplary scaffold along a length of the blood conduit. Central region "CR" may be axially between proximal and distal impellers. Central region "CR" flexibility is increased relative to scaffold impeller regions "IR" due to breaks or discontinuities in the scaffold pattern in central region. The scaffold has relatively more rigid impeller sections "IR" adjacent the central region where impellers may be disposed (not shown). The relatively increased rigidity in the impeller regions IR may help maintain tip gap and impeller concentricity. This pump scaffold pattern provides for a flexibility distribution, along its length, of a proximal section of relatively less flexibility ("IR"), a central region "CR" of relatively higher flexibility, and a distal section "IR" of relatively less flexibility than the central region. The relatively less flexible sections (i.e., the two IR regions) are where proximal and distal impellers may be disposed (not shown but other embodiments are fully incorporated herein in this regard), with a relatively more flexible region in between. Exemplary benefits of the relative flexibility in these respective sections are described elsewhere herein. FIG. 11 is an example of a scaffold that is continuous from a first end region to a second end region, even though there are breaks or discontinuities in some locations of the scaffold. There is at least one line that can be traced along a continuous structural path from a first end region to a second end region.

The following disclosure provides exemplary method steps that may be performed when using any of the blood pumps, or portions thereof, described herein. It is understood that not all of the steps need to be performed, but rather the steps are intended to be an illustrative procedure. It is also intended that, if suitable, in some instances the order of one or more steps may be different. Before use, the blood pump can be prepared for use by priming the lumens (including any annular spaces) and pump assembly with sterile solution (e.g., heparinized saline) to remove any air bubbles from any fluid lines. The catheter, including any number of purge lines, may then be connected to a console. Alternatively, the catheter may be connected to a console and/or a separate pump that are used to prime the catheter to remove air bubbles.

Figure 12A:
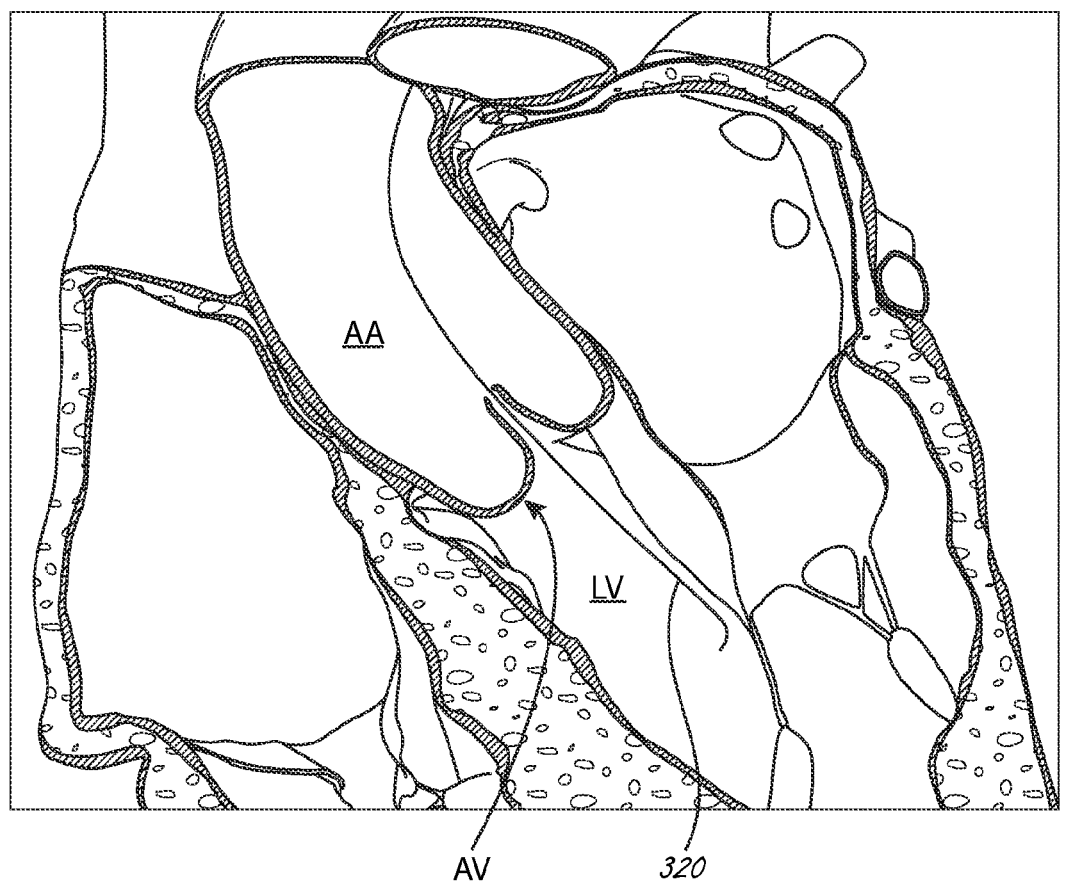
FIGS. 12A-12F illustrate an exemplary sequence of steps that may be performed to deploy an exemplary pump portion of a catheter blood pump.
Figure 12B:
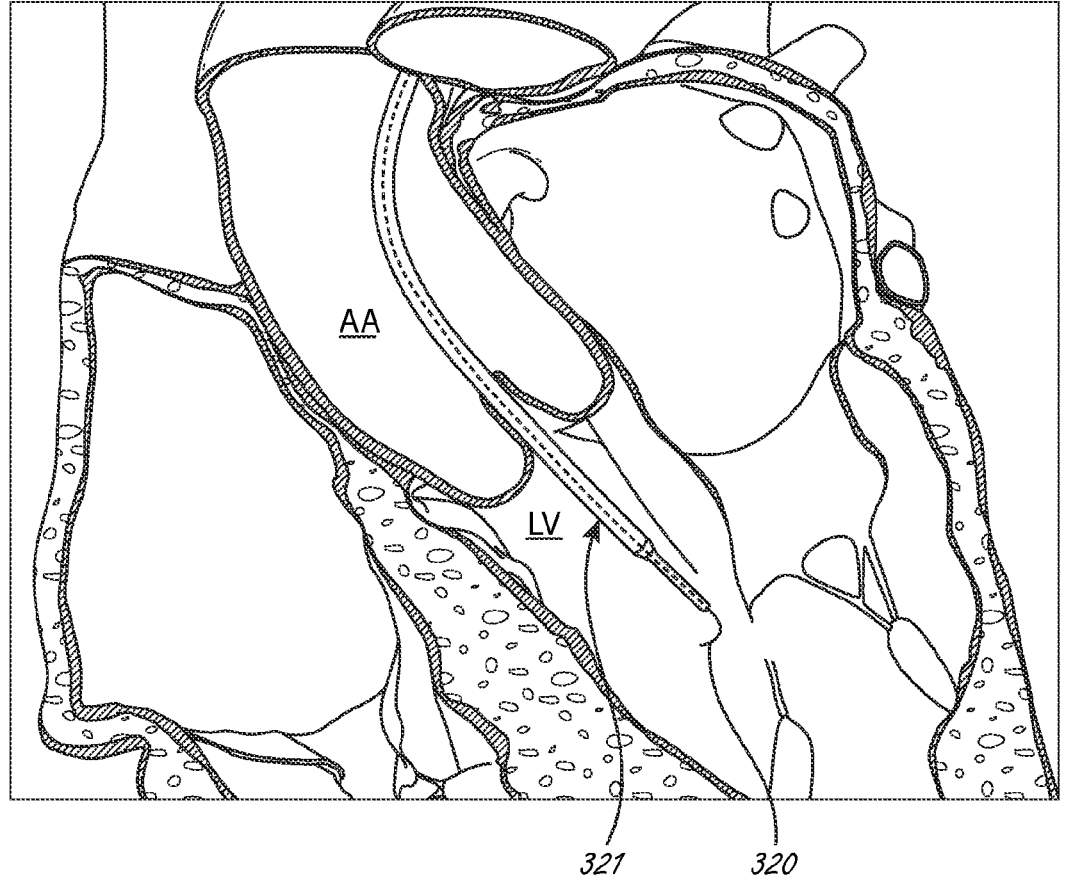

After priming the catheter, access to the patient's vasculature can be obtained (e.g., without limitation, via femoral access) using an appropriately sized introducer sheath. Using standard valve crossing techniques, a diagnostic pigtail catheter may then be advanced over a, for example, 0.035" guide wire until the pigtail catheter is positioned securely in the target location (e.g., left ventricle). The guidewire can then be removed and a second wire 320 (e.g., a 0.018" wire) can be inserted through the pigtail catheter. The pigtail catheter can then be removed (see FIG. 12A), and the blood pump 321 (including a catheter, catheter sheath, and pump portion within the sheath; see FIG. 12B) can be advanced over the second wire towards a target location, such as spanning an aortic valve "AV," and into a target location (e.g., left ventricle "LV"), using, for example, one or more radiopaque markers to position the blood pump.

Figure 12C:
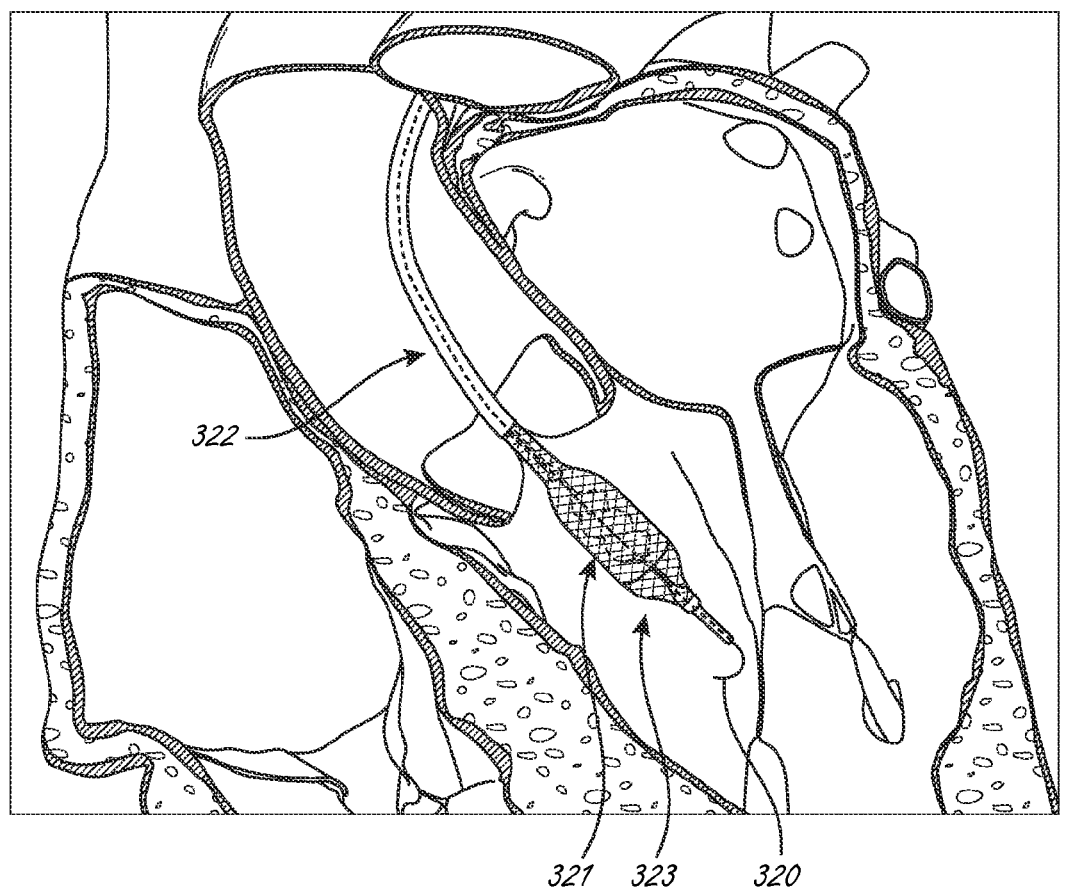
Figure 12D:
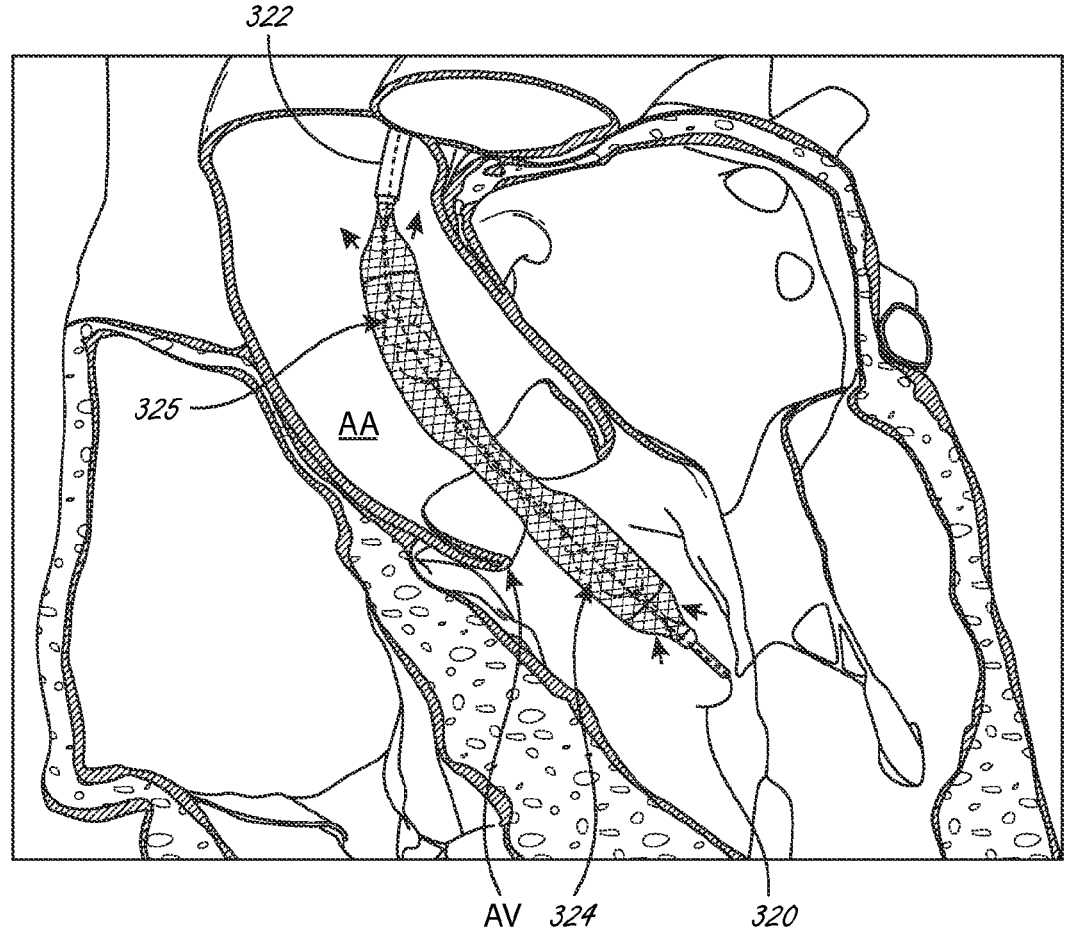

Once proper placement is confirmed, the catheter sheath 322 (see FIG. 12C) can be retracted, exposing first a distal region of the pump portion. In FIG. 12C a distal region of an expandable housing has been released from sheath 322 and is expanded, as is distal impeller 324. A proximal end of housing 323 and a proximal impeller are not yet released from sheath 322. Continued retraction of sheath 322 beyond the proximal end of housing 323 allows the housing 323 and proximal impeller 325 to expand (see FIG. 12D). The inflow region (shown with arrows even though the impellers are not yet rotating) and the distal impeller are in the left ventricle. The outflow (shown with arrows even though the impellers are not rotating yet) and proximal impeller are in the ascending aorta AA. The region of the outer housing in between the two impellers, which may be more flexible than the housing regions surrounding the impellers, as described in more detail herein, spans the aortic valve AV. In an exemplary operating position as shown, an inlet portion of the pump portion will be distal to the aortic valve, in the left ventricle, and an outlet of the pump portion will be proximal to the aortic valve, in the ascending aorta ("AA").

Figure 12E:
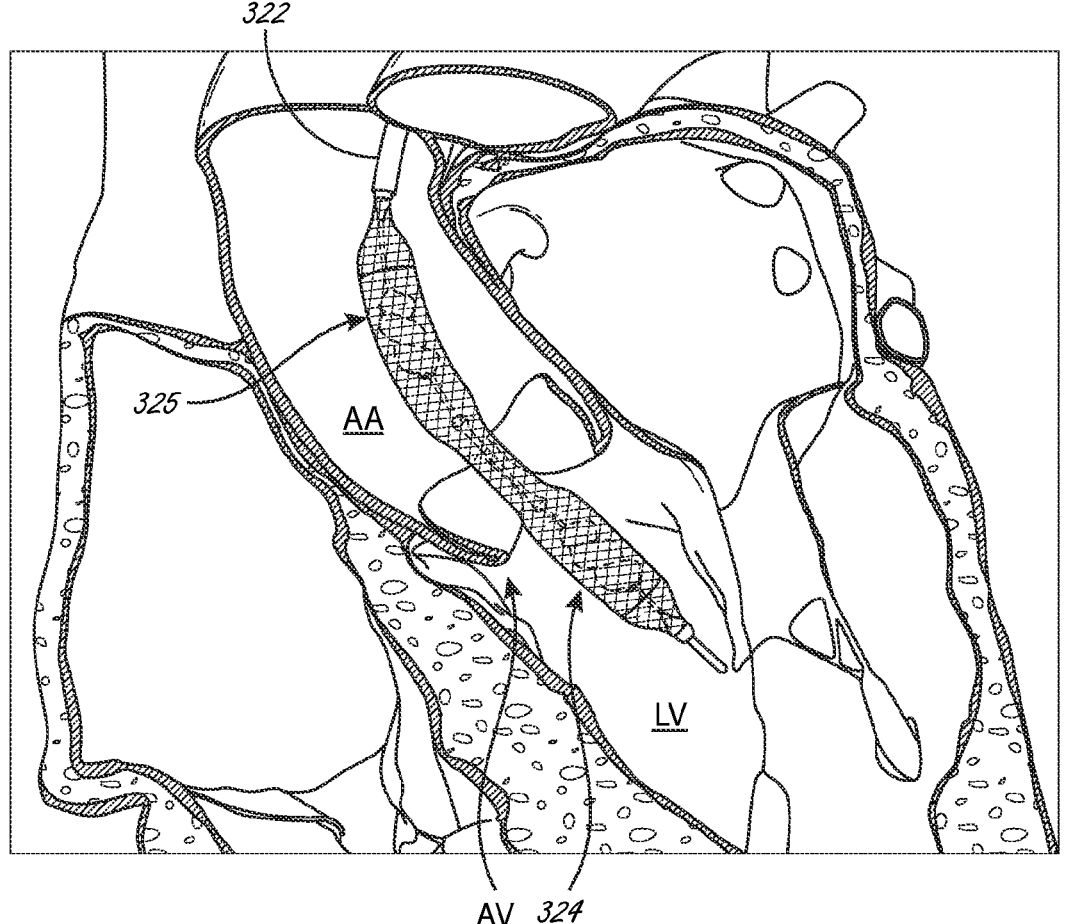
Figure 12F:
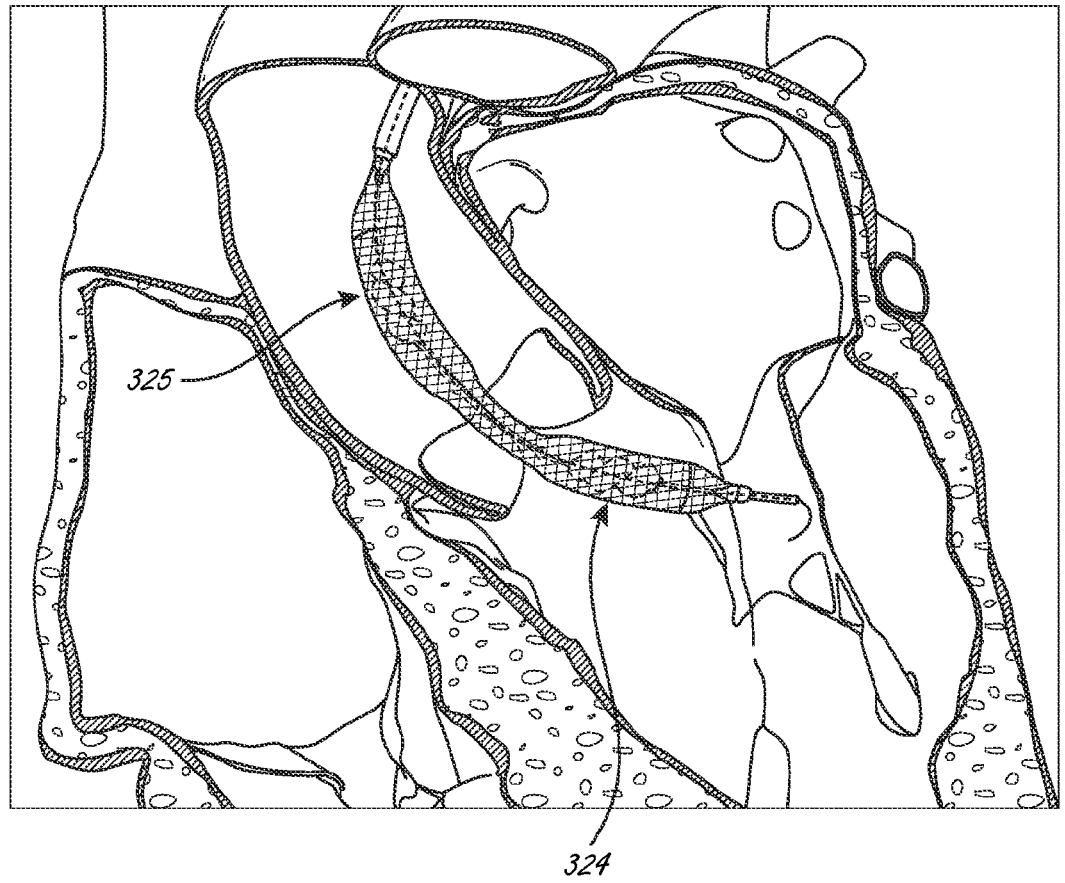

The second wire (e.g., an 0.018" guidewire) may then be moved prior to operation of the pump assembly (see FIG. 12E). If desired or needed, the pump portion can be deflected (active or passively) at one or more locations as described herein, as illustrated in FIG. 12F. For example, a region between two impellers can be deflected by tensioning a tensioning member that extends to a location between two impellers. The deflection may be desired or needed to accommodate the specific anatomy. As needed, the pump portion can be repositioned to achieve the intended placement, such as, for example, having a first impeller on one side of a heart valve and a second impeller on a second side of the heart valve. It is understood that in FIG. 12F, the pump portion is not in any way interfering or interacting with the mitral valve, even if it may appear that way from the figure.

As set forth above, this disclosure includes catheter blood pumps that include an expandable pump portion extending distally relative to a catheter. The pump portions include an impeller housing that includes an expandable blood conduit that defines a blood lumen. The blood conduit may include one or more scaffold sections that together may also be referred to herein as a single scaffold. In some exemplary embodiments the expandable blood conduit may include one or more of a proximal impeller scaffold, a distal impeller scaffold, and a central scaffold disposed between the proximal impeller scaffold and the distal impeller scaffold, where any combination thereof may also be referred to herein as a scaffold. Any individual proximal impeller scaffold or distal impeller scaffold may also be referred to herein as an expandable member, such as is shown in FIGS. 3A-3D. In some embodiments the expandable blood conduit may include a proximal impeller scaffold and additional scaffold extending distally therefrom, such as if the pump portion includes a proximal impeller but does not include a distal impeller. In any of the embodiments herein, a reference to a distal impeller is only by way of example, and pump portions herein need not include a distal impeller. Central scaffolds herein are generally less stiff in response to a radially inward force than a proximal scaffold, and optionally also less stiff than a distal scaffold, such as a distal impeller scaffold. Exemplary advantages of central scaffold sections that are less stiffness are set forth elsewhere herein. The blood conduit may also include a membrane coupled to the one or more scaffolds, the membrane at least partially defining the blood lumen. Membranes in this context may incorporate by reference herein the disclosure of conduits, including any feature or method of manufacturing described above. The catheter blood pumps may include an impeller disposed in a proximal region of the impeller housing, which may be a proximal impeller. The catheter blood pumps may also include a distal impeller in a distal region of the impeller housing. Exemplary impellers, including exemplary proximal and distal impellers, are set forth herein by way of example. An impeller that is at least partially within a portion of a scaffold may be described with respect to the relative position of the scaffold, such as a proximal impeller within at least a portion of a proximal scaffold, or a distal impeller within at least a portion of a distal scaffold.

When a proximal impeller is described as being within a proximal scaffold, it is understood that the proximal scaffold need not axially extend over an entire length of the impeller, as long as there is some amount of axial overlap. For example, some proximal impellers herein extend proximally from a blood conduit, and a proximal region of the proximal impeller is not surrounded by a blood conduit scaffold, while a distal region of the impeller is surrounded by scaffold. Similarly, when a distal impeller herein (if the pump includes a distal impeller) is described as being within a distal scaffold, it is understood that the distal scaffold need not axially extend over an entire length of the impeller, as long as there is some degree of axial overlap therebetween.

FIGS. 13A-17 illustrate exemplary designs for expandable scaffolds herein, which may at least partially surround an impeller that is at least partially disposed within a conduit that creates a fluid lumen. The scaffold patterns in FIGS. 13A-17 may be scaffold patterns that only extend over a particular impeller (e.g., a proximal basket or distal basket), or they may be scaffold patterns that extend over an entire blood conduit scaffold.

FIGS. 13A-17 illustrate expandable support members or scaffolds that each have an expanded configuration, wherein in the expanded configuration the support member has a plurality of continuous axially extending elements (e.g., 408, 410, 420, 430, 440) that are continuous and axially extending over at least 50% of a length of the expandable support member (e.g., $L_s$), and wherein the expandable support member includes a plurality of sets of connectors (e.g., 412/414, 409, 422/424, 432/434, 442/444) each set of connectors extending between first and second circumferentially adjacent continuous axially extending elements. In some embodiment the axially extending elements are linear or substantially linear.

FIGS. 13A-13C illustrate an exemplary pump portion 400 or a portion thereof that comprises an expandable impeller housing 402, wherein the expandable impeller housing having a blood conduit 404, the conduit defining a blood lumen between an housing inflow "I" and a housing outflow "O". The expandable impeller housing also includes an expandable scaffold or support member 406 at least partially surrounding an impeller (not shown in FIGS. 13A-13C) that is at least partially disposed within the conduit. FIGS. 14A-17 illustrate an expandable scaffold of the pump portion. It is understood that any expandable scaffold in any of FIGS. 13A-17 may be used in place of any expandable scaffold herein. Impeller housing 402 may illustrate the entire impeller housing, or it may only represent only a portion thereof, including only a single scaffold section, such as with any of the multi-impeller designs herein. It is thus understood that the structure shown in FIGS. 13A-C may only be a portion of the expandable housing of a pump portion. For example, a pump portion may include two of the expandable scaffold sections shown in FIGS. 13A-C, axially spaced apart, and coupled by a flexible membrane, for example. FIGS. 13A-C illustrate an expandable impeller housing that includes a plurality of axially extending elements 408 circumferentially spaced apart around the housing 402 from adjacent axially extending elements, as shown. FIGS. 13A and 13B show an expanded configuration of the housing, while FIG. 13C illustrates a model of a flat, unexpanded configuration with unitary struts 401 extending axially therefrom, as shown. The plurality of axially extending elements may be referred to as "elements" in the context of scaffolds for simplicity, but it is understood that they are not to be considered any other type of "element" herein unless specifically indicated as such. The elements in this embodiment may be axial and linear in the housing expanded configuration. Expandable scaffold 406 also includes circumferential connectors 409 that circumferentially connect adjacent axial elements and extend from one axial element to an adjacent axial element. In this exemplary embodiment all of the connectors have the same general configuration, which includes first and second segments meeting at a rounded peak that is oriented axially (proximally or distally depending on the reference frame), otherwise stated as pointing axially. Length $L_s$ of the scaffold and length Le of the elements is illustrated in FIG. 13C. Optional struts 401 are shown (which may be unitary with the scaffold). The axial elements 408 in this embodiment extend from a first axial element end 405 to second axial element end 405', which extend almost the entire length of the scaffold $L_s$. As shown, ends 405' of the elements (only one labeled) extend to a distal end region 407' of the scaffold 406. End 405 extends to proximal end region 407. The pump portion also includes a transition region 411, which includes circumferential extensions of adjacent axial elements, after which they meet to form a strut 401, as shown.

FIGS. 14A (expanded) and 14B (unexpanded) illustrate an exemplary expandable scaffold 406', which includes a plurality of axially extending elements 410. A first set of connectors 412 have "S" configurations, and a second circumferentially adjacent set of connectors 414 have inverse (reverse) "S" shapes. In the expanded configuration in FIG. 14A, the axial elements 410 may be linear, or they may have a slight curvilinear configuration as shown. Scaffold 406' includes transition region 411', which may have similar features to the transition region 411 herein. The relevant description from any other embodiment may be incorporated with the scaffold in FIGS. 14A-B (e.g., lengths of scaffold or support member and axial elements, transition region, etc.). Some of the optional struts 413 are shown, as are ends 405/405' of the axial elements. Scaffold 406' may be proximal or distal scaffold, or it may extend along the length of the impeller housing.

FIGS. 15A and 15B illustrate an exemplary expandable scaffold 406" that is similar to those in FIGS. 13A-C, 14A-B, 16, and 17. Axially extending elements 420 are shown, adjacent ones of which are connected by circumferential connectors 422 and 424, ends of which are axially offset. A first set of connectors 422 has a general S configuration, while a second set of connectors 424 are reverse S-shaped. In this embodiment the axially extending elements 420 are curvilinear, as shown. The pattern of S and inverse-S alternates around the expandable member, as it does in the scaffolds in FIGS. 14A and 14B. Scaffold 406" also includes a transition region 421, examples of which are described elsewhere herein. Scaffold 406" may be proximal or distal scaffold, or it may extend along the length of the impeller housing.

FIG. 16 illustrates a collapsed (unexpanded) configuration of an exemplary scaffold 406", which may have any other suitable features of any other support member or scaffold herein. Axially extending elements 430 are shown, connected by first set of S-shaped connectors 434 and a second set of inverse-S shaped connectors 432. The pattern of S and inverse-S shapes alternates circumferentially around the scaffold 406" as shown. Scaffold 406" may be proximal or distal scaffold, or it may extend along the length of the impeller housing.

FIG. 17 illustrates a collapsed (unexpanded) configuration of an exemplary scaffold 406"", which may have any other suitable features of any other support member or scaffold herein. Axially extending elements 440 are shown, connected by inverse-S shaped connectors. All sets of the connectors in this embodiment (e.g., set 442 and set 444) have the same configuration, and in this embodiment are all inverse-S shaped. Exemplary struts are shown axially disposed relative to the scaffold 406"", and the scaffold 406"" may include transition sections which are described elsewhere herein. Scaffold 406"" may be a proximal scaffold or a distal scaffold, or it may extend along the length of the impeller housing.

The scaffolds and blood conduit embodiments in FIGS. 13A-17 are illustrative, and may be modified to include aspects of other embodiments herein. The following description may provide modifications to the scaffolds in FIGS. 13A-17, any of which may be incorporated into any of the scaffolds in FIGS. 13A-17.

In any of the scaffolds shown in FIGS. 13A-17, at least a first end of each of the plurality of axially extending elements may extend to one or more of a proximal end region (e.g., 417', 407') and a distal end region (e.g., 417) of the expandable scaffold.

In any of the scaffolds shown in FIGS. 13A-17, at least one of, and optionally all of, the plurality of axially extending elements may be linear. In any of the scaffolds shown in FIGS. 13A-17, at least one of, and optionally all of, the plurality of axially extending elements may be curvilinear.

In any of the scaffolds shown in FIGS. 13A-17, each one of the plurality of axially extending elements may have proximal and distal ends, wherein the proximal and distal ends are substantially circumferentially aligned.

In any of the scaffolds shown in FIGS. 13A-17, each of the plurality of axially extending elements may have a circumferential span (illustrated as "CS" in FIG. 15A) that is not larger than 10 degrees circumferentially around the expandable scaffold, optionally not larger than 5 degrees of the expandable scaffold.

In any of the scaffolds shown in FIGS. 13A-17, each of the plurality of axially extending elements may follow a path that is substantially parallel with a longitudinal axis of the expandable scaffold.

In any of the embodiments in FIGS. 13A-17, each of the plurality of axially extending elements may be continuous and axially extending over at least 55% of a length of the expandable scaffold, optionally over at least 60%, optionally over at least 65%, optionally over at least 70%, optionally over at least 75%, optionally over at least 80%, optionally over at least 85%, optionally over at least 90, optionally over at least 95.

In any of the scaffolds shown in FIGS. 13A-17, all of the connectors in all of the sets of the plurality of sets of connectors may have the same configuration. In any of the scaffolds shown in FIGS. 13A-17, all of the connectors in all of the sets of the plurality of sets of connectors may not have the same configuration. In any of the scaffolds shown in FIGS. 13A-17, each individual set of connectors may have a plurality of connectors that have the same configuration. In any of the embodiments in FIGS. 13A-17, all of the connectors in all of the sets of the plurality of sets of connectors may have an S-shape. In any of the embodiments in FIGS. 13A-17, all of the connectors in all of the sets of the plurality of sets of connectors may have a reverse (or inverted) S-shape. In any of the scaffolds shown in FIGS. 13A-17, all of the connectors in a first set of connectors may have a S shape. In any of the scaffolds shown in FIGS. 13A-17, a second set of connectors that is circumferentially adjacent to the first set of connectors may all have an inverted S shape. In any of the scaffolds shown in FIGS. 13A-17, S shape/ inverted S shape connectors may alternate around the circumference of the expandable scaffold.

In any of the embodiments in FIGS. 13A-17, a first set of connectors that extend in a first circumferential direction from a first axially extending element may extend from the first axially extending element at axial locations that are different from the axial locations at which a second set of connectors extend from the first axially extending element in a second circumferential direction (i.e., the connectors have ends that are axially offset).

In any of the embodiments in FIGS. 13A-17, the expandable scaffold may include a transition region connecting a first axially extending element with a strut, optionally wherein the transition region is considered part of the expandable scaffold. A transition region may also connect the strut with a second axially extending element, the second axially being circumferentially adjacent to the first axially extending around the blood conduit. In any of the scaffolds shown in FIGS. 13A-17, the expandable scaffold may extend along substantially the entire length of the conduit. In any of the scaffolds shown in FIGS. 13A-17, the expandable scaffold may extend along less than 50% of the length of the expandable impeller housing. In any of the embodiments in FIGS. 13A-17, the expandable scaffold may extend only in a region of the expandable housing in which an impeller is disposed.

In any of the embodiments in FIGS. 13A-17, the expandable impeller housing may include a second expandable scaffold axially spaced from the first expandable scaffold. A second expandable scaffold may have an expanded configuration with a second plurality of axially extending elements that are axially extending over at least 50% of a length of the second expandable scaffold and wherein the second expandable scaffold may also include a plurality of sets of connectors, each set of connectors extending circumferentially between first and second circumferentially adjacent axially extending elements. A second expandable scaffold may include any features set forth in any of the claims or described elsewhere herein. In any of the scaffolds shown in FIGS. 13A-17, the expandable scaffold may be unitary, that is, made from a single piece of starting material.

FIGS. 18A and 18B illustrate an exemplary scaffold 450 comprising a plurality of axially extending elements 452 (eight in this example). Scaffold 450 includes a proximal scaffold 460, a central scaffold 462, and distal scaffold 464. In this example axially extending elements 452 are linear. Central scaffold 462 is connected to proximal scaffold 460 and to distal scaffold 464 in this example, and in particular, is unitary with them in this example. FIG. 18B illustrates an expanded configuration, and FIG. 18A illustrates an as-cut flat illustration of the scaffold. The axially extending elements 452 that are labeled in FIG. 18B are circumferentially adjacent axial elements. Adjacent axially extending elements are connected by a plurality of circumferential connectors 451, which in this example have general S or inverse-S configurations, which include at least one bend formed therein. As shown, each circumferential connector is circumferentially adjacent to another circumferential connectors, and together they extend around the blood conduit. In this example, as shown, circumferentially adjacent circumferential connectors are displaced axially relative to one another. For example, circumferential connectors 451' are axially displaced (or axially offset) relative to circumferential connectors 451". Axially displaced or axially offset in this context refers to proximal ends of the connectors being axially offset, distal ends of the connectors being axially offset, or both. In this example, a section of each one of the axially extending elements connects adjacent circumferential connectors that are axially displaced. For example, section 453 of one of the axially extending elements 452 connects circumferential connector 451' and 451", which creates the axially displaced nature of the circumferentially adjacent circumferential connectors. In this example, distal ends of connectors 451" are further distally than the distal ends of the circumferentially adjacent connectors 451', as shown. FIGS. 18A and 18B also illustrate a first group of a plurality of circumferential connectors having a first axial position, and a second group of the plurality of circumferential connectors having a second axial position, wherein the first and second axial positions alternate circumferentially around the blood conduit, as shown.

FIGS. 19A and 19B illustrate an exemplary scaffold 470. Scaffold 470 includes a plurality of axially extending elements 472, which are linear is sections but are not linear along the entire scaffold 470 length. Scaffold 470 also includes connectors 471 that circumferentially connect circumferentially adjacent axial elements 472. Connectors 471 includes peaks that are oriented, or point, axially, and in this example may be oriented distally or proximally Scaffold 470 includes a proximal scaffold, a central scaffold, and a distal scaffold that are connected, and in this example are unitary, just as with the scaffold in FIGS. 18A and 18B. Both the proximal scaffold, central scaffold, and distal scaffold comprise a plurality of linear axially extending elements spaced apart around the blood conduit, wherein first and second adjacent linear axially extending elements are each connected by a circumferential connector having at least one bend formed therein. The circumferential connectors defining a plurality of circumferential connectors around the blood conduit, and wherein circumferentially adjacent circumferential connectors of the plurality of circumferential connectors are displaced axially relative to one another. Like in FIGS. 18A and 19B, a section 473 of each one of the axially extending elements (in this example linear) connects circumferentially adjacent circumferential connectors that are axially displaced, as shown. FIGS. 19A and 19B illustrate a first group of a plurality of circumferential connectors having a first axial position, and wherein a second group of the plurality of circumferential connectors have a second axial position, wherein the first and second axial positions alternate circumferentially around the blood conduit. In this embodiment, the proximal, central, and distal scaffolds are generally the same configuration (except the ends of the distal and proximal scaffolds).

Scaffold 470 also includes second region 477 that is axially adjacent first region 476, wherein second region 477 comprises a plurality of peaks 478 that are shown oriented orthogonally relative to a long axis of the blood conduit (membrane not shown for clarity). In this example, each of the plurality of peaks 478 is an extension of one of the axially extending elements 472 in the first region 476, as shown. Scaffold 470 also includes third region 479 that is axially adjacent second region 477, the third region 470 comprising a second plurality of linear axially extending elements as shown that are spaced apart around the blood conduit, and a second plurality of circumferential connectors 471, where the second region 477 joins the first region 476 and third region 479. In this example this pattern continues along the length of the scaffold.

FIGS. 20A and 20B illustrate exemplary scaffold 500, with FIG. 20B showing the expanded configuration and FIG. 20A illustrating a flattened non-expanded configuration. Features that are shown in FIGS. 20A and 20B that are the same as features shown in other scaffolds herein may be expressly included in this embodiment even if not described herewith. Scaffold 500 includes proximal scaffold 510, central scaffold 520 and distal scaffold 530, which are unitary in this embodiment. In this embodiment the central scaffold 520 has a pattern and configuration such that it is less stiff in response to a radially inward force than proximal scaffold 510 and distal scaffold 530. Proximal scaffold 510 may be a proximal impeller scaffold, and distal scaffold 530 may be a distal impeller scaffold, within at least a portion of which a proximal impeller and a distal impeller may be disposed, respectively. Scaffold 500 central scaffold 520 has a pattern that is different than the pattern in scaffold sections 510 and 530. In this example, scaffold sections 510 and 530 have patterns that are substantially the same. Scaffold 500 includes circumferential connectors in proximal scaffold 510, central scaffold 520, and distal scaffold 530, as shown. For example, proximal scaffold 510 includes circumferential connectors 512, and distal scaffold 530 includes circumferential connectors 532. The circumferential connectors in scaffold 500 have the same configurations as circumferential connectors 451 in the scaffold 450 in FIGS. 18A and 18B, and all descriptions thereof are incorporated by reference with the circumferential connectors into all scaffold sections in scaffold 500. For example, circumferentially adjacent circumferential connectors are axially displaced (i.e., axially offset) relative to one another, which is described in more detail elsewhere herein. The circumferential connectors also have the S and inverse-S configurations, which is described with respect to other scaffolds herein. The central scaffold 520 in scaffold 500 also includes peaks 521 and 521', similar to peaks 478 in the scaffold in FIGS. 19A and 19B. A first plurality of peaks 521 have a first axial position, and a second plurality of peaks 521' have a second axial position, which can be seen clearly in FIG. 20A. The axial position alternates circumferentially around the scaffold, as shown. Peaks 521 and 521' extend from axially extending elements 522 like the scaffold in FIGS. 19A and 19B. The proximal scaffold and the distal scaffold do not include peaks in this embodiment. Axially extending elements 522 in the central scaffold section have a width that is greater than the width of the scaffold in peak 521 regions, as shown. This difference in width can provide the peak regions with greater flexibility, while the wider axially extending element provide sufficient radial support in the central scaffold. Any of the scaffold sections with the peaks may be considered a first region, and the axially adjacent sections with circumferential connectors and axially extending elements may be considered second regions, examples of which are described elsewhere herein. In this embodiment the axially extending elements are linear as shown, but may be curvilinear in other embodiments.

FIGS. 21A and 21B illustrate exemplary scaffold 550, with FIG. 21B showing the expanded configuration and FIG. 21A illustrating a flattened non-expanded configuration. Features that are shown in FIGS. 21A and 21B that are the same as features shown in other scaffolds herein may be expressly included in this embodiment even if not described herewith. Scaffold 550 includes proximal scaffold 560, central scaffold 570 and distal scaffold 580, which are unitary in this embodiment. Proximal scaffold 560 may be a proximal impeller scaffold, and distal scaffold 580 may be a distal impeller scaffold, within at least a portion of which a proximal impeller and a distal impeller may be disposed, respectively. Scaffold 550 central scaffold 570 has a pattern that is different than the pattern in scaffold sections 560 and 580. In this example, scaffold sections 560 and 580 have patterns that are substantially the same. Scaffold 550 includes circumferential connectors in proximal scaffold 560, central scaffold 570, and distal scaffold 580, as shown. For example, proximal scaffold 560 includes circumferential connectors 562, and distal scaffold 580 includes circumferential connectors 582. The circumferential connectors in scaffold 550 have the same configurations as circumferential connectors 451 in the scaffold 450 in FIGS. 18A and 18B, and all descriptions thereof are incorporated by reference with the circumferential connectors into all scaffold sections in scaffold 550. For example only, circumferentially adjacent circumferential connectors are axially displaced (i.e., axially offset) relative to one another, which is described in more detail elsewhere herein. The circumferential connectors also have the S and inverse-S configurations, which is described with respect to other scaffolds herein. Elements 571 in the central scaffold extend into the proximal and distal scaffold sections as shown, forming linear axially extending elements in the proximal and distal scaffolds. Axially extending elements 561 in proximal scaffold 560 do not extend into the central scaffold, as shown. Similarly, axially extending elements 581 in distal scaffold 580 do not extend into the central scaffold, as shown. Elements 571 in the central scaffold 570 have helical configurations as shown. Adjacent elements 571 are connected with connectors 572 as shown. Connectors 572 may have any characteristics of any circumferential connectors herein, such as the alternating S and inverse-S configurations. FIG. 21A illustrates a flattened non-expanded configuration, and the scaffold 550 may be formed into the configuration shown in FIG. 21B, such as by twisting the ends relative to one another and setting the scaffold in the configuration shown in FIG. 21B.

FIGS. 22A and 22B illustrate exemplary scaffold 600, with FIG. 22B showing the expanded configuration and FIG. 22A illustrating a flattened non-expanded configuration. Features that are shown in FIGS. 22A and 22B that are the same as features shown in other scaffolds herein may be expressly included in this embodiment even if not described herewith. Scaffold 600 includes proximal scaffold 610, central scaffold 620 and distal scaffold 630, which are unitary in this embodiment. Proximal scaffold 610 may be a proximal impeller scaffold, and distal scaffold 630 may be a distal impeller scaffold, within at least a portion of which a proximal impeller and a distal impeller may be disposed, respectively. Scaffold 600 central scaffold 620 has a pattern that is different than the pattern in scaffold sections 610 and 630. In this example, scaffold sections 610 and 630 have patterns that are substantially the same. Scaffold 600 includes circumferential connectors in proximal scaffold 610, central scaffold 620, and distal scaffold 630, as shown. For example, proximal scaffold 610 includes circumferential connectors 612, and distal scaffold 630 includes circumferential connectors 632. The circumferential connectors in the proximal and distal sections of scaffold 600 have the same configurations as circumferential connectors 451 in the scaffold 450 in FIGS. 18A and 18B, and all descriptions thereof are incorporated by reference with the circumferential connectors into all scaffold sections in scaffold 600. For example only, circumferentially adjacent circumferential connectors are axially displaced (i.e., axially offset) relative to one another, which is described in more detail elsewhere herein, and connect axially extending elements 611 and 631, respectively. The circumferential connectors also have S and inverse-S configurations, which is described with respect to other scaffolds herein. Axially extending elements 621 in the central scaffold extend into the proximal and distal scaffold sections as shown, wherein the elements 621 are linear axially extending elements in the proximal and distal scaffolds as well as the central scaffold. Axially extending elements 611 in proximal scaffold 610 do not extend into the central scaffold, as shown. Similarly, axially extending elements 631 in distal scaffold 630 do not extend into the central scaffold, as shown. Elements 621 in the central scaffold 620 have axially extending linear configurations as shown. Central scaffold 620 includes axially extending elements 621 that are connected by circumferential connectors. The circumferential connectors include a plurality of axially extending elements 624, each of which connect circumferentially adjacent circumferential connectors 622, as shown. When scaffold 600 is expanded to the configuration shown in FIG. 22B, the circumferential connectors assume the configuration shown, wherein elements 624 are no longer purely axially extending, such that they form an angle with a long axis of the scaffold, as shown.

FIGS. 23A and 23B illustrate exemplary scaffold 650, with FIG. 23B showing the expanded configuration and FIG. 23A illustrating a flattened non-expanded configuration. Features that are shown in FIGS. 23A and 23B that are the same as features shown in other scaffolds herein may be expressly included in this embodiment even if not described herewith. Scaffold 650 includes proximal scaffold 660, central scaffold 670 and distal scaffold 650, which are unitary in this embodiment. Proximal scaffold 660 may be a proximal impeller scaffold, and distal scaffold 650 may be a distal impeller scaffold, within at least a portion of which a proximal impeller and a distal impeller may be disposed, respectively. Scaffold 650 central scaffold 670 has a pattern that is different than the pattern in scaffold sections 660 and 680. In this example, scaffold sections 660 and 680 have patterns that are substantially the same. Scaffold 650 includes circumferential connectors in proximal scaffold 660, central scaffold 670, and distal scaffold 680, as shown. For example, proximal scaffold 660 includes circumferential connectors 662, and distal scaffold 650 includes circumferential connectors 682. The circumferential connectors in the proximal and distal sections of scaffold 650 have the same configurations as circumferential connectors 451 in the scaffold 450 in FIGS. 18A and 18B, and all descriptions thereof are incorporated by reference with the circumferential connectors into all scaffold sections in scaffold 650. For example only, circumferentially adjacent circumferential connectors are axially displaced (i.e., axially offset) relative to one another, which is described in more detail elsewhere herein, and connect axially extending elements 661 and 681, respectively. The circumferential connectors also have S and inverse-S configurations, which is described with respect to other scaffolds herein. Axially extending elements 671 in the central scaffold extend into the proximal and distal scaffold sections as shown, wherein the elements 671 are linear axially extending elements in the proximal and distal scaffolds as well as the central scaffold. Axially extending elements 661 in proximal scaffold 660 do not extend into the central scaffold, as shown. Similarly, axially extending elements 681 in distal scaffold 650 do not extend into the central scaffold, as shown. Elements 671 in the central scaffold 670 have axially extending linear configurations as shown. Central scaffold 670 includes axially extending elements 671 that are connected by circumferential connectors. The circumferential connectors include a plurality of axially extending elements 674, each of which connect circumferentially adjacent circumferential connectors 672, as shown. When scaffold 650 is expanded to the configuration shown in FIG. 23B, the circumferential connectors 672 assume the configuration shown, wherein elements 674 are no longer purely axially extending, such that they form an angle with a long axis of the scaffold, as shown. Elements 674 in FIG. 23A are formed by removing material axially disposed between axially adjacent elements 674.

FIGS. 24A and 24B illustrate exemplary scaffold 700, with FIG. 24B showing the expanded configuration and FIG. 24A illustrating a flattened non-expanded configuration. Features that are shown in FIGS. 24A and 24B that are the same as features shown in other scaffolds herein may be expressly included in this embodiment even if not described herewith. For example, scaffold 700 is the same in some ways to the scaffolds shown in FIGS. 19A, 19B, 20A and 20B. Scaffold 700 includes proximal scaffold 710, central scaffold 720 and distal scaffold 730, which are unitary in this embodiment. Proximal scaffold 710 may be a proximal impeller scaffold, and distal scaffold 730 may be a distal impeller scaffold, within at least a portion of which a proximal impeller and a distal impeller may be disposed, respectively. Scaffold 700 central scaffold 720 has a pattern that is different than the pattern in scaffold sections 710 and 730. In this example, scaffold sections 710 and 730 have patterns that are substantially the same. Scaffold 700 includes circumferential connectors in proximal scaffold 710, in central scaffold 720, and in distal scaffold 730, as shown. For example, proximal scaffold 710 includes circumferential connectors 712, and distal scaffold 730 includes circumferential connectors 732. The circumferential connectors in the proximal and distal sections of scaffold 700 have the same configurations as circumferential connectors 451 in the scaffold 450 in FIGS. 18A and 18B, and all descriptions thereof are incorporated by reference with the circumferential connectors into all scaffold sections in scaffold 700. For example only, circumferentially adjacent circumferential connectors are axially displaced (i.e., axially offset) relative to one another, which is described in more detail elsewhere herein, and connect axially extending elements 711 and 731, respectively. The circumferential connectors also have S and inverse-S configurations alternating circumferentially around the scaffold, which is described with respect to other scaffolds herein. Scaffold 700 includes a plurality of axially extending elements 711, which are linear in sections but do not extend along the entire length of scaffold 700. Scaffold 700 also includes circumferential connectors 712 that circumferentially connect circumferentially adjacent axial elements 711. The proximal scaffold, central scaffold, and distal scaffold comprise a plurality of linear axially extending elements 711, 721, and 731, respectively, that are circumferentially spaced apart around the respective scaffold section, wherein first and second adjacent linear axially extending elements are each connected by a circumferential connector 712, 722, and 732, respectively, having at least one bend formed therein. The circumferential connectors define a plurality of circumferential connectors around the scaffold, and wherein circumferentially adjacent circumferential connectors of the plurality of circumferential connectors are displaced axially relative to one another, as shown and described elsewhere herein. As is the case in FIGS. 18A and 19B, a section of each one of the axially extending elements (in this example linear elements) connects circumferentially adjacent circumferential connectors that are axially displaced, as shown. FIGS. 24A and 24B illustrate a first group of a plurality of circumferential connectors having a first axial position, and wherein a second group of the plurality of circumferential connectors have a second axial position, wherein the first and second axial positions alternate circumferentially around the scaffold.

Scaffold 700 also includes a second region that is axially adjacent a first region, wherein the second region comprises a plurality of peaks 724 that are shown oriented orthogonally relative to a long axis of the scaffold 700. In this example, each of the plurality of peaks 724 is an extension of one of the axially extending elements 721, as shown. Scaffold 700 also includes a third region that is axially adjacent the second region, the third region comprising a second plurality of linear axially extending elements as shown that are spaced apart around the scaffold, and a second plurality of circumferential connectors 722, where the second region joins the first region and third region. In this embodiment, the second region includes first convex section 725 and second convex section 727, connected at location 729.

FIGS. 25A and 25B illustrate an exemplary scaffold 750, which in this example includes a proximal scaffold 760, central scaffold 770 and distal scaffold 780, which are unitary. Scaffold 750 is similar in several ways to scaffold 700 in FIGS. 24A and 24B, the disclosure of which is completely incorporated by reference in the description of FIGS. 25A and 25B, any features of which may be included in scaffold 750. One difference is that scaffold 750 central scaffold 770 includes a first region that includes peaks 774, wherein the first region includes sections 775 and 777 connected at location 779, wherein sections 775 and 777 create a smoother curvilinear region than sections 725 and 727 in scaffold 700. An additional difference is that scaffold 750 includes proximal and distal scaffolds that both include mirrored sections, such as sections 763 and 765 as shown in FIG. 25B. The mirrored aspect refers to axially adjacent connectors 762 in section 763 that are mirrored with respect to connectors 762 in section 765. The same mirrored aspect is shown in distal scaffold 780. The mirrored sections in proximal scaffold 760 are closer to central scaffold 770 than the mirrored sections in distal scaffold 780, as shown. In alternative embodiments, mirrored sections in a distal scaffold may be closer to a central scaffold than mirrored sections in a proximal scaffold. The description of all other aspects of scaffolds herein, including axially extending elements and circumferential connectors, are incorporated by reference herein into the scaffold 750. FIG. 25B shows a flat expanded configuration, while FIG. 25A shows a flat non-expanded configuration.

FIGS. 26A and 26B illustrate scaffold 800, which as shown includes many of the same features as scaffold 750 shown in FIGS. 25A and 25B. FIG. 26A illustrate a flattened unexpanded configuration, while FIG. 26B illustrates transition region 801 of scaffold 800 called out in FIG. 26A. A difference between the scaffolds is that in FIGS. 26A and 26B, proximal scaffold 810 includes mirrored sections that are further from central scaffold 820 than mirrored section in distal scaffold, as shown. FIG. 26B illustrates a transition region between proximal scaffold 810 and central scaffold 820. Scaffold 800 includes orthogonally oriented peaks 824 as described elsewhere herein. Scaffold first regions includes sections 825 and 827, which may be the same as sections 775 and 777 in scaffold 750. FIG. 26B illustrates the widths of axially extending elements 811 being greater than the widths of elements 821 in central scaffold, as shown. The thickness measurements are into the page in the figures (in the "z" direction), while the width measurements are in the plane of the page in the figures shown. One thickness "t" of element 811 is labeled for reference. As shown, the thickness "t" of element 811 is greater than the thickness of elements 821 in the central scaffold section.

FIGS. 27A and 27B illustrate exemplary scaffold 850, which is similar in several ways to scaffold 550 shown in FIGS. 21A and 21B. Scaffold 850 includes proximal scaffold 860, central scaffold 870 and distal scaffold 880, which in this embodiment may be unitary. Scaffold 850 central scaffold 870 includes helical elements 871 in the non-collapsed configuration (FIG. 27A) and the wrapped configuration (FIG. 27B). In this and any other embodiment herein the scaffold may be manufactured (e.g., including laser cutting of a tubular member) such that the expanded configuration is the configuration is which the scaffold is laser-cut from the tubular member. This is in contrast to any examples herein in which the scaffold is laser cut from a smaller diameter tubular member, and then expanded and set into an expanded configuration. In any of the embodiments herein, a laser cut diameter may be equal to a non-collapsed diameter to, for example without limitation, provide better concentricity. This may also allow coating of a membrane to adhere to struts and have a smoother inner diameter.

Proximal scaffold 860 and distal scaffold 880 have substantial the same configuration, but they are displaced circumferentially by circumferential spacing "CS" (labeled in FIG. 27A). Adjacent helical elements 871 are connected by connectors 872. All other similar aspect of other scaffolds herein may be incorporated herein, including, by way of example only, the axially offset nature of circumferentially adjacent circumferential connectors in proximal scaffold 860 and distal scaffold 880.

FIG. 27A illustrates exemplary distal and proximal struts extending axially from the scaffold, only one strut of which 865 is labeled. In this example there are four proximal and four distal struts. As shown, the struts are tapered and are wider at ends further from the scaffold, which may increase stability over the impellers compared to struts that have a constant width over their entire length. Any of the pump portions herein may include any number of struts that have the same configuration as struts 865.

In any of the embodiments herein, the scaffold may be cut from a tubular member that has an expanded scaffold diameter. In these embodiments, the tubular member has a diameter that is the same or substantially the same as the desired scaffold deployed configuration (un-sheathed). Alternatively, in any of the embodiments herein, the scaffold may be cut from a tubular member that has a non-expanded scaffold diameter. In this embodiments, the tubular member has a diameter less than a scaffold expanded diameter, and after being cut the scaffold may be expanded set in the expanded deployed configuration.

In any of the embodiments herein, a distal scaffold may have a length that is greater than a length of a proximal scaffold. In any of the embodiments herein, a distal scaffold may have a length that is less than a length of a proximal scaffold. In any of the embodiments herein, a distal scaffold may have a length that is the same as a length of a proximal scaffold.

In any embodiment herein, a central scaffold may have a length that is greater than a length of one or both of a proximal scaffold and a distal scaffold.

Any of the different scaffold sections herein may be connected with one or more welds, and may not be unitary with each other.

In any of the embodiments herein, any section or sections of the scaffold may have a thickness (measured radially between a scaffold inner diameter and a scaffold outer diameter) that is the same as or different than a thickness of any other section of the scaffold. For example, a thickness of a scaffold section may be decreased by electropolishing one or more sections more than other sections (which may include no electropolishing). Varying the thickness may be in addition to or alternative to varying the width, which may allow for more design options, as may be desired.

In any of the embodiments herein, an axial distance between proximal and distal scaffold sections may be from 30 mm to 50 mm, such as from 35 mm to 45 mm.

In any of the embodiments herein, the pump portion may be from 40 mm and 80 mm, such as from 50 mm to 70 mm, such as from 55 mm to 65 cm.

In any of the embodiments herein that include first and second impellers, an axial distance between impellers may be from 40 mm to 60 mm, such as from 45 mm to 55 mm.

In any of the embodiments herein, a diameter of the expanded (or non-collapsed) blood conduit may be from 6 mm to 8.5 mm, such as from 6 mm to 8 mm, such as from 6.5 mm to 7.5 mm.

In any of the embodiments herein, a diameter of any of the impellers when expanded may be from 5 mm to 7 mm, such as from 5.5 mm to 6.5 mm.

Some of the pump portions herein include a collapsible and expandable blood conduit, and one or more impellers at least partially disposed in the blood conduit when the pump portion is in an operational state. In some embodiments herein, the collapsible blood conduit includes a scaffold, which may extend along at least a portion of the length of the blood conduit and provide radial support to the blood conduit. In some embodiments herein a scaffold may be unitary along the blood conduit. In some embodiments different scaffold sections may not be unitary (formed from the same starting material), but they may be directly attached or connected to each other (e.g., welded directly together).

In some embodiments, axially adjacent scaffold sections may not be unitary and not connected to one other. They may still be coupled together due to their independent attachment to one or more membranes herein. In these examples, a central scaffold section may not be connected to one or both of a distal scaffold section or a proximal scaffold section. In some embodiments of the pump portions herein that only include a single impeller, a central scaffold section may not be connected to one or both scaffold sections that may be axially adjacent the central scaffold section.

FIGS. 28A and 28B illustrates an exemplary collapsible blood conduit 900 of a pump portion, shown expanded (not in a collapsed state). Blood conduit 900 includes a collapsible scaffold that includes a central scaffold section 902, a proximal scaffold section 904 and a distal scaffold section 906. Proximal and distal in this context does not necessarily impart that they are the most distal or most proximal scaffold section, although they may be. Proximal and distal in this context refers generally to relative position with respect to an axially central scaffold section. In this example, axially central scaffold section 902 is not connected to and not unitary with either proximal scaffold section 904 or distal scaffold section 906. The proximal, central, and distal scaffold sections are each individually connected to one or more membrane layers, which are described in more detail elsewhere herein.

The pump portion 900 in FIGS. 28A and 28B may be considered similar to other pump portions herein, such as the pump shown in FIG. 2, FIGS. 3A-4, FIG. 9, in that the pump portion may be considered to include proximal and distal expandable impeller baskets, examples of which are described herein. For example, the pump portion 340 in FIGS. 3A-3D includes exemplary proximal scaffold or basket 343 and distal scaffold or basket 344. Proximal scaffold section 904 may be considered similar to proximal scaffold 343, and distal scaffold section 906 may be considered similar to distal scaffold 344. Pump portion 900 may thus be considered similar in any other way to pump portion 340 that is described herein, while further comprising a central scaffold section 902 that is not directly attached to the proximal and distal scaffold sections. The pump membrane that forms the blood conduit may be comprised of one or more layers of membrane materials, which is described in more detail herein.

In alternatives to the pump portion shown in FIGS. 28A and 28B, the pump portion may not include any baskets as that term is used herein, but the central scaffold may still be non-unitary and not connected to one or both of proximal and distal scaffold sections. For example, pump 900 may alternatively exclude baskets with distal and proximal struts, similar to the scaffold shown in FIG. 11. Additionally, the scaffold in FIG. 11 may alternatively include discontinuities between a central scaffold section and one or both of a proximal scaffold and a distal scaffold such that the central scaffold is not unitary and not connected to the proximal and/or distal scaffold sections. Any of the scaffolds herein may thus be modified to include discontinuities between a central scaffold section and one or both of a proximal scaffold and a distal scaffold such that the central scaffold is not unitary and not connected to the proximal and/or distal scaffold sections.

FIGS. 28A and 28B illustrates a pump portion with more than one impeller, but the pump portion may include a single impeller, such as a proximal impeller, or a distal impeller. If the pump portion includes a single impeller, the axial location of the impeller may be different than that shown in FIGS. 28A and 28B. For example, a proximal impeller may be disposed completely within the blood conduit. The impellers in FIGS. 28A and 28B are illustrative, and may be replaced with any of suitable impellers herein or suitable impellers general known in the art.

Any of the central scaffold sections herein may be connected or unitary to one of a distal scaffold section or a proximal scaffold section, and not unitary and not connected with the other of the distal and proximal scaffold sections.

Any of the central scaffold sections herein may have a different scaffold configuration than one or both of a proximal scaffold section and distal scaffold sections. For example, in the example in FIGS. 28A and 28B, central scaffold section 902 has a different overall configuration than both the proximal section 904 and the distal section 906. In FIGS. 28A and 28B, the proximal and distal scaffold sections may have the same or similar configurations as any of the proximal and distal scaffold sections in, for example, as shown in FIGS. 13A-13C, 14A and 14B, 15A and 15B, 16, 17, 18A and 18B, 19A and 19B, 20A and 20B, 21A and 21B, 22A and 22B, 23A and 23B, 24A and 24B, 25A and 25B, 26A and 26B, or 27A and 27B, the descriptions of which are incorporated by reference into the example in FIGS. 28A and 28B. The proximal and distal scaffold sections may have the same configuration, similar configurations, or different overall configurations. In this context, the configurations are compared in their totalities, including repeating sections and overall structure from proximal end to distal end. The example in FIGS. 28A and 28B illustrates proximal and distal scaffold sections that are the same.

In alternatives to any embodiments herein, a central scaffold section may be connected to or unitary with one of a proximal scaffold and a distal scaffold, but not the other. For example, with reference to FIG. 28A, in an alternative scaffold section 902 may be unitary with or connected to scaffold section 906 or scaffold section 904, but not the other.

Any of the scaffolds or scaffold sections herein may be understood to have proximal and distal ends. For example, proximal end 901 and distal end 903, respectively, of central scaffold 902 are shown in FIGS. 28A and 28B. P in FIG. 28A refers to a proximal direction, while D refers to a distal direction. Inflow I and outflow O are also labeled. Any other aspect of any pump portion herein may be incorporated into pump portion 900 including any of its alternatives. Exemplary proximal impeller 920 and distal impeller 930 are also shown in FIGS. 28A and 28B, as is exemplary drive assembly 940, which is in rotational communication with a motor (not shown) that drives the rotation of the one or more impellers.

Pump portions herein generally have central regions that are generally more flexible than one or both of proximal impeller regions and distal impeller regions, advantages of which are described elsewhere herein. In general, the central scaffold sections herein are more flexible than proximal and distal impeller sections. For example, central scaffold 902 shown in FIGS. 28A and 28B may be considered to have a similar configuration to the central scaffold sections shown in FIGS. 25A-26B (the descriptions of which are fully incorporated by reference), which may provide greater flexibility to the central scaffold than flexibilities of the proximal and distal scaffold sections. Additionally, at least one of proximal end 901 and distal end 903 of central scaffold section is not connected to an adjacent scaffold sections, which may impart additional flexibility to the blood conduit in the vicinity of the central scaffold section.

In the example shown in FIGS. 28A and 28B, pump portion 900 includes a proximal impeller basket, a scaffold portion of which defines proximal scaffold section 904. Pump portion 900 also includes a distal impeller basket, a scaffold portion of which defines distal scaffold section 906. The proximal basket also includes proximal basket proximal struts 908 and proximal basket distal struts 910, additional exemplary details of which are described elsewhere herein. The distal basket includes distal basket proximal struts 912 and distal basket distal struts 914, additional exemplary details of which are described elsewhere herein. Pump portion 900 may incorporate any suitable feature or aspect of the any of the expandable baskets described herein.

During collapse of the pump, one or more of the baskets ends, such as a bearing housing, may move axially relative to the drive assembly 940 or other radially inner component to facilitate collapse, additional exemplary details of which is described elsewhere herein. Additionally, any of the struts herein may have free ends that are coupled to, connected to, or unitary with a central hub, central assembly, or bearing assembly, examples of which are shown and described herein.

FIGS. 29A-29E illustrate an exemplary scaffold 2950, which is similar to scaffold 850 shown in FIGS. 27A and 27B but with a different scaffold pattern. In this and any other embodiment herein, the scaffold 2950 may be manufactured (e.g., including laser cutting of a tubular member) such that the expanded configuration is the configuration in which the scaffold is laser-cut from the tubular member. In this example, proximal and distal ends of the scaffold comprise free ends, which include a plurality of free strut ends.

FIG. 29A illustrates a flattened view of the scaffold. The scaffold 2950 includes a proximal scaffold section 2960, a central scaffold section 2970 and a distal scaffold section 2980. The proximal section 2960 may be configured to enclose a proximal impeller, and the distal section 2980 may be configured to enclose a distal impeller. In other embodiments, the scaffold is configured to enclose only a single impeller, such as only a proximal impeller in proximal section 2960 and no distal impeller in distal section 2980. In some cases, the proximal and/or distal impellers have the same diameter and axial length. In some cases, the proximal and/or distal impellers have different diameters and/or axial lengths. The scaffold 2950 may be unitary and may be made of a single piece of material (e.g., metal). For example, the scaffold 2950 includes a series of axially extending elongate elements 2911 that extend from the proximal section 2960, through the central section 2970, and to the distal section 2980. A first set of the elongate elements 2911 form proximal struts 2952 at a proximal end of the scaffold 2950. Likewise, a second set of the elongate elements 2911 form distal struts 2951 at a distal end of the scaffold 2950. The axially extending elongate elements 2911 may be connected by connector elements 2912 in the proximal section 2960 and by connector elements 2922 in the distal section 2980.

In this example, the proximal section 2960 and distal section 2980 each includes ten axially extending elongate elements 2911. This arrangement may provide the scaffold 2950 more radial stiffness compared to the proximal section 860 and the distal section 880 of FIGS. 27A and 27B, which each include eight axially extending elongate elements. Changes that impart greater radial stiffness may also increase bending stiffness. Thus, the proximal section 2960 and distal section 2980 of scaffold 2950 in FIGS. 29A-29E may have greater lateral bending stiffness compared to the proximal section 860 and the distal section 880 of scaffold 850 in FIGS. 27A and 27B. Bending stiffness can refer to the ability of the scaffold 2950, or a section of the scaffold 2950, can withstand deformation when a lateral force is applied to a side of the scaffold, or a section of scaffold 2950.

Note that, in this case, a greater number of extending elongate elements 2911 in the scaffold 2950 results in a greater number of proximal struts 2952 and distal struts 2951 compared to the scaffold 850 of FIGS. 27A and 27B. Specifically, the scaffold 2950 includes five proximal struts 2952 and five distal struts 2951, whereas scaffold 850 includes four proximal struts and four distal struts. This arrangement may give the scaffold 2950 more radial rigidity than scaffold 850 in this region. In some cases, one or more of the proximal struts 2952 and one or more of the distal struts 2951 may include cutouts or recesses 2918 (optionally regions of decreased relatively circumferential width) that provide room or accommodates for the presence of one or more sensing elements (e.g., one or more of a pressure sensor and/or pressure sensor housing) on a central hub of the blood pump assembly.

In the central section 2970 of the scaffold 2950, the elongate elements 2911 may be axially skewed to have helical or spiral shapes that wrap around a central or long axis of the scaffold 2950. This helical or spiral arrangement of the elongate elements in the central section may allow the central section 2970 to be more laterally flexible and bendable compared to the proximal section 2960 and distal section 2980. This aspect may allow the central section 2970 to deflect when a lateral force is applied on a side of the blood conduit, for example, as the blood conduit traverses through the patient's blood vessels and/or within the chambers of the heart. For example, the central section 2970 may be configured to laterally bend upon a lateral force applied to the distal section 2980 and/or the proximal section 2960. In some cases, it may be desirable for the central section 2970 to laterally bend as the blood conduit traverses the ascending aorta and temporarily assume a bent configuration when the blood conduit is positioned across an aortic valve, as described herein. The helical or spiral pattern in the central section may allow lateral bending without collapsing of the inner lumen of the central section 2970, thereby allowing blood to flow through the central section 2970. Once the lateral bending force is released, the central section 2970 may take on its original straight shape where the proximal and distal sections 2960/2980 are axially aligned. In some examples, the scaffold 2950 may be made of a shape memory material (e.g., nitinol), where the scaffold 2950 is shape set to the expanded configuration and the proximal section 2960, central section 2970 and distal section 2980 are axially aligned (e.g., central section 2970 is unbent). Thus, once the scaffold 2950 lateral bending force is released, the scaffold 2950 may return to the original shape set state.

In the example of scaffold 2950, the helical or spiral portions 2971 of the elongate elements 2911 within the central section 2970 are not connected to each other by intervening connectors (e.g., connectors 872 of FIGS. 27A and 27B). Thus, the helical or spiral portions 2971 within the central section 2970 may be circumferentially uncoupled to one another by the scaffold 2950. This aspect may provide greater lateral flexibility to the central section 2970. In addition, the width of the helical portions 2971 of the elongate elements may be smaller than the widths of the elongate elements 2911 within the proximal section 2960 and the distal section 2980. This arrangement may provide the central section 2970 more flexibility compared to the proximal section 2960 and the distal section 2980, which may also contribute to the lateral flexibility of the central section 2970. The central section 2970 may be adapted to bend to a greater extent, or have a higher degree of bend than both proximal section 2960 and distal section 2980 in response to a lateral force applied to distal section 2980. Central section 2970 may be positioned across an aortic valve when in use, and the flexibility of central section 2970 may help central section 2970 deform or bend when placed across the valve.

In some cases, the central section 2970 is sufficiently flexibility to cause the central section 2970 to assume a bent configuration when the blood conduit is positioned across a valve (e.g., aortic valve) with the central section 2970 disposed at the location of the valve leaflets. The bent configuration may cause a rotational axis of the proximal impeller to be dis-aligned with (e.g., be non-parallel to) a rotational axis of the distal impeller (e.g., similar to that shown in FIG. 4).

The proximal section 2960, the central section 2970 and/or the distal section 2980 may have different patterns of structural elements, which may provide different stiffnesses to the proximal section 2960, the central section 2970 and/or the distal section 2980. For example, the connector elements 2912 in the proximal section 2960 and the connector elements 2922 in the distal section 2980 are arranged in annular rows around a central axis of the tubular scaffold to provide radial and/or bending stiffness to the respective sections. In this case, the proximal section 2960 includes more connector elements 2912 (four annular rows) than the distal section 2980 (three annular rows), thereby providing greater radial and/or bending stiffness to the proximal section 2960 relative to the distal section 2980.

The spacings between the scaffold elements (e.g., connector elements 2912/2922 and elongate elements 2911) may also be associated with the radial and/or bending stiffness of a scaffold section. For example, axially adjacent connector elements 2912 may be axially closer to one another in proximal section 2960 than in distal section 1980, which may help impart greater relative stiffness (e.g., radial and/or bending stiffness) in proximal section 2960. In this example, the proximal section 2960 has a denser scaffold pattern than the distal section 2980, resulting in the proximal section 2960 having a greater radial and/or bending stiffness than the distal section 2980. For instance, connector elements 2912 that circumferentially connect the axially extending elongate elements 2911 within the proximal section 2960 may be a first distance 2934 apart, and connector elements 2922 that connect the axially extending elongate elements 2911 within the distal section 2980 may be a second distance 2936 apart, where the first distance 2934 is smaller than the second distance 2936. This may result in the apertures 2966 between the scaffold elements within the proximal section 2960 to be smaller than apertures 2968 between the scaffold elements within the distal section 2980.

For any of the scaffolds described herein, a scaffold section having a pattern with a greater cumulative area of spacing (e.g., spacings between scaffold elements) may be referred to as "loosely packed" and a scaffold section having a pattern with a lesser cumulative area of spacing may be referred to as "tightly packed." For example, the proximal section 2960 may be characterized as having a more tightly packed scaffold pattern than the distal section 2980. A section having a more tightly packed scaffold pattern may be associated with having a greater radial and/or bending stiffness compared to a section having a more loosely packed scaffold pattern.

In some examples, a vertical spacing 2933 between the elongate elements 2911 may be within a range bounded by any two of the following values: 1 mm, 1.5 mm, 2 mm, 2.5 mm, 3.0 mm, 3.5 mm, 4 mm, 4.5 mm and 5 mm.

In some examples, the first distance 2934 between connector elements 2912 of the proximal section 2960 may be within a range bounded by any two of the following values: 3.0 mm, 3.5 mm, and 4.0 mm.

In some examples, the second distance 2936 between connector elements 2922 of the distal section 2980 may be within a range bounded by any two of the following values: 4.0 mm, 4.5 mm, and 5.0 mm.

The proximal section 2960 and the distal section 2980 may have different axial lengths. In this example, the proximal section 2960 may have an axial length 2975 that is greater than an axial length 2977 of the distal section 2980.

In some cases, the axial length 2975 of the proximal section 2960 may be greater than the axial length 2977 of the distal section 2980 by about 5% to 20%. The axial length 2979 of the central section 2970 may be greater than the axial length 2975 of the proximal section 2960 and/or the axial length 2977 of the distal section 2980. The axial length 2975 of the proximal section 2960 may be within a range bounded by any two of the following values: 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, and 25 mm. The axial length 2977 of the distal section 2980 may be within a range bounded by any two of the following values: 8 mm, 9 mm, 10 mm, 11 mm, 12 mm, 13 mm, 14 mm, 15 mm, and 16 mm. The axial length 2979 of the central section 2970 may be within a range bounded by any two of the following values: 22 mm, 23 mm, 24 mm, 25 mm, 26 mm, 27 mm, 28 mm, 29 mm, and 30 mm. The axial lengths 2961 of the proximal struts 2952 and/or the axial lengths 2981 of the distal struts 2951 may be within a range bounded by any two of the following values: 3 mm, 4 mm, 5 mm, 6 mm, 7 mm, 8 mm, 9 mm, and 10 mm.

In some cases, the axial length 2975 of the proximal section 2960 may be greater than the axial length 2977 of the distal section 2980 based differing forces that these sections are expected experience during operation within the patient. For example, a distal region 2967 of the proximal section may experience higher levels of radial inward forces compared to, for example, a proximal region 2969 of the distal section 2980. Having a longer proximal section 2960 may compensate for this expected greater inward radial force at the distal region 2967 of the proximal section 2960 to prevent collapse of this region of the scaffold 2950.

In some examples, a total axial length of the scaffold 2950, and any scaffolds described herein, may be within a range bounded by any two of the following values: 50 mm, 55 mm, 60 mm, 65 mm, 70 mm, 75 mm, and 80 mm.

In some cases, it may be beneficial for the proximal section 2960 to be radially stiffer and longer than the distal section 2980. For example, a particular placement of scaffold 2950 within the patient's body may cause the proximal section 2960 to experience a greater radially inward force (e.g., bending force) than the distal section 2980. For example, the proximal section 2960 may experience more bending forces within the ascending aorta compared to the distal section 2980 within the left ventricle. A stiffer and longer proximal section 2960 may reduce or prevent deformation of the proximal section 2960, thereby preventing the proximal impeller from contacting the walls of the blood conduit and/or maintaining the integrity of the blood conduit lumen for blood flow through the proximal portion of the scaffold 2950.

In some cases, an axial length 2979 of the central section 2970 is greater or less than the axial length 2975 of the proximal section 2960 and/or the axial length 2977 of the distal section 2980. In the example shown, the central section 2970 is greater than the axial length 2975 of the proximal section 2960 and the axial length 2977 of the distal section 2980.

The axially extending elongate elements 2911 within the central section 2970 may be angled relative to a longitudinal axis of the scaffold 2950. The angle $\ominus$ of the axially extending elongate elements 2911 within the central section 2970 may be non-parallel and non-orthogonal relative to the longitudinal axis of the scaffold 2950, forming the helical/spiral arrangement of the axially extending elongate elements 2911 around the central axis of the scaffold 2950.

The angle ⊖ may be determined based on several factors. For example, the angle ⊖ may be determined based on a desired degree of lateral bendability of the central section 2970. In some examples, the central section 2970 may be more laterally bendable with greater angles ⊖ and less laterally bendable with lesser angles ⊖.

The angle ⊖ may be also determined based on an expected axial force placed on the blood conduit as the blood pump traverses the patient's blood vessel/heart and/or as the blood conduit is sheathed and/or unsheathed. For example, it may be desirable for the central section 2970 to be axially rigid enough to at least partially axial deformation when such axial forces are applied to the blood conduit. In some examples, the central section 2970 may be more axially rigid with lesser angles ⊖ and less axially rigid with greater angles ⊖.

Another factor in determining angle ⊖ may include a degree of elongation of the blood conduit as it is collapsed during sheathing. The blood conduit may be longer when in the collapse state (e.g., when sheathed) compared to when in the expanded state (e.g., unsheathed). In some cases, the central hub on a proximal side and/or distal side of the scaffold 2950 may be configured to accommodate a change in length when the blood conduit transitions between the expanded and collapsed states. However, in some cases, it may be desirable to minimize such change in length, or keep the extent of change in length within a threshold amount. The extent to which the blood conduit may elongate may at least partially be based on angle ⊖. In some examples, greater angles ⊖ may be associated with a greater extent of elongation when the blood conduit is transitioned to the collapsed state compared to lesser angles ⊖.

In some examples, the angle ⊖ of the axially extending elongate elements 2911 within the central section 2970 may be within a range bounded by any two of the following values: 10 degrees, 15 degrees, 20 degrees, 25 degrees, 30 degrees, 35 degrees, 40 degrees, 45 degrees, 50 degrees, 55 degrees and 60 degrees. In some examples, the angle ⊖ may be within a range bounded by any two of the following values: 20 degrees, 25 degrees, 30 degrees, 35 degrees, 40 degrees and 45 degrees.

In some cases, widths of the axially extending elongate elements 2911 may vary along the length of the scaffold 2950. In some examples, a width 2927 of the axially extending elongate elements 2911 within the central section 2970 is less than a width 2928 of the axially extending elongate elements 2911 within the proximal section 2960 and/or a width 2929 of the axially extending elongate elements 2911 within the distal section 2980. The axially extending elongate elements 2911 in the proximal section 2960 and/or distal section 2980 may have a greater relative width to provide adequate support for the scaffold 2950 around respective impellers. The axially extending elongate elements 2911 in the central section 2970 may have a lesser relative width to provide lateral flexibility of the central section 2970 for lateral bending of the pump, for example, when positioned within a bent portion of a patient's anatomy. The lesser relative width axially extending elongate elements 2911 in the central section 2970 may alternatively, or additionally, allow for easier collapse of the scaffold thereby reducing sheathing strains.

FIG. 29B illustrates an exemplary blood conduit 2901 with the scaffold 2950 in an assembled state and in an expanded configuration. The proximal section 2960 of the scaffold 2950 encompasses or surrounds at least a portion of a proximal impeller 2920, and the distal section 2980 of the scaffold 2950 encompasses at least a portion of a distal impeller 2930. The scaffold 2950 also encompasses at least a portion of the driveshaft 2959 to which the proximal impeller 2920 and distal impeller 2930 are operationally coupled, including a central region of the drive shaft that extends between the impellers. The proximal struts 2952 may curve radially inward and be coupled to a proximal central hub 2986, and the distal struts 2951 may curve radially inward and be coupled to a distal central hub 2988. In some cases, each of the proximal central hub 2986 and the distal central hub 2988 at least partially house, or is adjacent to, a bearing assembly operatively coupled to the driveshaft 2959. The driveshaft 2959 may be configured to laterally bend as the scaffold laterally bends, and to maintain operational functionality (e.g., to rotate the impellers 2920 and 2930) as the driveshaft 2959 bends.

In the example shown, a membrane 2949 covers the apertures of the scaffold 2950 to form the blood conduit. In some cases, the membrane 2949 may cover at least a portion of, or all, the inner surfaces and/or outer surfaces of the scaffold 2950. For example, in some cases, the entire scaffold 2950 (including the inner diameter and outer diameter) may be covered with the membrane 2949. In some cases, the membrane 2949 may not cover the struts 2951/2952. In some cases, the membrane 2949 may cover at least a portion of the struts 2951/2952. The blood conduit may optionally include an inner membrane that extends over at least a portion of an inner surface of any of the scaffolds herein. The membrane 2949 may be made of a material that is sufficiently flexible to allow expansion and collapse of the blood conduit. The membrane 2949 may be made of any of the membrane materials described herein (e.g., biocompatible polymer material).

The membrane 2949 may be formed on the scaffold 2950 using any of a number of techniques. In some cases, the membrane 2949 may be applied using a spray-on technique. In some examples, the membrane 2949 may be formed in one or more layers. In some cases, the membrane 2949 is form by applying heat, pressure and/or vacuum to a membrane material.

FIG. 29C illustrates a proximal impeller region of the blood pump in a collapsed state and sheathed within an outer sheath 2955. The scaffold 2950 may be configured to be in a higher energy state when in the collapsed state such that a radially inward force is required, e.g., from the inner walls of the outer sheath 2955, to maintain the scaffold in the collapsed state. When the outer sheath 2955 is removed (e.g., by proximally pulling the outer sheath 2955 and/or distally pushing the blood pump), the scaffold 2950 may relax and transition to the lower energy expanded state. FIG. 29C shows how the connector elements 2912 may bend (optionally at ends of the connector elements 2912, which may be relatively more curved than central linear sections of the connector elements 2912, which may facilitate bending at the ends of connectors 2912) to bring the axially extending elongate elements 2911 radially inward and closer together, thereby collapsing the scaffold 2950. Likewise, when the scaffold 2950 is expanded, the connector elements 2912 may relax to their low energy state such that the connector elements 2912 may move radially outward and away from each other. Further, the struts 2952 may transition from the curved shape when the scaffold 2950 is in the expanded configuration to a straighter shape when the scaffold 2950 is in the collapsed configuration.

FIGS. 29D and 29E illustrate closeup views of proximal and distal portions of the scaffold 2950, respectively. As described above, a width 2928 of the axially extending elements 2911 within the proximal section 2960 and/or a width 2929 of the axially extending elements 2911 within the distal section 2980 may be greater than a width 2927 of the axially extending elements 2911 within the central section 2970. This may contribute to providing the greater radial and/or bending stiffness of the proximal section 2960 and/or the distal section 2980 relative to the central section 2970. In some embodiments, the width 2928 of the axially extending elements 2911 within the proximal section 2960 and/or a width 2929 of the axially extending elements 2911 within the distal section 2980 may be within a range bounded by any two of the following values: 0.2 mm, 0.25 mm, 0.3 mm, 0.35 mm, 0.4, and 0.45 mm. In some embodiments, the width 2927 of the axially extending elements 2911 within the central section 2970 may be within a range bounded by any two of the following values: 0.15 mm, 0.2 mm, 0.25 mm, and 0.3 mm. In some embodiments, the width 2928 and/or 2929 may be greater than the width 2927 by a percentage ranging anywhere between about 2% to 100%.

The transition between the width 2928 and/or 2929 and the width 2927 may occur within a transition region 2947 between the central section 2970 and the proximal section 2960 or distal section 2980. The axially extending elements 2911 within the transition region 2947 may have curved shapes so that the axially extending elements 2911 can transition from being parallel (with respect to the central axis of the blood conduit) within the proximal section 2960 or distal section 2980 to the helical configuration within the central section 2970. In some embodiments, the radius of curvature 2944 of each axially extending element 2911 within the transition region 2947 may be within a range bounded by any two of the following values: 0.1 inches, 0.2 inches, 0.3 inches, 0.4 inches, and 0.5 inches. In some embodiments, the length of the transition region 2947 along the axially extending element 2911 may be within a range bounded by any two of the following values: 0.10 inches, 0.15 inches, 0.20 inches, and 0.25 inches.

The shape and size of the connector elements 2912 (in the proximal section 2960) and/or 2922 (in the distal section 2980) may vary depending, for example, on a desired bending and/or outward expansion force. As described above, the connector elements 2912 and/or 2922 may bend as the scaffold 2950 transitions from the expanded state to the collapsed state. In the example shown, the connector elements 2912 and 2922 may each have a straight portion 2991 and curved portions 2992 where they are connected to the axially extending elongate elements 2911. Note that in this example, the radius of curvature of the curved portions 2992 of the connector elements 2912 and 2922 is smaller than the radius of curvature of the connector elements in the example scaffold 850 of FIGS. 27A and 27B. In some cases, the connector elements 2912/2922 are arranged circumferentially around the scaffold 2950 in zig-zag patterns.

An angle α between the connector elements 2912 in the proximal section 2960 (or connector elements 2922 in the distal section 2980) and the axially extending elements 2911 may range from about 30 degrees and 50 degrees. As shown in the figures, the rows of connector elements 2912 as they extend radially or circumferentially around the proximal and/or distal sections can generally resemble a zig-zag or chevron pattern. In some embodiments, such as when the angle α between the connector elements and the axially extending elements is around 45 degrees, adjacent connector elements can be generally orthogonal or perpendicular to another.

In general, the scaffold patterns may be customized to achieve particular performance characteristics. As described above, the angle ⊖ may be chosen to achieve a desired amount of lateral bendability and axial rigidity of the central section (e.g., 2970). In addition, the scaffold pattern in and around the proximal section (e.g., 2960) and the distal section (e.g., 2980) may at least partially determine the radial and/or bending stiffness of the proximal and distal sections. On one hand, it may be desirable for the proximal section (e.g., 2960) and the distal section (e.g., 2980) to have a high enough radial stiffness when in an expanded state to withstand radially inward pressures experienced while the blood pump is operating within the patient's body. Further, it may be desirable for the proximal section (e.g., 2960) and the distal section (e.g., 2980) to have a high enough bending stiffness to withstand deformation when a lateral force is applied to the side of the scaffold as the blood conduit traverses the walls of the patient's vessels and/or chambers of the heart. Such radial and/or bending stiffness may maintain the blood conduit in the expanded state to prevent the impellers from contacting the inner walls of the blood conduit during pump operation. On the other hand, it may be desirable for the proximal section (e.g., 2960) and the distal section (e.g., 2980) to be able to take on a collapsed state having a sufficiently small diameter for re-sheathing without having to apply an undue amount of a sheathing force. The ability of the scaffold to collapse may at least partially be associated with a degree of elastic strain in the scaffold. In some examples, higher amounts of elastic strain (versus plastic strain) are associated with a greater ability to compress into the collapsed state without permanently deforming the scaffold. The scaffold pattern may be designed to reduce such sheathing strain. In cases where the scaffold is made of a shape memory material, the scaffold may be heat set to have desired shape and material characteristic at a particular temperature (e.g., body temperature). In some cases, one or more computer modeling techniques (e.g., finite element analysis or other modeling analyses) are used to estimate a degree of strain the scaffold experiences during use based on scaffold pattern, material, and/or other variables.

FIG. 30 illustrates a flattened view of another exemplary scaffold 3050, which is similar to scaffold 2950 shown in FIGS. 29A-29E but having a different scaffold pattern variation. Like scaffold 2950, the scaffold 3050 includes a proximal scaffold section 3060, a central scaffold section 3070 and a distal scaffold section 3080, where the proximal section 3060 may be configured to at least partially enclose a proximal impeller, and the distal section 3080 may be configured to at least partially enclose a distal impeller. The scaffold 3050 includes a series of axially extending elongate elements 3011 that extend from the proximal section 3060, through the central section 3070, and to the distal section 3080. Like scaffold 2950, the scaffold 3050 includes ten axially extending elongate elements 3011.

Various feature dimensions of the scaffold 3050 may be similar to those of scaffold 2950 of FIGS. 29A-29E. For example, an angle ⊖ of the axially extending elongate elements 3011 within the central section 3070 may be the same as scaffold 2950. As with the scaffold 2950, a width 3027 of the axially extending elongate elements 3011 within the central section 3070 may be less than a width 3028 of the axially extending elongate elements 3011 within the proximal section 3060 and/or a width 3029 of the axially extending elongate elements 3011 within the distal section 3080. The axial lengths 3061 of the proximal struts 3052 may be the same as the axial lengths 2961 of the proximal struts 2952, and the axial lengths 3081 of the distal struts 3051 may be the same as the axial lengths 2981 of the distal struts 2951. The widths 3027, 3028 and 3029 may be the same as the widths 2927, 2928 and 2929 of scaffold 2950, respectively. The radius of curvature of each axially extending element 3011 within transition regions 3047 may be the same as that of the axially extending elements 2911 within the transition regions 2947 of scaffold 2950. The proximal section 3060 may have a greater radial and/or bending stiffness compared to the distal section 3080.

The scaffold 3050 of FIG. 30 has a different connector element pattern compared to the scaffold 2950 of FIGS. 29A-29E, which may allow the scaffold 3050 to have reduced sheathing strains compared to the scaffold 2950. An angle α between the connector elements 3012 in the proximal section 3060 (or connector elements 3022 in the distal section 3080) and the axially extending elements 3011 are less than the angle α in the scaffold 2905 of FIGS. 29A-29E. In some examples, the angle α may range from about 10 degrees and 30 degrees. The axial length 3075 of the proximal section 3060 may be substantially the same as the axial length 2975 of the proximal section 2960 of the scaffold 2905 of FIGS. 29A-29E. However, due to the lesser angle α, the proximal section 3060 includes three annular rows of connector elements 3012 (compared to five annular rows of connector elements 2912 of scaffold 2950), and the distal section 3080 includes two annular rows of connector elements 3022 (compared to three annular rows of connector elements 2922 of scaffold 2950). Having fewer annular rows of connector elements 3012/3022 may allow for easier collapse of the scaffold from the expanded configuration to the collapsed configuration. In addition, the lengths of the connector elements 3012 are greater than the lengths of the connector elements 2912, and the lengths of the connector elements 3022 are greater than the lengths of the connector elements 2922. Likewise, a first distance 3034 between the connector elements 3012 are greater than the first distance 2934 between the connector elements 2912, and a second distance 3036 between the connector elements 3022 are greater than the second distance 2936 between the connector elements 2922.

In some examples, the first distance 3034 between the connector elements 3012 of the proximal section 3060 may be within a range bounded by any two of the following values: 5.0 mm, 5.5 mm, 6.0 mm, 6.5 mm, and 7.0 mm.

In some examples, the second distance 3036 between the connector elements 3022 of the distal section 3080 may be within a range bounded by any two of the following values: 6.0 mm, 6.5 mm, 7.0 mm, 7.5 mm, and 8.0 mm.

FIG. 31 illustrates a flattened view of further exemplary scaffold 3150, which is similar to scaffold 3050 (FIG. 30) but having a different scaffold pattern. Like scaffold 3050, the scaffold 3150 includes a proximal scaffold section 3160, a central scaffold section 3170 and a distal scaffold section 3180, where the proximal section 3160 may be configured to at least partially enclose a proximal impeller, and the distal section 3180 may be configured to at least partially enclose an (optional) distal impeller. The scaffold 3150 includes a series of axially extending elongate elements 3111 that extend from the proximal section 3160, through the central section 3170, and to the distal section 3180. Like scaffold 3050, the scaffold 3150 includes ten axially extending elongate elements 3111.

Various feature dimensions of the scaffold 3150 may be similar to that of scaffold 3050. For example, an angle Θ of the axially extending elongate elements 3111 within the central section 3170 may be the same as scaffold 3050. As with the scaffold 3050, a width 3127 of the axially extending elongate elements 3111 within the central section 3170 may be less than a width 3128 of the axially extending elongate elements 3111 within the proximal section 3160 and/or a width 3129 of the axially extending elongate elements 3111 within the distal section 3180. The widths 3127, 3128 and 3129 may be the same as scaffold 3050. The radius of curvature of each axially extending element 3111 within transition regions 3147 may be the same as that of scaffold 3050. The proximal section 3160 may have a greater radial and/or bending stiffness compared to the distal section 3180.

The proximal section 3160 of scaffold 3150 has a slightly longer axial length 3175 compared to the axial length 3075 of the proximal section 3060 of scaffold 3050 of FIG. 30. The longer axial length 3175 may provide more radial and/or bending stiffness to the proximal section 3160 of scaffold 3150 compared to the proximal section 3060 of the scaffold 3050. The axial lengths 3161/3181 of the proximal/distal struts 3152/3151 may be less than the axial lengths 3061/3081 of the proximal/distal struts 3052/3051 so that the overall the axial length of the scaffold 3150 is substantially the same as the scaffold 3050. In addition, the proximal section 3160 of scaffold 3150 has a different connector element pattern compared to the proximal section 3060 of scaffold 3050. For example, the proximal section 3160 has four annular rows of connector elements 3112 compared to the three annular rows of connector elements 3012 of scaffold 3050. This increased number of connector elements may allow for more structural support around the proximal impeller.

FIGS. 32A and 32B illustrate another exemplary scaffold 3250. FIG. 32A shows a flattened view of the scaffold 3250. The scaffold 3250 is similar to the scaffold 3150 shown in FIG. 31. An angle Θ of the axially extending elongate elements 3211 within the central section 3270 may be the same as scaffold 3150. An angle α between the connector elements 3212 in the proximal section 3260 (or connector elements 3222 in the distal section 3280) and the axially extending elements 3211 may be the same as scaffold 3150. As with the scaffold 3150, an axial length 3279 of the central section 3270 may be longer than an axial length 3275 of the proximal section 3260 and/or an axial length 3277 of the distal section 3280. As with the scaffold 3150, the axial length 3275 of the proximal section 3260 may be longer than the axial length 3277 of the distal section 3280. As with the scaffold 3150, a width 3227 of the axially extending elongate elements 3211 within the central section 3270 may be less than a width 3228 of the axially extending elongate elements 3211 within the proximal section 3260 and/or a width 3229 of the axially extending elongate elements 3211 within the distal section 3280. A width 3228 of the axially extending elongate elements 3211 within the within the proximal section 3160 and a width 3229 of the axially extending elongate elements 3211 within the distal section 3280 may be the same as those in the scaffold 3150. The radius of curvature of each axially extending element 3211 within transition regions 3247 may be the same as that of scaffold 3050. The proximal section 3260 may have a greater radial and/or bending stiffness compared to the distal section 3280.

One of the differences between the scaffold 3250 and scaffold 3150 (FIG. 31) is the number of struts. The scaffold 3250 includes eight proximal struts 3252 and eight distal struts 3251 compared to the five proximal struts 3150 and five distal struts 3152 of scaffold 3150. In addition, the proximal struts 3252 and distal struts 3251 have smaller widths 3299 than those of the scaffold 3150. The smaller strut widths may accommodate the greater number of struts 3252/3251 in the scaffold 3250. In some examples, the widths of the proximal and distal struts 3252/3251 of scaffold 3250 are about 10-90% smaller that the widths of the struts 3152/3151 of scaffold 3150. The smaller strut widths may also change the radial and/or bending stiffness and/or sheathing strain characteristics of the scaffold 3250.

Another difference between the scaffold 3250 and scaffold 3150 (FIG. 31) is the scaffold patterns of the proximal section 3260 and distal section 3280. In addition to the axially extending elongate elements 3211, the proximal section 3260 of scaffold 3250 includes auxiliary axially extending elements 3298, which are shorter than the axially extending elongate elements 3211 and do not extend into the central section 3270. In addition, the proximal section 3260 and distal section 3280 of the scaffold 3250 has a greater number of connector elements 3221/3222 compared to the scaffold 3150. Further, the distal section 3280 includes three annular rows of connecting elements 3222 compared to two annular rows of connecting elements 3122 in the distal section 3180 of scaffold 3150. The widths 3228 of the axially extending elongate elements 3211 within the proximal section 3260 and distal section 3280 may be less (e.g., 10-90% less) that those of the scaffold 3150 to accommodate the greater number of elements. This difference in number and width of axially extending elongate elements 3211 and number of connecting elements 3222 may result in a different radial and/or bending stiffness and/or sheathing strain characteristic of the scaffold 3250.

Another difference between the scaffold 3250 and scaffold 3150 (FIG. 31) is the characteristics of the axially extending elongate elements 3211 within the central section 3270. The scaffold 3250 includes eight axially extending elongate elements 3211 within the central section 3270, whereas the scaffold 3150 includes ten axially extending elongate elements 3111 within the central section 3170. In addition, the widths 3227 of the axially extending elongate elements 3211 in the scaffold 3250 are smaller than the widths 3127 of the axially extending elongate elements 3111 in the scaffold 3150. The lesser number and smaller widths of the axially extending elongate elements 3211 within the central section 3270 may be associated with greater lateral bendability of the central section 3270 compared to that of scaffold 3150.

The axial lengths of the proximal section 3260, central section 3270 and/or distal section 3280 may be slightly different than those of the scaffold 3150 (FIG. 31) to accommodate the different number and arrangement of struts, axially extending elongate elements and connector elements. In some cases, the length 3275 of proximal section 3260 of scaffold 3250 is less than the length 3175 of proximal section 3160 of scaffold 3150. In some cases, the length 3279 of central section 3270 of scaffold 3250 is greater than the length 3179 of central section 3170 of scaffold 3150. In some cases, the length 3277 of distal section 3280 of scaffold 3250 is the same as the length 3177 of central section 3180 of scaffold 3150.

FIG. 32B shows the scaffold 3250 in a radially expanded state. In FIG. 32B, the struts 3252 and 3251 are shown in a straightened state (e.g., before shape setting and coupling to the central hub(s)). When coupled to the central hub (which may include a bearing assembly), the struts 3252 and 3251 may curve radially inward and connect to the central hub, such as shown in FIG. 29B.

FIGS. 33A-33B illustrate another exemplary scaffold 3350. FIG. 33A shows a flattened view of the scaffold 3350, and FIG. 33B shows a three-dimensional view of the scaffold in an expanded state. The scaffold 3350 can be similar to, and include many of the same elements as, previously described scaffolds, including a proximal section 3360, central section 3370, and distal section 3380. One of the differences between scaffold 3350 and the previously described scaffolds is the number of struts. The scaffold 3350 includes ten proximal struts 3352 and five distal struts 3351. It should be understood that in other embodiments, the number of distal and proximal struts can be different. In general, in this embodiment, the scaffold can have twice as many proximal struts as distal struts (i.e., eight proximal struts and four distal struts, ten proximal struts and five distal struts, twelve proximal struts and six distal struts, etc.). Additionally, the proximal struts 3352 can have a greater width than that of the distal struts 3351. In one embodiment, as shown, the width of the distal struts 3351 is generally the same as a width of the axially extending elongate elements 3311.

Since the scaffold 3350 has a different number of proximal struts than distal struts, there are more connector elements 3312 in the proximal section 3360 than there are connector elements 3322 in the distal section 3380. As shown in FIG. 33A, the proximal section 3360 can have twenty connector elements 3312 in each annular row of connector elements, compared to only ten connector elements 3322 in each annular row of connector elements in the distal section 3380. Generally, the number of connector elements 3312 in the proximal section 3360 is twice the number of proximal struts 3352. Similarly, the number of connector elements 3322 in the distal section 3380 is twice the number of distal struts 3351.

Additionally, still referring to FIG. 33A, the central section can include ten axially extending elongate elements 3311. Generally, the scaffold 3350 can include the same number of axially extending elongate elements 3311 as proximal struts 3352. Therefore, the illustrated example includes ten proximal struts 3352 and ten axially extending elongate elements 3311. In the proximal section 3360, an axially extending elongate element 3311 can extend in the distal direction from each distally facing apex 3382 of the distal most annular row of connector elements 3312. In contrast, in the distal section 3380, an axially extending elongate element 3311 can extend in the proximal direction from each proximally facing apex 3384 and each distal facing apex 3386 of the annular row of connector elements 3322.

The proximal section 3360 of scaffold 3350 can also include auxiliary axially extending elements 3398, which are shorter than the axially extending elongate elements 3211 and do not extend into the central section 3270. The distal section 3380, however, does not include auxiliary axially extending elongate elements because the distal section includes only a single annular row of connector elements 3322. Generally, the auxiliary axially extending elongate elements are only included in the distal section or the proximal section when more than one annular row of connector elements is used.

Another difference between the scaffold 3350 and previously described scaffolds is the number of annular rows of connector elements in the proximal section and the distal section. Referring to FIGS. 33A-33B, the proximal section 3360 can include two annular rows of connector elements 3312. The proximal section 3360 of the scaffold 3350 encompasses or surrounds at least a portion of a proximal impeller (not shown). In contrast, the distal section 3380 can include a single annular row of connector elements 3322. In the embodiment of FIGS. 33A-33B, there is no distal impeller positioned in the distal section, so the pump is designed and configured to operate as a single (proximal) impeller device. However it should be understood that a distal impeller could be included if desired.

FIG. 34 shows another exemplary scaffold 3450, with some changes compared to scaffold 3350 of FIGS. 33A-33B. One difference is that the distal section 3480 of scaffold 3450 includes two annular rows of connector elements 3422, compared to only a single annular row of connector elements in the embodiment of FIGS. 33A-33B. The additional annular row(s) of connector elements provides additional stiffness in the distal section 3480 compared to distal section 3380 of scaffold 3350. Since the distal section includes two annular rows, the distal section and the proximal section can both include auxiliary axially extending elements 3498 extending between the annular rows of connector elements. Despite the scaffold 3450 including two annular rows of connector elements in both the proximal section 3460 and the distal section 3480, in an exemplary embodiment only a single proximal impeller is housed in the proximal section and no distal impeller is housed in the distal section. However, it should be understood that the scaffold could be used to house both distal and proximal impellers if desired.

Since the scaffold 3450 has two annular rows of connector elements in both the proximal section and the distal section, the pattern of structural elements in the proximal section can define a set of apertures 3466 and the pattern of structural elements in the distal section can define a set of apertures 3468. The pattern of structural elements that defines the set of apertures can include the connector elements and the auxiliar axially extending elements in each section. Since the distal section has fewer distal struts, and therefore fewer connector elements, the apertures 3468 of the distal section can be smaller than the apertures of the proximal section.

Another difference between scaffold 3450 and scaffold 3350 is that the distal struts 3451 can have at least a portion with a greater width than the proximal struts 3452. As a result, the width of the axially extending elongate elements 3411 can gradually taper from a first width to a second (thinner) width in tapering region 3488. In some embodiments, as shown in FIG. 34, the distal struts 3451 can further include a taper 3490 from a first width to a second (thinner) width. The portion of the distal strut that is distal to the taper 3490 can be designed and configured to be overmolded or fit into a distal hub (not shown).

What is claimed is:

1. An intravascular blood pump, comprising:
   a collapsible blood conduit defining an inner lumen for moving blood therethrough, the collapsible blood conduit including:
   a proximal section defined by at least two annular rows of connector elements arranged around a central axis of the collapsible blood conduit;
   a distal section defined by at least one annular row of connector elements arranged around the central axis of the collapsible blood conduit;
   a central section disposed axially between the distal and proximal sections, the central section including a plurality of axially extending elongate elements arranged in a helical pattern, wherein the central section includes at least one of material or structure such that when a rotational force is applied to a distal end of the blood conduit, the central section is less resistant to collapse than the proximal and distal sections; and
   a proximal impeller disposed within at least a portion of the proximal section.

2. The intravascular blood pump of claim 1, wherein the proximal, central and distal sections are coupled together.

3. The intravascular blood pump of claim 1, wherein the central section has a relative flexibility compared to the distal and proximal sections such that, in response to a lateral force on the blood conduit in the distal impeller section, the blood conduit deforms and assumes a configuration in which the central section has a higher degree of bend than the proximal and distal sections.

4. The intravascular blood pump of claim 1, wherein at least portions of the proximal and distal sections are free of helical scaffold patterns.

5. The intravascular blood pump of claim 1, wherein the axially extending elongate elements extend between the least two annular rows of connector elements in the proximal section.

6. The intravascular blood pump of claim 1, wherein the distal section is defined by at least two annular rows of connector elements arranged around the central axis of the collapsible blood conduit.

7. The intravascular blood pump of claim 6, wherein the axially extending elongate elements extend between the least two annular rows of connector elements in the distal section.

8. The intravascular blood pump of claim 1, wherein the proximal section is defined by at least four annular rows of connector elements arranged around the central axis of the collapsible blood conduit.

9. The intravascular blood pump of claim 1, wherein the connector elements in each annular row are in a zig-zag pattern.

10. The intravascular blood pump of claim 1, wherein an angle between the connector elements and the axially extending elongate elements ranges from about 10 degrees and 50 degrees.

11. The intravascular blood pump of claim 1, wherein an angle between the connector elements and the axially extending elongate elements ranges from about 10 degrees and 30 degrees.

12. The intravascular blood pump of claim 1, wherein an angle between the connector elements and the axially extending elongate elements ranges from about 30 degrees and 50 degrees.

13. The intravascular blood pump of claim 1, wherein an axial length of the blood conduit ranges from about 50 mm to about 80 mm.

14. The intravascular blood pump of claim 1, wherein the proximal section has a greater lateral bending stiffness than the distal section.

15. The intravascular blood pump of claim 1, wherein the collapsible blood conduit comprises a scaffold configured to transition between a collapsed state and an expanded state, wherein the scaffold has a diameter ranging from 5.0 mm to 10 mm in the expanded state and a diameter ranging from 2.5 mm to 4.5 mm in the collapsed state.

16. The intravascular blood pump of claim 1, further comprising a plurality of proximal struts extending proximally from the proximal section.

17. The intravascular blood pump of claim 16, further comprising a plurality of distal struts extending distally from the distal section.

18. The intravascular blood pump of claim 17, wherein the plurality of proximal struts numbers twice as many as the plurality of distal struts.

19. The intravascular blood pump of claim 17, wherein the intravascular blood pump includes ten proximal struts and five distal struts.

20. The intravascular blood pump of claim 17, wherein a width of the distal struts is greater than a width of the proximal struts.

21. The intravascular blood pump of claim 20, wherein the axially extending elongate elements increase in width near the distal section.

22. An intravascular blood pump, comprising:

a collapsible blood conduit defining an inner lumen for moving blood therethrough, the collapsible blood conduit including:

a proximal section defined by at least two annular rows of connector elements arranged around a central axis of the collapsible blood conduit;

a plurality of proximal struts extending proximally from the proximal section;

a distal section defined by at least one annular row of connector elements arranged around the central axis of the collapsible blood conduit;

a plurality of distal struts extending distally from the distal section, wherein a width of the distal struts is greater than a width of the proximal struts;

a central section disposed axially between the distal and proximal sections, the central section including a plurality of axially extending elongate elements arranged in a helical pattern; and a proximal impeller disposed within at least a portion of the proximal section.

* * * * *